(12) United States Patent
Chen et al.

(10) Patent No.: US 9,918,998 B2
(45) Date of Patent: Mar. 20, 2018

(54) PHARMACEUTICAL TETRACYCLINE COMPOSITION FOR DERMATOLOGICAL USE

(71) Applicant: BioPharmX, Inc., Menlo Park, CA (US)

(72) Inventors: Xin Chen, Palo Alto, CA (US); Maiko C. Hermsmeier, San Jose, CA (US); Diana Lac, Palo Alto, CA (US); Douglas W. Thomas, Palo Alto, CA (US); Noymi Yam, Sunnyvale, CA (US); Akira Yamamoto, Cupertino, CA (US)

(73) Assignee: BioPharmX, Inc., Menlo Park, CA (US)

( * ) Notice: Subject to any disclaimer, the term of this patent is extended or adjusted under 35 U.S.C. 154(b) by 0 days.

(21) Appl. No.: 15/077,858

(22) Filed: Mar. 22, 2016

(65) Prior Publication Data

US 2016/0279152 A1    Sep. 29, 2016

Related U.S. Application Data

(60) Provisional application No. 62/304,119, filed on Mar. 4, 2016, provisional application No. 62/279,654, filed on Jan. 15, 2016, provisional application No. 62/266,650, filed on Dec. 13, 2015, provisional application No. 62/251,001, filed on Nov. 4, 2015, provisional application No. 62/245,262, filed on Oct. 22, 2015, provisional application No. 62/137,216, filed on Mar. 23, 2015.

(51) Int. Cl.
| | |
|---|---|
| A61K 31/65 | (2006.01) |
| A61K 9/00 | (2006.01) |
| A61K 47/02 | (2006.01) |
| A61K 47/10 | (2017.01) |

(52) U.S. Cl.
CPC ............ *A61K 31/65* (2013.01); *A61K 9/0014* (2013.01); *A61K 47/02* (2013.01); *A61K 47/10* (2013.01)

(58) Field of Classification Search
CPC ......... A61K 31/65; A61K 9/0014; A61K 9/06
See application file for complete search history.

(56) References Cited

U.S. PATENT DOCUMENTS

| | | | |
|---|---|---|---|
| 2,990,331 A | 6/1961 | Horst et al. | |
| 3,275,513 A | 9/1966 | Nash et al. | |
| 3,335,055 A | 8/1967 | Weidenheimer et al. | |
| 3,389,175 A | 6/1968 | Nash et al. | |
| 3,538,216 A | 11/1970 | Polin et al. | |
| 3,957,972 A | 5/1976 | Weber et al. | |
| 3,957,980 A | 5/1976 | Noseworthy | |
| 4,081,527 A | 3/1978 | Armstrong et al. | |
| 4,081,528 A | 3/1978 | Armstrong | |
| 4,126,680 A | 11/1978 | Armstrong | |
| 4,376,118 A | 3/1983 | Daher et al. | |
| 4,701,320 A | 10/1987 | Hasegawa et al. | |
| 4,772,460 A | 9/1988 | Malook et al. | |
| 4,931,467 A | 6/1990 | Saint-Leger et al. | |
| 5,075,295 A | 12/1991 | Zupan et al. | |
| 5,108,991 A | 4/1992 | Rajadhyaksha | |
| 5,122,519 A | 6/1992 | Ritter | |
| 5,298,238 A * | 3/1994 | Hussein | A61K 8/347 424/49 |
| 5,538,954 A | 7/1996 | Koch et al. | |
| 5,807,568 A | 9/1998 | Cody et al. | |
| 5,908,838 A | 6/1999 | Gans | |
| 6,077,822 A | 6/2000 | Dyrsting et al. | |
| 6,110,905 A | 8/2000 | Patterson et al. | |
| 6,294,186 B1 | 9/2001 | Beerse et al. | |
| 6,310,053 B1 | 10/2001 | Patterson et al. | |
| 6,482,839 B1 | 11/2002 | Thornfeldt | |
| 6,566,350 B2 | 5/2003 | Ono et al. | |
| 6,943,197 B2 | 9/2005 | Maibach et al. | |
| 7,018,660 B2 | 3/2006 | Murad | |
| 7,541,347 B2 | 6/2009 | Wortzman et al. | |
| 7,790,705 B2 | 9/2010 | Wortzman et al. | |
| 7,807,842 B2 | 10/2010 | Myers et al. | |

(Continued)

FOREIGN PATENT DOCUMENTS

| | | |
|---|---|---|
| CN | 102008490 A | 4/2011 |
| CN | 102228462 A | 11/2012 |

(Continued)

OTHER PUBLICATIONS

Ammar et al., "Evaluation of chemical penetration enhancers for transdermal delivery of aspirin", Asian J. Pharm. Sci., vol. 2, No. 3, pp. 96-105 (2007).

Barry, "Mode of action of penetration enhancers in human skin", J. Contr. Rel., vol. 6, pp. 85-97 (1987).

Benson, "Transdermal Drug Delivery: Penetration Enhancement Techniques", Current Drug Del., vol. 2, pp. 23-33 (2005).

Bernstein et al., "Topically applied erythromycin inflammatory acne vulgaris", Am. Acad. Dermatol., vol. 2, No. 4, pp. 318-321 (1980).

Berthon et al., "Metal Ion-Tetracycline Interactions in Biological Fluids. 2. Potentiometric Study of Magnesium Complexes with Tetracycline, Oxytetracycline, Doxycycline, and Minocycline, and Discussion of their Possible Influence on the Bioavailability of these Antibiotics in Blood Plasma", J. Inorg. Biochem., vol. 19, pp. 1-18 (1983).

(Continued)

*Primary Examiner* — Theodore R. West
(74) *Attorney, Agent, or Firm* — Robert Kehl Sink; Jacqueline F. Mahoney; McDermott Will & Emery LLP

(57) ABSTRACT

Provided herein is a topical composition and related methods for making and using the composition. In a first aspect, the topical composition comprises minocycline, a magnesium salt, and a sulfite compound in a non-aqueous solvent. In yet another aspect, the topical composition comprises a tetracycline-class drug, a source of magnesium, a monohydric aliphatic alcohol, and a polyol, wherein (i) the ratio between the monohydric aliphatic alcohol and the propylene glycol is in the range of 1:1 to 99:1 by weight and (ii) the tetracycline-class drug is dissolved in the topical composition.

42 Claims, 26 Drawing Sheets
(7 of 26 Drawing Sheet(s) Filed in Color)

(56) References Cited

U.S. PATENT DOCUMENTS

| | | | |
|---|---|---|---|
| 7,820,641 B2 | 10/2010 | Nelson et al. |
| 7,919,483 B2 | 4/2011 | Wortzman et al. |
| 7,943,600 B2 | 5/2011 | Froim et al. |
| 8,052,983 B2 | 11/2011 | Ashley |
| 8,071,075 B2 | 12/2011 | Reed et al. |
| 8,252,776 B2 | 8/2012 | Wortzman et al. |
| 8,268,804 B2 | 9/2012 | Wortzman et al. |
| 8,338,477 B2 | 12/2012 | Duncan et al. |
| 8,343,945 B2 | 1/2013 | Tamarkin et al. |
| 8,383,610 B2 | 2/2013 | Cvetovich et al. |
| 8,415,331 B2 | 4/2013 | deVries et al. |
| 8,486,376 B2 | 7/2013 | Friedman et al. |
| 8,486,921 B2 | 7/2013 | Myers et al. |
| 8,618,081 B2 | 12/2013 | Tamarkin et al. |
| 8,722,650 B1 | 5/2014 | Wortzman et al. |
| 8,945,516 B2 | 2/2015 | Tamarkin et al. |
| 9,192,615 B2 | 11/2015 | Wortzman et al. |
| 9,278,066 B2 | 3/2016 | Trumbore et al. |
| 9,278,105 B2 | 3/2016 | Griffith et al. |
| 9,481,639 B2 | 11/2016 | Assefa et al. |
| 9,539,266 B2 | 1/2017 | Mansouri |
| 9,549,898 B2 | 1/2017 | Tamarkin et al. |
| 9,592,246 B2 | 3/2017 | Salman |
| 2002/0058010 A1 | 5/2002 | Picard-Lesboueyries et al. |
| 2003/0077301 A1 | 4/2003 | Maibach et al. |
| 2003/0138503 A1 | 7/2003 | Staniforth et al. |
| 2003/0224064 A1 | 12/2003 | Kling |
| 2004/0147492 A1 | 7/2004 | Ashley |
| 2004/0167099 A1 | 8/2004 | Lawter |
| 2004/0198843 A1 | 10/2004 | George et al. |
| 2004/0258757 A1 | 12/2004 | Bosch et al. |
| 2005/0239723 A1 | 10/2005 | Amin et al. |
| 2006/0183719 A1 | 8/2006 | Devries et al. |
| 2007/0003585 A1 | 1/2007 | Clark et al. |
| 2008/0044494 A1 | 2/2008 | Robinson et al. |
| 2008/0119437 A1 | 5/2008 | Lewis |
| 2008/0188445 A1 | 8/2008 | Muldoon et al. |
| 2008/0188446 A1 | 8/2008 | Muldoon et al. |
| 2008/0233206 A1 | 9/2008 | Chomczynski |
| 2008/0248124 A1 | 10/2008 | Eguchi et al. |
| 2009/0176719 A1 | 7/2009 | Goldstein |
| 2010/0210571 A1 | 8/2010 | Popp |
| 2010/0222403 A1 | 9/2010 | Borgers et al. |
| 2010/0292183 A1 | 11/2010 | Madasamy |
| 2011/0033402 A1 | 2/2011 | Modi |
| 2011/0039805 A1 | 2/2011 | Pflugfelder et al. |
| 2011/0165251 A1 | 7/2011 | Bosch et al. |
| 2012/0028929 A1 | 2/2012 | Power et al. |
| 2012/0181201 A1 | 7/2012 | Heggie |
| 2012/0190653 A1 | 7/2012 | Gilbard et al. |
| 2012/0289521 A1 | 11/2012 | Weidner |
| 2012/0328701 A1 | 12/2012 | Edelson et al. |
| 2013/0030195 A1 | 1/2013 | Mendes et al. |
| 2013/0040918 A1 | 2/2013 | Griffith et al. |
| 2013/0123217 A1 | 5/2013 | Duncan et al. |
| 2013/0189191 A1 | 7/2013 | Tamarkin et al. |
| 2013/0195986 A1 | 8/2013 | Heggie et al. |
| 2014/0128351 A1 | 5/2014 | Fein et al. |
| 2014/0147504 A1 | 5/2014 | Salman et al. |
| 2014/0194393 A1 | 7/2014 | Griffith et al. |
| 2014/0221320 A1 | 8/2014 | Joks et al. |
| 2015/0056148 A1 | 2/2015 | Tamarkin et al. |
| 2015/0056149 A1 | 2/2015 | Tamarkin et al. |
| 2015/0094282 A1 | 4/2015 | Griffith et al. |
| 2015/0094290 A1 | 4/2015 | Morgan et al. |
| 2015/0272926 A1 | 10/2015 | Zouboulis |
| 2015/0343070 A1 | 12/2015 | Jahagirdar et al. |
| 2016/0287614 A1 | 10/2016 | Mandhare et al. |

FOREIGN PATENT DOCUMENTS

| | | | |
|---|---|---|---|
| EP | 0038013 B1 | 10/1981 | |
| EP | 184389 A2 * | 11/1985 | ............. A61K 31/65 |
| EP | 1902706 A1 | 3/2008 | |
| GB | 901107 A | 7/1962 | |
| WO | WO 1996/012487 A1 | 5/1996 | |
| WO | WO 2001/028338 A2 | 4/2001 | |
| WO | WO 2002/100420 A2 | 12/2002 | |
| WO | WO 2007/099396 A2 | 9/2007 | |
| WO | WO 2008/118744 A1 | 10/2008 | |
| WO | WO 2008/121107 A1 | 10/2008 | |
| WO | WO 2011/143503 A2 | 11/2011 | |
| WO | WO 2012/021712 A1 | 2/2012 | |
| WO | WO 2012/100097 A2 | 7/2012 | |
| WO | WO 2015/066717 A1 | 5/2015 | |
| WO | WO 2016/154232 A2 | 9/2016 | |

OTHER PUBLICATIONS

Chantasart and Li, "Structure Enhancement Relationship of Chemical Penetration Enhancers in Drug Transport across the Stratum Corneum", Pharmaceutics, vol. 4, pp. 71-92 (2012).

Cornwall and Barry, "The routes of penetration of ions and 5fluorouracil across human skin and the mechanisms of action of terpene skin penetration enhancers", Int. J. Pharm., vol. 94, pp. 189-194 (1993).

D'Amato et al., "Effect of Calcium and Magnesium Ions on the Susceptibility of *Pseudomonas* Species to Tetracycline, Gentamicin Polymyxin B, and Carbenicillin", Antimicrob. Agents Chemother., vol. 7, No. 5, pp. 596-600 (1975).

Drakulic et al., "Role of complexes formation between drugs and penetration enhancers in transdermal delivery", Int. J. Pharm., vol. 363, pp. 40-49 (2008).

Geria et al., "Minocycline-induced skin pigmentation: an update", Acta Dermatovenerol Croat., vol. 17, No. 2, pp. 123-126 (2009) Abstract.

Godin and Touitou, "Transdermal skin delivery: Predictions for humans from in vivo, ex vivo and animal models", Adv. Drug Del. Rev., vol. 59, pp. 1152-1161 (2007).

Heard et al., "Skin penetration enhancement of mefenamic acid by ethanol and 1,8-cineole can be explained by the 'pull' effect", Int. J. Pharm., vol. 321, pp. 167-170 (2006).

International Search Report and Written opinion from PCT Patent Application No. PCT/US2016/023646 dated Nov. 9, 2016, application now published as International Publication No. WO 2016/154232 on Sep. 29, 2016.

Jin et al., "$Ca^{2+}$ and $Mg^{2+}$ bind tetracycline with distinct stoichiometries and linked deprotonation", Biophys. Chem., vol. 128, pp. 185-196 (2007).

Jones and Crumley, "Topical Erythromycin vs Blank Vehicle in a Multiclinic Acne Study", Arch. Dermatol., vol. 117, pp. 551-553 (1981).

Knorr et al., "Follicular transport route—Research progress and future perspectives", Eur. J. Pharm. Biopharm., vol. 71, pp. 173-180 (2009).

Lademann et al., "Hair Follicles—A Long-Term Reservoir for Drug Delivery", Skin Pharmacol. Physiol., vol. 19, pp. 232-236 (2006).

Lamb et al., "Metal ion-tetracycline interactions in biological fluids. Part 3. Formation of mixed-metal ternary complexes of tetracycline, oxytetracycline, doxycycline and minocycline with calcium and magnesium, and their involvement in the bioavailability of these antibiotics in blood plasma", Agents and Actions, vol. 14, No. 5/6, pp. 743-750 (1984).

Lane, "Skin penetration enhancers", Int. J. Pharm., vol. 447, pp. 12-21 (2013).

Martin et al., "Equilibrium and kinetic studies on the interaction of tetracyclines with calcium and magnesium", Biophys. Chem., vol. 10, pp. 319-326 (1979).

Ochsendorf, "Minocycline in Acne Vulgaris", Am. J. Clin. Dermatol., vol. 11, No. 5, pp. 327-341 (2010).

Pang and Han, "Review on Transdermal Drug Delivery Systems", J. Pharm. Drug Del., vol. 1, Issue 6, 10 pages (2014).

Rahman et al., Minocycline hyperpigmentation isolated to the subcutaneous fat, J. Cutan. Path., vol. 32, pp. 516-519 (2005).

Santos and Rao, "Antiinflammatory and Antinociceptive Effects of 1,8-Cineole a Terpenoid Oxide Present in many Plant Essential Oils", Phytother. Res., vol. 14, pp. 240-244 (2000).

Sapra et al., "Percutaneous Permeation Enhancement by Terpenes: Mechanistic View", AAPS J., vol. 10, No. 1, pp. 120-132 (2008).

(56) References Cited

OTHER PUBLICATIONS

Sinha and Maninder Pal Kaur, "Permeation Enhancers for Transdermal Drug Delivery", 141. Drug Del. Ind. Pharm., vol. 26, No. 11, pp. 1131-1140 (2000).

Solodyn Product Information, "Solodyn (minocycline HCI) Extended Release Tablets, for oral use", Reference ID: 3392941, 21 pages (2013).

Tongaree et al., "The Effects of pH and PEG 400—Water Cosolvents on Oxytetracycline-Magnesium Complex Formation and Stability", Pharm. Dev. Tech., vol. 5, No. 2, pp. 189-199 (2000).

Trommer and Neubert, "Overcoming the Stratum Corneum: The Modulation of Skin Penetration", Skin Pharmacol. Physiol., vol. 19, pp. 106-121 (2006).

Williams and Barry, "Terpenes and the Lipid-Protein-Partitioning Theory of Skin Penetration Enhancement", Pharm. Res., vol. 8, No. 1., pp. 17-24 (1991).

Williams and Barry, "Penetration enhancers", Adv. Drug Del. Rev., vol. 56, pp. 603-618 (2004).

Wosicka and Cal, Targeting to the hair follicles: Current status and potential, J. Dermatol. Sci., vol. 57, pp. 83-89 (2010).

Xiong et al., Effects of penetration enhancers on in vitro percutaneous absorption of low molecular weight heparin through human skin, J. Contr. Rel., vol. 42, pp. 289-296 (1996).

\* cited by examiner

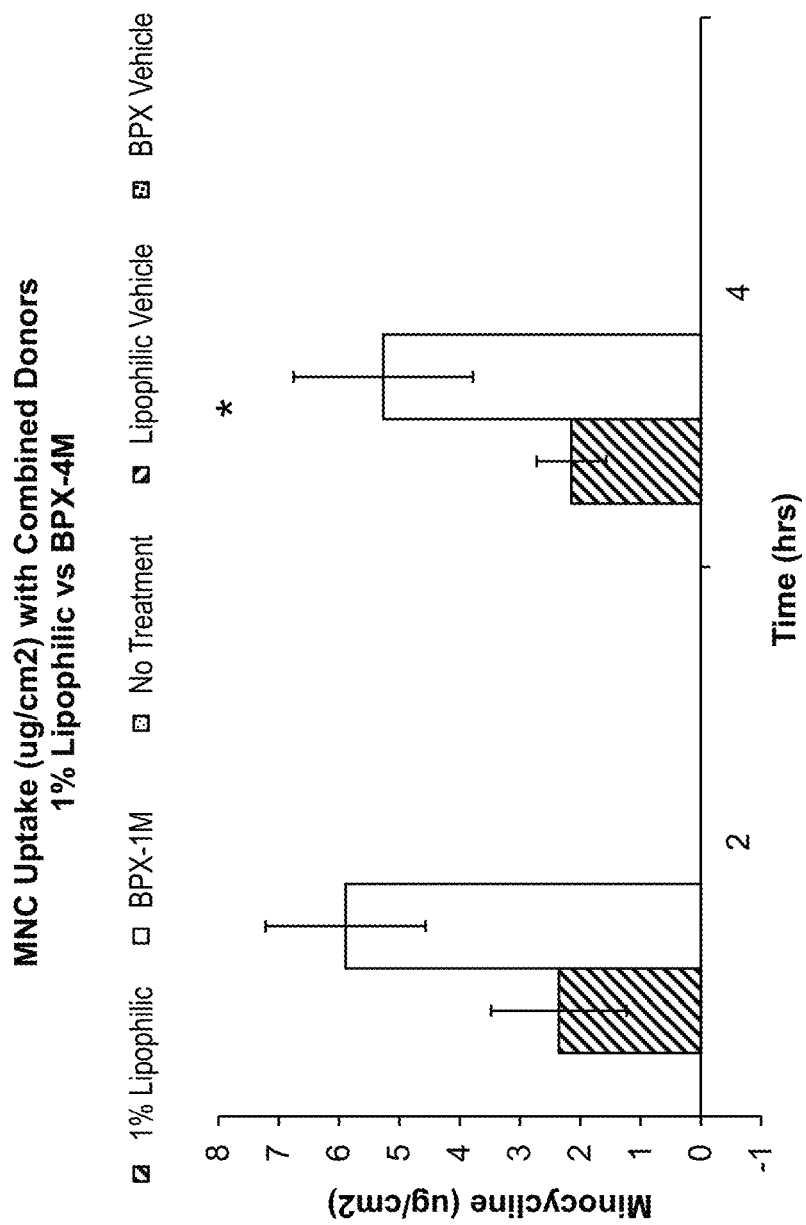

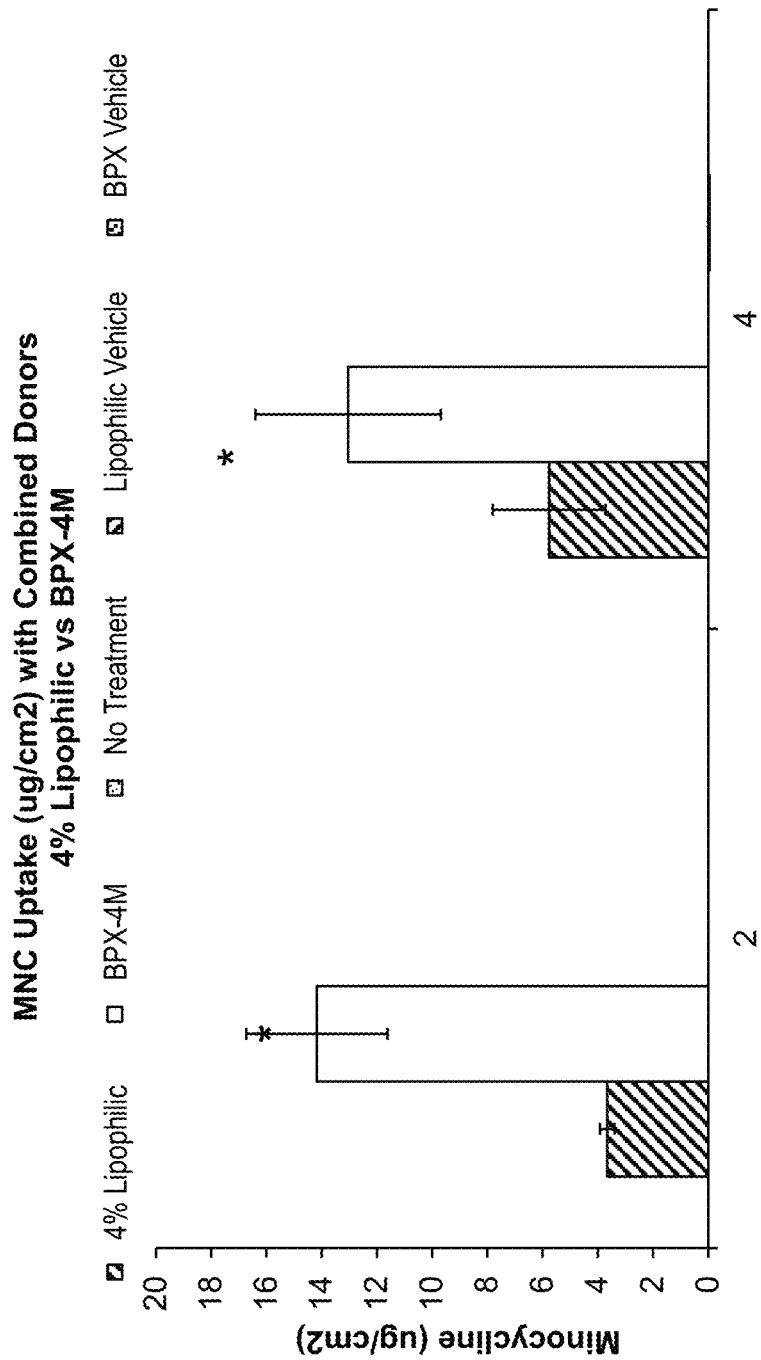

PHARMACEUTICAL TETRACYCLINE COMPOSITION FOR DERMATOLOGICAL USE

CROSS-REFERENCE TO RELATED APPLICATIONS

This application claims the benefit of priority to (i) U.S. Provisional Patent Application No. 62/304,119, filed Mar. 4, 2016; (ii) U.S. Provisional Patent Application No. 62/279,654, filed Jan. 15, 2016; (iii) U.S. Provisional Patent Application No. 62/266,650, filed Dec. 13, 2015; (iv) U.S. Provisional Patent Application No. 62/251,001, filed Nov. 4, 2015; (v) U.S. Provisional Patent Application No. 62/245,262, filed Oct. 22, 2015; and (vi) U.S. Provisional Patent Application No. 62/137,216, filed Mar. 23, 2015, each of which is incorporated herein by reference in its entirety.

FIELD

This disclosure relates generally to pharmaceutical compositions and methods for preparing such compositions, as well as to related uses. Uses include, for example, the treatment of various dermatological conditions and diseases, among other things. More particularly, this disclosure is directed to stable compositions comprising, for example, a tetracycline-class active ingredient, a source of magnesium such as a magnesium salt, a monohydric aliphatic alcohol, and a polyol, and to related methods for making and using such compositions. Also provided are stable compositions comprising, for example, minocycline, a magnesium salt, and a sulfite compound in a non-aqueous solvent and to related methods for making and using such compositions.

BACKGROUND

Several tetracycline class antibiotics have been known for over 50 years, but there have been relatively few commercially developed topical compositions that contain these antibiotics due to a number of challenges that must be addressed simultaneously in order to produce a commercially successful product.

Tetracycline class drugs, and minocycline in particular, are useful for the treatment of acne due to their anti-inflammatory effects. Their use for the treatment of acne has been demonstrated in orally delivered compositions that have shown good efficacy. However, the systemic delivery of tetracycline-class drugs is often accompanied by adverse side effects, such as diarrhea, abdominal cramps, and dizziness. High systemic levels of drug typically lead to greater systemic side effects. These can be beneficially reduced, for example, by using a topical composition that delivers a drug primarily to the skin, rather than primarily systemically. Unfortunately, topical formulations of tetracycline class drugs, such as minocycline, also have the potential for staining the skin, particularly after daily application over multiple weeks.

Intradermal or topical administration of a drug involves entry of the drug across the stratum corneum for a cutaneous or local skin effect; that is, the pharmacological effect of the drug is localized to the intracutaneous regions of drug penetration and deposition. Preferably, intradermal absorption occurs with little or no systemic absorption or accumulation. Intradermal absorption of a drug involves partitioning of the drug from the applied vehicle into the stratum corneum, diffusion of the drug through the stratum corneum, and partitioning of the drug from the stratum corneum into the epidermis. In contrast, transdermal administration involves transport of a drug through the skin such that a therapeutic amount of the drug is achieved in the systemic blood circulation.

Topical compositions that achieve delivery of a drug across the stratum corneum and retention of the majority of the drug intracutaneously such that it does not enter the bloodstream in significant amounts are challenging to design and require innovative approaches. Several factors determine the permeability of the skin or of particular layers of the skin to a topically-applied drug. These factors include the characteristics of the skin, the characteristics of the drug (e.g., its size (molecular weight or molecular volume), lipophilicity/hydrophilicity, polarity, etc.), the dosage of drug applied, the concentration and volume of the composition to be applied, interactions between the drug and the delivery vehicle, interactions between the drug and the skin, and interactions of the drug and the skin in the presence of the ingredients in the delivery vehicle. Because of the multitude of factors involved in the topical administration of a drug, it is generally accepted that whether intracutaneous delivery of a drug can be successfully achieved is uncertain. Thus, topical administration, while desired from a patient convenience and drug delivery view, has been largely unsuccessful for many compounds, including the tetracyclines, as evidenced by the relatively few drugs approved for topical administration.

One significant problem related to the topical administration of a tetracycline-class antibiotic is the identification of a solvent system in which the tetracycline class drug is stable, sufficiently soluble, and able to penetrate into a target tissue or body fluid, such as sebum.

Many tetracycline class drugs are sensitive to degradation by contact with and/or dissolution in hydrophilic oxidizing, reducing, or peroxidizing agents and/or water. As described in U.S. Patent Application Publication No. 2014/0147504, a major challenge in the development of topical formulations of minocycline has been its chemical nature—the drug is unstable in solution form and is also sensitive to moisture, temperature, and light. There have been several compositions that have been developed to address challenges associated with this drug. This instability applies to all currently available tetracycline class drugs.

Salman et al. describe, in U.S. Patent Application Publication No. 2014/0147504, a topical composition in which a tetracycline is suspended in a liquid medium that does not dissolve or minimally dissolves the tetracycline. While this approach is described as limiting the degradation of tetracycline, compositions in which the liquid medium does not dissolve the drug are not preferred due to the inability of the drug within the formulation to readily penetrate the skin. Since many products applied to the skin will be subject to rapid evaporation, it is likely that the drug will remain on the skin surface following its application. Such solid drug forms will not be bioavailable.

Another approach for maintaining the potency of a tetracycline drug is to separate it from potential reactive agents, such as with a coating or physical encapsulation of the drug, to limit its interaction/exposure to the potentially reactive agents. Physical encapsulation can be achieved by a wide variety of techniques. For example, Heggie et al. describe a composition for coating minocycline particles such that the particles are suspended in a solvent, rather than dissolved in it (U.S. Patent Application Publication No. 2013/0195986). However, this approach suffers from many of the same problems described above for use of a solvent system in which the drug is not dissolved.

Several proposed solvent systems, such as ointments, are not commercially viable for treatment of acne due to their possessing an oily feel. Even worse, some such substances may promote the condition that they are designed to treat, such as the use of a comedogenic material as a delivery vehicle for a composition designed to topically treat acne. Additionally, some strongly hydrophobic substances, such as petrolatum, paraffin wax, and/or fatty alcohol can produce an occlusive barrier that limits the drug penetration into the skin. Additionally, some hydrophobic substances have a high viscosity that limits the diffusion of the drug into the skin, thus reducing the bioavailability of the drug and limiting its effectiveness.

Compositions designed for use in non-topical areas have different constraints such that approaches or compositions developed for non-topical use may not be suitable for topical applications. For example, solutions for intravenous injection require an aqueous-based composition in order to be compatible with injection into the blood stream. However, since such injections are typically administered at hospitals and physician's offices with tighter controls on expiration dates and close ties to pharmacies, controlled storage conditions, such as refrigeration, may be more appropriate for intravenously delivered compositions in comparison to topical compositions which are typically stored by patients. In U.S. Patent Application Publication No. 2014/0194393, Griffith et al. propose stabilizing an aqueous minocycline composition using pH modifiers, magnesium chloride, and an antioxidant. However, a maximum stability of only 84.32% after 2 weeks under dark storage conditions at 37° C. is described for an exemplary minocycline composition. This level of stability is not sufficient for most drug applications. The stability of other compositions presented therein varies, but generally strongly aqueous environments do not promote stability for tetracycline class drugs.

Topically applied drug compositions are typically intended to deliver a drug uniformly to one or more depths within the skin tissue to which the composition is applied. However, bacteria for some dermatological conditions and diseases, such as *P. acnes* bacteria for acne, are located primarily in certain types of tissue, such as lipid-rich tissues including sebocytes, or body fluids, such as sebum. For such conditions and diseases, it is more efficient if the topical drug composition can be delivered preferentially to these locations where the bacteria are concentrated.

There is a need for a topically-applied composition that stabilizes an active tetracycline-class drug while enabling sufficient solubility in a delivery vehicle that delivers the drug to target tissue, such as sebaceous glands, or targets body fluids, such as sebum. The composition should maintain a high degree of potency, i.e., activity, of the drug, provide penetration into skin, sebum, and/or sebaceous glands in quantities sufficient to inhibit growth of *Propionibacterium acnes* (*P. acnes*) bacteria in these locations, and should not visibly stain the skin following repeated applications. Some compositions have been provided that meet one or more of these criteria, however, it would be desirable to provide a composition that meets all or most of these criteria in a single composition.

BRIEF SUMMARY

The present disclosure overcomes one or more limitations associated with current tetracycline-class drug-containing topical compositions. In a first aspect, provided herein is a topical composition comprising minocycline, a magnesium salt, and a sulfite compound in a non-aqueous solvent. In one or more preferred embodiments, the composition is for topical administration.

In one or more embodiments related to the first aspect, the non-aqueous solvent comprises a monohydric aliphatic alcohol.

In yet one or more further embodiments, the non-aqueous solvent comprises a monohydric aliphatic alcohol and a polyol. In some related embodiments, the ratio between the monohydric aliphatic alcohol and the polyol is in a range of 1:1 to 99:1 by weight.

In yet one or more further embodiments, the composition comprises a greater percent by weight of the monohydric aliphatic alcohol than the polyol. For example, in one or more related embodiments, the w/w ratio of monohydric aliphatic alcohol to polyol is in a range of about 2:1 to 10:1 by weight.

In yet one or more further embodiments, the minocycline is dissolved in the non-aqueous solvent.

In some embodiments, the molar ratio of the magnesium salt to the minocycline is in a range of about 2:1 to 100:1.

In some additional embodiments related to any one or more of the foregoing, the magnesium salt is magnesium chloride, or is a minocycline salt having a counter ion that is softer than chloride.

In some further embodiments, the monohydric aliphatic alcohol is selected from the group consisting of ethanol, isopropanol, propyl alcohol, tert-butyl alcohol, or combinations thereof. In some particular embodiments, the monohydric aliphatic alcohol is ethanol.

In yet some additional embodiments, the topical composition comprises from about 0.1% to about 4% by weight minocycline.

In one or more further embodiments, the topical composition, when stored at 40° C. in a closed glass vial for a period of 4 weeks, exhibits an increase in the relative concentration of 4-epi-minocycline of less than 1.0% per week. In yet one or more additional preferred embodiments, the topical composition, when stored at 40° C. in a closed glass vial for a period of 4 weeks, exhibits an increase in the relative concentration of 4-epi-minocycline of less than 0.70% per week.

In some embodiments, the topical composition, when stored at 25° C. and 60% relative humidity in a sealed container for 12 months, contains less than 7% minocycline degradation product, where the degradation product is 4-epi-minocycline.

In yet one or more further embodiments, the polyol is a C3-C8 diol or a triol. In yet certain particular embodiments, the polyol is propylene glycol.

In one or more further embodiments, the sulfite compound is either a sulfite salt or is an organic sulfite. In one or more exemplary embodiments, the sulfite compound is a sulfite, bisulfite, pyrosulfite, or metabisulfite compound. In yet one or more particular embodiments, the sulfite compound is an inorganic sulfite. In yet one or more further embodiments, the sulfite is an inorganic sulfite comprising an inorganic cation selected from sodium, potassium, calcium and magnesium.

In one or more further embodiments, the sulfite compound is an organic sulfite. In one or more related embodiments, the sulfite is an ester of sulfurous acid. Illustrative organic sulfites include, e.g., esters of sulfurous acid, acrylic sulfites, and cyclic sulfites. In some particular embodiments, the organic sulfite is an ethyl, p-tolyl-, or isopropyl sulfite.

In some additional embodiments, the topical composition comprises from about 0.005% to about 3.0% by weight of the sulfite compound. In one or more particular embodiments, the sulfite is selected from the group consisting of sodium sulfite, sodium bisulfite, and sodium meta-bisulfite.

In yet some additional embodiments, the topical composition comprises less than about 3 weight percent water. In yet some further embodiments, the topical composition comprises less than about 2 weight percent water.

In some further embodiments, the topical composition further comprises an essential oil. In one or more related embodiments, the essential oil is 1,8-cineole. In some embodiments, the topical composition comprises from about 0.01 to 5 weight percent of 1,8-cineole.

In some further embodiments, the topical composition comprises a thickening agent. In one or more related embodiments, the thickening agent is hydroxypropyl cellulose.

In yet some additional embodiments, the composition is not an emulsion and/or does not comprise nanoparticles or microparticles.

In some further embodiments, the topical composition has an effective pH of 3-6 when mixed with water in a ratio of 1:9 by weight. In some embodiments, the topical composition has an effective pH of about 3.8 to about 5.0 when mixed with water in a ratio of 1:9 by weight.

In yet one or more additional embodiments, the composition is non-irritating when applied to rats daily over a period of 28 days. For instance, a non-irritating composition will generally not irritate the skin or cause an allergic reaction.

In some embodiments, the composition exhibits no significant change in color after aging for 4 weeks at 40° C. in a sealed container. In some particular embodiments related to the foregoing, no significant color change is a color change of less than 20 in distance in 3-dimensional RGB space where each value is measured on a 0-255 range and distance is calculated in 3-dimensional RGB space according to the following formula: distance$_{RGB}$=(($\Delta$R)$^2$+($\Delta$G)$^2$+($\Delta$B)$^2$)$^{0.5}$.

In yet another (or second) aspect, provided is a composition that comprises a tetracycline-class drug or salt or solvate thereof, a source of magnesium such as a magnesium salt, a monohydric aliphatic alcohol, and a polyol, wherein (i) the ratio between the monohydric aliphatic alcohol and the polyol is in the range of 1:1 to 99:1 by weight, and (ii) the tetracycline-class drug is dissolved in the topical composition. Preferably, the composition is for topical administration.

In some embodiments, related to the first or second aspect, the source of magnesium is effective to stabilize the tetracycline drug.

In one or more embodiments related to the second aspect, the molar ratio of magnesium (from the magnesium source) to the tetracycline drug is in a range of about 2:1 to about 100:1. In some related embodiments, the source of magnesium is a magnesium salt having a chloride counter ion or an ion that is softer than chloride.

In one or more additional embodiments, the tetracycline class drug is minocycline, and the source of magnesium is effective to stabilize the minocycline, such upon storage of the composition in a sealed container for 12 months at 25° C. and 60% relative humidity, the composition contains less than 7% minocycline degradation product, where the degradation product is the epimer, 4-epi-minocycline. For example, under the above storage conditions, the ratio of minocycline to epimer, on a w/w basis, is greater than about 13:1. Preferably, the ratio of minocycline to epimer, on a w/w basis, is greater than about 15:1.

In some additional embodiments, at least 90% of the minocycline remains in its active form (i.e., non-epimerized form) after storage for 12 months at 25° C. and 60% relative humidity.

In one or more embodiments of the composition, the monohydric aliphatic alcohol is a liquid at room temperature. In one or more further embodiments, the monohydric aliphatic alcohol is selected from the group consisting of ethanol, isopropanol, propyl alcohol, tert-butyl alcohol, and combinations thereof.

In yet some further embodiments, the monohydric aliphatic alcohol is a volatile monohydric aliphatic alcohol.

In yet some additional embodiments related to the polyol component, the polyol is a liquid at room temperature. In one or more particular embodiments, the polyol is a C3-C8 diol or triol. In yet some more particular embodiments, the polyol is propylene glycol.

In yet some additional embodiments directed to the polyol, the polyol is not glycerol or glycerin.

In some particular embodiments of the composition, the magnesium source is selected from the group consisting of magnesium chloride, magnesium sulfate, magnesium salicylate, and hydrates and combinations thereof.

In one or more preferred embodiments, the tetracycline class drug is minocycline or a salt or solvate thereof. For example, composition may comprise from about 0.01 to 10 percent by weight minocycline or a salt or solvate thereof. In one or more preferred embodiments, the minocycline is not a hydrate.

In other embodiments, the tetracycline class drug is selected from the group consisting of tetracycline, tigecycline, lymecycline, and doxycycline, and salts or solvate thereof.

In yet another embodiment, the tetracycline class drug is a fluorocycline.

In one or more further embodiments, the composition further comprises a thickening agent. In some particular embodiments, the thickening agent is hydroxypropyl cellulose.

In some further embodiments of the composition, the composition possesses a viscosity in a range of 75 to 10,000 centipoise at 25° C. In some further embodiments of the second aspect, the composition comprises one or more additional additives, such as, for example, an antioxidant, a thickener, colorant or other suitable additive.

In some further embodiments, the topical composition is not an emulsion.

In some additional embodiments, the topical composition does not comprise nanoparticles or microparticles.

In certain embodiments, the topical composition is non-aqueous. In alternative embodiments, the topical composition is anhydrous.

In one or more additional embodiments, the composition has an effective pH of 3-6 when mixed with water in a ratio of 1:9 by weight.

In one or more further embodiments, the composition has an effective pH of about 3.8 to about 5.0 when mixed with water in a ratio of 1:9 by weight.

In some embodiments, the penetration efficiency of the composition in accordance with the first and second aspects and related embodiments into ex vivo human facial skin multiplied by the concentration of the tetracycline class drug in the topical composition exceeds the minimum inhibitory concentration (MIC) of the drug for a target bacteria in a target tissue or target body fluid. In one or more related embodiments, the target bacteria is P. acnes.

In some further embodiments, the penetration efficiency into ex vivo human facial skin exceeds 5%. In yet some further embodiments, the penetration efficiency into ex vivo human facial skin is in the range of 5% to 30%. In some embodiments, the efficiency of penetration of the tetracycline class drug will exceed 5%, more preferably will exceed 8%, or more preferably will exceed 10%. In some embodiments, the efficiency of penetration of the tetracycline class drug will be in the range of 5% to 30%, or is in a range of 5% to 25%, or is in the range of 5% to 10%, or more preferably in the range of 10% to 30%.

In yet some further embodiments, the composition dries in less than 60 seconds when applied to a region of skin in vivo.

In yet some additional embodiments in which the composition comprises a polyol and 1,8-cineole, the combination of the polyol and the 1,8-cineole is effective to prevent the skin from scaling and from extreme drying due to extended use for two weeks or more when applied at least 3 times per week.

In yet one or more additional embodiments, the composition is non-staining to a skin tissue when applied to a region of human or rat skin in vivo daily for 2 weeks.

In yet some further embodiments, the composition is non-irritating to a skin tissue when applied to a region of human or rat skin in vivo daily for 2 weeks, e.g., when the composition contains from about 0.1% (w/w) to about 10% (w/w) tetracycline class drug.

In one or more further embodiments, the compositions provided herein are applied directly to the skin. In one or more further embodiments, the compositions provided herein are applied to the cornea, or to the conjunctiva.

Also provided herein is a method of treating acne in a human subject comprising topically applying an effective amount of a composition as provided herein to an exterior epithelial body surface of the human.

In yet a further aspect, provided is a method for treating a condition or disease responsive to treatment with a tetracycline-class drug in a human, where the method comprises topically applying a composition as provided herein to an exterior epithelial surface of a human body at least daily for a period of at least 1 week. In one or more related embodiments, the condition or disease is a dermatological condition or disease, and the applying step comprises applying the topical composition to the skin once or twice daily for a period of from about 6 to about 52 weeks.

In one or more additional embodiments, the dermatological condition or disease is acne or rosacea. In one or more particular embodiments, the acne is acne vulgaris. In yet or more alternative embodiments, the acne is acne fulminans.

In one or more further embodiments related to a method for treating a subject having acne, the method is effective to reduce the inflammatory lesion count by at least 50% or at least 70% when applied daily for a period of from about 6 to about 52 weeks. In one or more embodiments, the method is effective to result in at least a 2-point reduction in acne intensity score according to the Investigator's Global Assessment (IGA) scale ("Guidance for Industry: Acne Vulgaris: Developing Drugs for Treatment", U.S. Department of Health and Human Services, Food and Drug Administration, September 2005) when the composition is topically applied daily for 6-52 weeks to a human with an initial acne intensity score of in the range of 3 to 4, or in the range of 2 to 4. The method is effective in meeting the above requirement if, at any point during the 6-52 weeks of daily application, the inflammatory lesion count is reduced by at least about 50%.

In one or more further embodiments, a method of topically administering a composition as provided herein, or a method of treating a disease or condition as provided herein, results in no increase, or a negligible increase, or a clinically insignificant increase, in the subject's blood plasma level of the drug upon topical application of a single dose of the composition to a human subject, where the single dose is applied to the subject's entire face and the blood plasma level of the tetracycline class drug is measured one hour post topical administration.

In yet one or more further embodiments, provided is a composition as described herein accompanied by instructions for topical use for treatment of a dermatological condition or disease of the skin. In one or more related embodiments, the instructions comprise instructions for applying the composition to an external skin surface from one to three times daily for a period of from about 2 weeks to at least about 6 weeks or until a visible improvement in the dermatological condition or disease is observed.

In yet an additional aspect, provided herein is a method for making a composition, e.g., one suitable for treating acne in a human, preferably a topical composition, the method comprising (i) combining a tetracycline-class drug or salt or solvate thereof, a source of magnesium, a volatile monohydric aliphatic alcohol, and a polyol to form a mixture, and (ii) agitating the mixture from (i) to form a solution.

In yet another aspect, provided is a method for making a composition, the method comprising (i) combining minocycline, a magnesium salt, and a sulfite compound in a non-aqueous solvent to form a mixture, and (ii) agitating the mixture from (i) to form a solution in which the minocycline is dissolved.

Each of the foregoing aspects and embodiments is meant to apply to each and every other aspect and embodiment. Additional embodiments of the composition, related methods, components of the composition, and the like will be apparent from the following description, examples, figures and claims. These and other objects and features of the disclosure will become more fully apparent when read in conjunction with the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A provides data for compositions comprising 1% cineole. FIG. 1B provides data for compositions absent cineole.

FIGS. 2A and 2B are graphs illustrating the relative concentrations of 4-epi-minocycline and minocycline, respectively, over time for compositions with 1% cineole. FIGS. 2C and 2D are graphs are graphs illustrating the relative concentrations of 4-epi-minocycline and minocycline, respectively, over time for compositions without cineole.

FIG. 4A is a hematoxylin and eosin (H&E) stained cross section of the skin. FIGS. 4B and 4C are images based upon MALDI-TOF mass spectrometry data indicating the location of minocycline and sebum within the skin for sections sliced from tissue in approximately the same shape as shown in FIG. 4A.

FIG. 5A is an H&E stained cross section of the skin following application of the topical composition described in Example 6. FIGS. 5B and 5C are images based upon MALDI-TOF mass spectrometry data indicating the location of minocycline and sebum within the skin for sections sliced from tissue in approximately the same shape as shown in FIG. 5A.

FIG. 7A shows a section of human tissue to which no topical composition was applied. FIGS. 7B and 7C show sections of human tissue to which topical compositions comprising approximately 1% and 4% (w/w) minocycline free-base-equivalent, respectively, were applied.

FIGS. 9A and 9B illustrate minocycline amounts ($\mu g/cm^2$) measured by HPLC in ex vivo human facial skin for formulations containing 1% and 4% minocycline, respectively, as described in Example 12. Time points tested were 2 and 4 hours for intact and epimerized minocycline. Data presents the mean of the donors±SE (*P≤0.05 between the hydrophilic and lipophilic formulations for both FIGS. 9A and B).

DETAILED DESCRIPTION

Figure 1A:
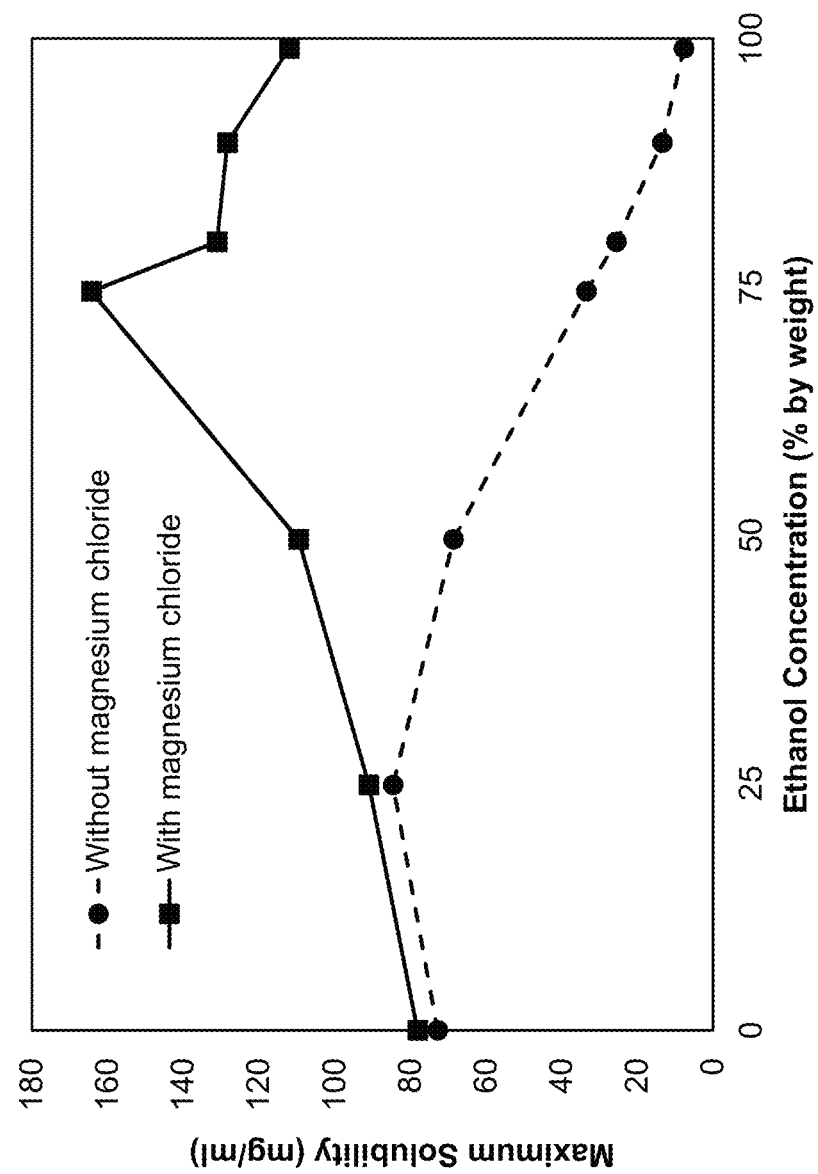
FIGS. 1A-B are graphs indicating the maximum solubility of minocycline hydrochloride in liquid compositions comprising varying ratios of ethanol and propylene glycol as a function of the concentration of ethanol in the composition as described in Example 1. The dashed line represents solubilities of minocycline hydrochloride in liquid compositions without magnesium chloride. The solid line represents solubilities of minocycline hydrochloride for similar liquid compositions with magnesium chloride (anhydrous).

The present invention will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As can be appreciated from the foregoing and following description, each and every feature described herein, and each and every combination of two or more of such features, is included within the scope of the present disclosure provided that the features included in that such combinations are not inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

All publications, patents and patent applications cited herein are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document that are incorporated herein by reference.

Definitions

It must be noted that, as used in this specification, the singular forms "a," "an," and "the" include plural referents unless the context clearly dictates otherwise. Thus, for example, reference to an "active ingredient" includes a single ingredient as well as two or more different ingredients, reference to a "solvent" refers to a single solvent as well as to two or more different solvents or a complex mixture of solvents, reference to an "magnesium salt" includes a single magnesium salt as well as two or more different magnesium salts, and the like.

In describing and claiming the present invention, the following terminology will be used in accordance with the definitions described below.

The term "topical composition" refers to a material that comprises pharmaceutically acceptable ingredients, including an active pharmaceutical ingredient (API), and is intended for administration to an animal or human subject and is applied to the surface of the skin, in contrast to materials that are taken orally or via intravenous (subdermal) injection. A topical composition is generally intended to have its intended effect at the site of application and does not result in significant concentrations of drug in the bloodstream or other tissues (as is the case with, for example, transdermal compositions). Topical compositions as provided herein are typically administered for the purpose of alleviation of symptoms associated with a dermatological disease or condition, treatment of a dermatological disease or condition, or prevention of a dermatological disease or condition.

The term "solvent" refers to a substance in which one or more solid ingredients are dissolved to some extent. For example, ethanol, isopropanol, and propylene glycol, to name a few, are considered as solvents for minocycline.

The term "tetracycline-class drug" refers to tetracycline and tetracycline derivatives such as, for example, minocycline, doxycycline, oxytetracycline, and their corresponding pharmaceutically acceptable salt forms, as well as solvates and hydrates thereof, including various crystalline forms, polymorphs, amorphous materials, etc. A tetracycline antibiotic generally contains a four ring octahydrotetracene-2-carboxamide skeleton, while the actual substituents on the skeleton may vary.

The term "minocycline" refers to (4S,4aS,5aR,12aR)-4,7-bis(dimethylamino)-1,10,11,12a-tetrahydroxy-3,12-dioxo-4a,5,5a,6-tetrahydro-4H-tetracene-2-carboxamide (i.e. CAS number 10118-90-8) and its corresponding pharmaceutically acceptable salt forms, as well as solvates and hydrates thereof. Exemplary forms of minocycline are commonly identified by their CAS numbers. For example, minocycline hydrochloride has a CAS number of 13614-98-7.

The term "monohydric aliphatic alcohol" refers to a monofunctional organic compound that contains a single hydroxyl group, in which the hydroxyl functional group is covalently attached to a saturated carbon atom forming part of a branched or linear alkyl chain, and which does not contain an aromatic-ring configuration of atoms. Generally, a monohydric aliphatic alcohol for use in the compositions provided herein conforms to the formula R—OH, where R is a $C_1$-$C_4$ alkyl. Suitable R groups include ethyl, propyl, isopropyl, butyl, sec-butyl, isobutyl and tert-butyl.

The term "polyol" refers to a pharmaceutically acceptable alcohol containing two or more hydroxyl groups, and possessing from 3-8 carbon atoms. Polyols suitable for use in the instant compositions may but do not necessarily contain functional groups in addition to the hydroxyl groups, such as e.g., an ether bond. As used herein, polyethylene glycol shall not be considered to be a polyol. Illustrative polyols include diols such as propylene glycol (PG) and dipropylene glycol, triols such as glycerol, 1,2,6 hexanetriol, trimethylolpropane, and higher alcohols (i.e., containing more than 3 hydroxyl groups) such as sorbitol and pentaerythritol. Polyols also include butylene glycol, hexylene glycol, 1,6 hexanediol, mannitol, and xylitol. It is recognized that some of these solvents are solids that may be undesirable, but when combined in appropriate mixtures, they may be suitable for use in a topical composition as described herein.

The term "cineole" refers to 1,8-cineole.

The term "cosmetic" refers to an item that is an "article intended to be rubbed, poured, sprinkled, or sprayed on, introduced into, or otherwise applied to the human body for cleansing, beautifying, promoting attractiveness, or altering the appearance" (from U.S. FD&C Act, section 201(i)). The U.S. Food and Drug Administration classifies various items as cosmetics or drugs. This definition is intended to follow the U.S. FDA classifications. U.S. FDA further clarifies on its web site that "Among the products included in this definition are skin moisturizers, perfumes, lipsticks, fingernail polishes, eye and facial makeup preparations, cleansing shampoos, permanent waves, hair colors, and deodorants, as well as any substance intended for use as a component of a cosmetic product."

The term "topical", in reference to administration of a drug or composition, refers to application of such drug or composition to an exterior epithelial surface of the body, including the skin or cornea. For purposes of this application, applications inside a bodily orifice, such as the mouth, nose, or ear shall not be considered to be topical applications.

A solvent (or solvents) is said to "dissolve" a tetracycline class drug (or conversely, the drug is said to be soluble in a solvent) if the solubility of that drug as measured in Example 1 at 25° C. is at least 0.1% (w/w). For emulsions and the like, the drug is only considered to "dissolve" in the solvent if the drug is in direct interaction with the solvent such that the drug is incorporated into the solvent to form a solution. So, for example, a drug that is coated to limit interaction with a solvent would not be considered dissolved in that solvent if it remained in particulate form.

A solvent or composition is said to be "anhydrous" if there is no added water in the solvent or composition. That is to say, as used herein, an anhydrous composition is one in which water has not been added as a component. For clarity, a solution or composition can be considered to be anhydrous even if it contains water arising from a composition component, such as through the addition of minocycline hydrochloride hydrate, as long as no free water is added to the composition. Many of the solvents described herein are hydroscopic to a greater or lesser extent and such solvents may be part of an anhydrous compositions without regards to the water that is naturally absorbed by such materials.

A solvent or composition is said to be "non-aqueous" if there is less than 5% by weight water content in the solvent or composition, respectively, as measured by Karl Fischer titration or other suitable method.

A solvent or composition is said to be "volatile" if it has a boiling point of less than 100° C. at atmospheric pressure. Volatile solvents or compositions typically evaporate readily at room temperature and atmospheric pressure. Examples of volatile solvents include isopropanol, ethanol, and t-butyl alcohol. Examples of non-volatile solvents include water, white petrolatum, and olive oil.

A drug is said to be "stabilized" by the presence of a particular material contained in a composition, if a composition comprising all of the same materials in the same relative proportions to each other, excluding the active ingredient or drug, but with the particular material removed, exhibits a loss in potency that is greater than the loss of potency for the original composition when stored at 25° C. and 60% relative humidity in a dark environment when measured at a 6 month time point. For clarity, when performing the replacement (i.e., assessment of stability enhancement), the weight percentage of the drug in the composition is not increased, but instead the removed material is effectively replaced by equivalent proportions from the rest of the composition excluding the drug. For example, if a composition containing 30% (w/w) A, 30% (w/w) B, 20% (w/w) C, 10% (w/w) D and 10% (w/w) E is evaluated for the effect of component A, and E is the active ingredient (i.e., tetracycline-class drug), the comparative composition will contain 0% (w/w) A (the excluded component), 45% (w/w) B, 30% (w/w) C, 15% (w/w) D, and 10% (w/w) E (the active ingredient).

The term "efficiency of penetration" refers to the percentage of the tetracycline class drug that penetrates beyond the first few layers of stratum corneum (i.e. after removal of upper stratum corneum layers by two sequential tape strippings) following application of the composition to an ex vivo portion of human skin tissue when approximately 12 mg/cm$^2$ of the composition is applied to the skin surface for 4 hours as described in Example 4.

"MIC" or minimum inhibitory concentration is defined as the lowest concentration of an antimicrobial compound that will inhibit the visible growth of a microorganism after 48 hours of incubation.

The abbreviation "(w/w)" indicates that relative concentrations of components in a composition are presented on a "weight for weight" basis (i.e. percentages refer to a percentage of the total weight), rather than on the basis of volume or some other basis. In reference to a solvate or hydrate of a tetracycline-class drug, e.g., minocycline, weight percentages should be weight corrected to account for mass pertaining to solvent/or hydrate molecules contained in the drug source. For example, a composition comprising 1.16% (w/w) minocycline hydrochloride dihydrate composition is equivalent to 1% minocycline free-base-equivalent based on ratios of the molecular weights of minocycline free base (457.48) and minocycline hydrochloride dihydrate (529.97).

The term "relative concentration" in reference to a tetracycline class drug is typically determined by HPLC measurement, and corresponds to the peak area of the active tetracycline class drug divided by the sum of the peak areas for all peaks of the HPLC chromatogram for times following elution of the solvent peaks. For clarity, the intent of this measurement is that the HPLC chromatogram omits the peak areas for each of the solvent peaks and includes each of the peaks that are due to the tetracycline class drug and its detected key degradation components. For example, the relative concentration of active minocycline was measured for each of the compositions described in Example 19.

The term "relative concentration" in reference to an epimer of a tetracycline class drug is typically determined by HPLC measurement and corresponds to the peak area of an epimer(s) of the active tetracycline class drug divided by the sum of the peak area for the epimer and the peak area for the active tetracycline class drug. For example, the relative concentration of 4-epi-minocycline was measured for each of the compositions described in Example 19.

The term "concentration" in reference to a tetracycline class drug is typically determined by HPLC measurement, and corresponds to the peak area of the active tetracycline class drug multiplied by the concentration of the active tetracycline class drug in the working standard and divided by the peak area of the active tetracycline drug for a working standard containing a known amount of the active tetracycline drug. For example, the concentration of minocycline was measured for each of the compositions described in Example 20.

The term "closed," such as in regards to a "closed vial," refers to a vial that is sealed against the significant loss of solvent or other materials from the vial by evaporation. For the Examples described herein, closed glass vials refer to borosilicate glass vials closed with a polyethylene cone-lined phenolic cap and sealed with parafilm. The compositions within the glass vials were protected from light, either by using amber glass vials or by wrapping the vials with aluminum foil.

The term "viscosity" refers to the measurement of a substance using a viscometer, such as a Brookfield LVF viscometer (Brookfield Engineering Laboratories, Inc., Middleboro, Mass.) or equivalent, with spindle and speed combinations suitable for the testing of applicable viscosity level.

As used herein, "dermatological condition" refers to cosmetic and pathological disorders of the skin. Dermatological conditions include topical inflammatory skin conditions such as eczema, seborrhoeic dermatitis, bullous dermatoses, cutaneous sarcoidosis, Kaposi's sarcoma, neutrophilic dermatoses, contact dermatitis, rosacea, psoriasis and acne including acne rosacea, and infections such as Impetigo, cellulitis, erysipelas, folliculitis, furuncles, carbuncles, Lyme disease, and other skin infections.

As used herein, "acne" is a disorder of the skin characterized by papules, pustules, cysts, nodules, comedones, and other blemishes or skin lesions. These blemishes and lesions are often accompanied by inflammation of the skin glands and pilosebaceous follicles, as well as, microbial, especially bacterial, infection. As used herein, acne includes all known types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea. Acne rosacea is characterized by inflammatory lesions (erythema) and telangiectasia. Telangiectasia is abnormally and permanently dilated blood vessels associated with a number of diseases. For example, facial telangiectasia is associated with age, acne rosacea, sun exposure, and alcohol use.

The term "pharmaceutically acceptable" in reference to an entity or ingredient is one that may be included in the compositions provided herein and that causes no significant adverse toxicological effects in the patient at specified levels, or if levels are not specified, in levels known to be acceptable by those skilled in the art. All ingredients in the compositions described herein are provided at levels that are pharmaceutically acceptable. For clarity, active ingredients may cause one or more side effects and inclusion of the ingredients with a side effect profile that is acceptable from a regulatory perspective for such ingredients will be deemed to be "pharmaceutically acceptable" levels of those ingredients.

"Pharmaceutically acceptable salt" denotes a salt form of a drug or active ingredient having at least one group suitable for salt formation that causes no significant adverse toxicological effects to the patient. Reference to an active ingredient as provided herein is meant to encompass its pharmaceutically acceptable salts, as well as solvates and hydrates thereof. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate, phosphate, and the like. Suitable pharmaceutically acceptable salt forms and methods for identifying such salts are found in, e.g., Handbook of Pharmaceutical Salts: Properties, Selection and Use, Weinheim/Zürich:Wiley-VCH/VHCA, 2008; P. H. Stahl and C. G. Wermuth, Eds.

"Non-irritating" in reference to a topical formulation as provided herein refers to a formulation having an average score of less than 0.50 on the modified Draize scale for a test of 5 or more Sprague-Dawley rats. The modified Draize test is an acute irritation test carried out as follows. A Sprague-Dawley rat is shaved in an application area, and the application area allowed to rest for approximately 24 hours and then rinsed with non-irritating soap. A test composition is applied evenly, without significant rubbing, to a 10 cm$^2$ area of the rat's skin in a volume of 2.5 mg/cm$^2$. The sample is allowed to sit uncovered for 24 hours. After 24 hours, the application area is washed gently with 1× phosphate buffered saline (1×PBS) and non-irritating soap to facilitate observation of the application area. The application area is then scored according to the following scale: 0=no evidence of irritation; 1=minimal erythema, barely perceptible; 2=definite erythema, readily visible, minimal edema or minimal popular response; 3=erythema and papules; 4=definite edema; 5=erythema, edema, and papules; 6=vesicular eruption; 7=strong reaction spreading beyond test site.

"Therapeutically effective amount" is used herein to mean the amount of a pharmaceutical preparation, or amount of an active ingredient in the pharmaceutical preparation, that is needed to provide a desired level of active ingredient in a target tissue or at a target site. The precise amount will depend upon numerous factors, e.g., the particular active ingredient, the components and physical characteristics of the pharmaceutical preparation, intended patient population, patient considerations, and the like, and can readily be determined by one skilled in the art, based upon the information provided herein and available in the relevant literature.

Room temperature refers to a temperature in a range of about 20-25° C. In reference to a measurement or other feature requiring a precise indication of room temperature, room temperature is taken as 25° C.

The term "patient" refers to a living organism suffering from or prone to a condition that can be prevented or treated by administration of a composition as provided herein, and includes both humans and animals. Preferred animals are mammals.

"Optional" or "optionally" means that the subsequently described circumstance may or may not occur, so that the description includes instances where the circumstance occurs and instances where it does not.

In many cases, the patent application describes ranges of values. Such ranges shall be construed to include the endpoints of the range unless doing so would be inconsistent with the text or otherwise noted.

Overview

The instant disclosure addresses at least some of the problems previously identified herein, e.g., in the Background section, related to topical compositions comprising a tetracycline class drug. After several composition attempts, the Applicants have discovered a composition and related solvent system that promotes the penetration of a tetracycline class drug into the skin and in which such a drug has high solubility. In such a solvent system, the drug ideally remains in solution as the solvent penetrates into the skin. As has been recognized by the Applicants, if some of the solvent is lost to evaporation prior to penetration, the concentration of the drug in the solvent on the skin surface will typically be increased, which means that the solubility of the drug within the composition is an important feature for consideration in designing an improved topical composition comprising a tetracycline class compound. Additionally, as has been discovered by the Applicants, selecting a solvent in which the drug is fully dissolved during storage reduces or eliminates variations in drug concentration throughout the composition. In the description that follows, minocycline is often referred to as the exemplary tetracycline class compound, however, the compositions and methods disclosed herein also apply to tetracycline class compounds other than minocycline. Additionally, a liquid composition comprising a tetracycline-class and having superior stability is also provided herein.

The present application provides a topical composition and related methods for preparing the topical composition. In one aspect, the topical composition comprises minocycline, a magnesium salt, and a sulfite compound in a non-aqueous solvent, where details regarding the minocycline (an exemplary tetracycline), the magnesium salt and the sulfite compound are provided above and in the sections which follow. It has been discovered that liquid compositions such as provided herein, e.g., comprising minocycline and a magnesium salt in a non-aqueous solvent system (preferably a hydrophilic solvent system), comprising a sulfite-based antioxidant are notably and advantageously more stable than those compositions comprising non-sulfite anti-oxidants. See, e.g., Example 19. Surprisingly, such compositions demonstrated significantly less degradation of minocycline over time when compared to counterpart formulations comprising non-sulfite-based anti-oxidants. Such formulations also exhibited prolonged stability with respect to color, i.e., exhibited no significant change in color upon storage.

In another aspect, provided herein is a topical composition comprising a tetracycline-class drug, a source of magnesium, a monohydric aliphatic alcohol, and a polyol, wherein (i) the ratio between the monohydric aliphatic alcohol and the polyol is in the range of 1:1 to 99:1 by weight and (ii) the tetracycline-class drug is dissolved within the topical composition. In some exemplary embodiments, the monohydric aliphatic alcohol is ethanol, isopropanol, or tert-butyl alcohol (i.e., t-butyl alcohol). In one or more additional exemplary embodiments, the polyol is a C3-C8 aliphatic, saturated diol or triol. In one or more further embodiments, the polyol is a 1,2-diol, a 1,3-diol or a triol. Illustrative polyols include propylene glycol, dipropylene glycol, and glycerol. Further details of the composition and related methods are provided herein.

The Applicants have discovered that the combination of a tetracycline class drug, a source of magnesium, a monohydric aliphatic alcohol, and a polyol forms a eutectic within a composition such that the melting point for the composition after evaporating the solvent as measured by differential scanning calorimetry (DSC) is decreased relative to that of the composition absent one of these four components. The Applicants have also discovered that the solubility of minocycline in the composition is decreased relative to the solubility of minocycline for the composition without one of the three non-drug components. Based on solubility and DSC measurements, it is believed that these four components can form a unique ionic interaction or non-specific binding that has synergistic properties for use in a topical composition. These synergistic properties may require all four components for optimal solubilization benefit. Without being bound by theory, it appears that the solvent mixture neutralizes the ionic charge in the minocycline-magnesium complex, which increases the solubility of the minocycline in the solvent mixture relative to the solubility of minocycline in either solvent independently.

In one or more embodiments, the monohydric aliphatic alcohol is volatile, the polyol is non-volatile, and the tetracycline-class drug remains soluble in the composition even when the monohydric aliphatic alcohol is omitted or removed from the composition, or its concentration is reduced, such as through evaporation. In such embodiments, a favorable balance is achieved between the stabilizing effect of the volatile monohydric aliphatic alcohol or the non-aqueous solvent on the composition (e.g., during storage), and the persistent solubility of the drug both in the composition and when applied to the skin, even upon evaporation of some or all of the volatile monohydric aliphatic alcohol, when present. This approach can be advantageous because 1) the volatile monohydric aliphatic alcohol appears to stabilize the composition and 2) the polyol maintains the tetracycline class drug in a dissolved state for a prolonged duration on the skin, thus allowing more time for enhanced permeation than if the monohydric aliphatic alcohol replaced the polyol. Relative weight percentages of each of the volatile monohydric aliphatic alcohol, the relatively non-volatile polyol and the tetracycline class drug in the composition, effective to achieve a balance of prolonged storage stability and maintained solubility of tetracycline class drug when applied to the skin, are provided herein.

In some embodiments, the composition is used for the treatment of a dermatological condition or disease. Non-limiting examples of dermatological conditions or diseases for which the composition may be used include but are not limited to acne, rosacea, seborrhoeic dermatitis, psoriasis, and superficial skin infections such as impetigo, as well as in wound management.

The Composition

As described above, in one aspect, the topical composition comprises minocycline, a magnesium salt, and a sulfite compound in a non-aqueous solvent. In yet another aspect, the composition comprises a tetracycline class drug, a source of magnesium, a monohydric aliphatic alcohol, and a polyol. Composition components and features will now be described in greater detail.

Tetracycline class drugs include for example tetracycline and tetracycline derivatives such as demeclocycline, minocycline, doxycycline, oxytetracycline, and their corresponding pharmaceutically acceptable salt forms, as well as solvates and hydrates thereof. The tetracycline class drug may also be a fluorocycline, i.e., a 7-fluoro-9-substituted-6-demethyl-6-deoxytetracycline, such as eravacycline (TP-434) or 7-fluoro-9-pyrrolidinoacetamido-6-demethyl-6-deoxytetracycline. Drugs belonging to the tetracycline class generally contain a four ring octahydrotetracene-2-carboxamide skeleton, while the actual substituents on the skeleton may vary. Tetracyclines are broad spectrum antibiotics, exhibiting activity against a broad range of bacteria. One preferred tetracycline for use in the compositions provided herein is minocycline. Minocycline is a potent semi-synthetic tetracycline with activity against a wide range of gram-positive and gram-negative organisms. Minocycline presents a broader spectrum when compared to other tetracycline-type compounds, and is also the most lipid-soluble of the tetracyclines, i.e., can more readily penetrate into various tissues when compared to other tetracyclines. This feature presents an added challenge for topically administering minocycline, especially in free base form, due to its proclivity in comparison to other tetracyclines for transport across the epidermis. The compositions provided herein may contain minocycline or any or the tetracycline antibiotics in any available form, e.g., as the free base, as a hydrochloride or other pharmaceutically acceptable salt, including all crystalline polymorphs, solvates, hydrates, or amorphous forms thereof. In one or more preferred embodiments, the minocycline or minocycline salt is not in the form of a hydrate (i.e., is in non-hydrated form). However, in some instances, the tetracycline drug may be in a hydrated form, e.g., comprising less than about 20 weight percent water. In some preferred embodiments, the tetracycline drug will comprise less than about 5% by weight water, or may comprise less than about 2% by weight water.

The amount of tetracycline class drug in the topical composition (e.g., minocycline) typically ranges from about 0.01% to about 10% by weight, or from about 0.1% to about 5% by weight. Illustrative ranges are from about 0.1% to about 4% by weight, or from about 0.2% to about 3% by weight or from about 0.2% to about 1.5% by weight. For example, the topical formulation may comprise any one of the following weight percentages of minocycline: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 1.0%, 2.1%, 2.2%, 2.3%, 2.4%, 2.5% and so forth.

The topical composition also comprises a source of magnesium, typically in the form of a magnesium salt. Illustrative magnesium salts include but are not limited to magnesium bromide, magnesium chloride, magnesium fluoride, magnesium iodide, magnesium sulfate, magnesium salicylate, and magnesium phosphate. Magnesium salts are often supplied commercially as hydrates, and hydrates can be used in the instant formulations. However, in some preferred embodiments, the magnesium salt is anhydrous, due to the instability of tetracycline-class drugs such as minocycline in the presence of water. See, for instance, Example 20. In some preferred embodiments, the source of magnesium comprises a magnesium salt having a counter-ion that is a soft (polarizable) ion, such as chloride or iodide, rather than a hard ion, such as sulfate or fluoride. In some further embodiments, the source of magnesium comprises a magnesium salt having a counter-ion that is chloride or is softer than a chloride ion. In some further embodiments, the source of magnesium comprises a magnesium salt having a counter-ion that is an acetate ion ($CH_3COO^-$) or is softer than an acetate ion.

Hard/Soft Acid/Base (HSAB) theory grades acids and bases on a scale from hard to soft. Using a soft ion lowers the interfacial tension within the mixture and thus enhances solubility. Factors that contribute to an ion being classified as "soft" include large size, low charge states, and strong polarizability. Additional details of HSAB theory are described in Pearson, Ralph G. "Hard and Soft Acids and Bases". *J. Am. Chem. Soc.* 1963; 85 (22): 3533-9 and Pearson, R. G. "Recent Advances in the Concept of Hard and Soft Acids and Bases." *J. Chem. Education*. July 1987, 64 (7): 561-7, which are herein incorporated by reference.

As described in Example 1, the presence of a magnesium salt in the composition is effective to increase the solubility of the tetracycline class drug, e.g., minocycline, in the instant compositions to a notable degree. See, e.g. FIG. 1A. Without being bound by theory, the magnesium appears to interact with the minocycline in the composition, as evidenced by its impact on the MIC value when compared to the MIC value of minocycline alone. See, e.g., Example 5, which describes MIC measurements for minocycline, anhydrous magnesium chloride, and a 1:1.5 w/w mixture of the two. Minocycline alone exhibited a MIC of 0.125 micrograms per milliliter while the combination possessed a higher MIC of 0.5 microliters—a four-fold increase (meaning that the combination was four times less active than the minocycline alone). Thus, even accounting for differences in weight in the combination, the results indicate that the magnesium is interacting with the minocycline. Analytical techniques were used to confirm that the observed loss in antimicrobial activity was not due to degradation of the minocycline.

Typical amounts of a source of magnesium, e.g., a magnesium salt, in the topical compositions provided herein range from about 0.2-10% by weight. Molar ratios of the magnesium source to the tetracycline class drug, e.g., minocycline, range from about 2:1 to about 100:1. Illustrative molar ratios are typically at least about 2:1 (Mg:tetracycline drug). For example, suitable molar ratios are about 2:1, about 2.5:1, about 3:1, about 3.5:1, about 4:1, about 4.5:1, about 5:1, about 5:1, about 5.5:1, about 6:1, about 6.5:1, about 7:1, about 7.5:1, about 8:1, about 8.5:1, about 9:1, about 9.5:1, and about 10:1. Relative amounts of the source of magnesium to the tetracycline class drug in the topical composition on a weight/weight (w/w) basis will typically range from about 1:3 to about 3:1, but ranges larger or smaller than this may be used depending on the molecular weights of the source of magnesium and the form of the tetracycline class drug. Thus, the relative amount by weight of the source of magnesium to the weight of the minocycline hydrochloride (i.e., a tetracycline class drug) can include any one or more of the following: 0.4 (i.e., the amount by weight of magnesium 0.4 times that of the minocycline component) 0.5, 0.6, 0.7, 0.8, 0.9, 1.0 (i.e., equal weight amounts), about 1.5, about 2, about 2.5, about 3 times, about 3.5 times, about 4 times. about 4.5 times, about 5 times, about 5.5 times, about 6 times, about 6.5 times, about 7 times, about 7.5 times, about 8 times, about 8.5 times, about 9 times, about 9.5 times, or about 10 times, including any and all ranges falling within any two of the foregoing values. Typically, the magnesium source, e.g., the magnesium salt, is present in molar excess relative to the minocycline. Based upon the examples provided herewith, it can be seen that the magnesium salt is effective to stabilize the instant compositions.

Alternatively, or in addition to a magnesium salt, the topical formulation may comprise a salt of a divalent metal cation such as, for example, calcium, aluminum, zinc, where illustrative counter-ions and relative amounts (e.g., for total divalent metal ion) are as described above for a magnesium salt. Preferred divalent metal ions are those capable of interaction with minocycline.

The topical composition generally additionally comprises, as part of its non-aqueous solvent system, a monohydric aliphatic alcohol, preferably a volatile alcohol. Generally, a monohydric aliphatic alcohol for use in the compositions provided herein conforms to the formula R—OH, where R is a $C_1$-$C_4$ alkyl group. Suitable R groups include methyl, ethyl, propyl, isopropyl, butyl, sec-butyl, isobutyl and tert-butyl. Preferably, the monohydric aliphatic alcohol is a primary alcohol such as ethyl alcohol, propyl alcohol or butyl alcohol. One particularly preferred monohydric aliphatic alcohol is ethanol. In some embodiments, the monohydric aliphatic alcohol is one having a solubility in water of 5 percent or greater. Methanol, ethanol, 1- and 2-propanol, and t-butyl alcohol, for example, are miscible with water, while 1-butanol has a solubility of about 9% in water and 2-butaol has a solubility in water of 7.7%. Preferred alcohols are hydrophilic.

Yet a further component of the topical composition (i.e., forming part of its solvent system) may be a polyol containing two or more hydroxyl groups, and possessing from 3-8 carbon atoms. Typically, the polyol is an aliphatic compound; polyols for use in the instant composition include diols such as propylene glycol (PG, propane-1,2-diol), hexylene glycol (2-methylpentane-2,4-diol), 1,3-butylene glycol (1,3-butane diol), and dipropylene glycol, triols such as glycerol and trimethylolpropane, and higher alcohols (meaning containing more than 3 hydroxyl groups) such as sorbitol and pentaerythritol. Preferred polyols are C3-C8 diols and triols. The diol or triol will typically have a molecular weight less than about 250, or even less than about 200. In some instances, the polyol will have a molecular weight less than about 125. The polyol, may, in some instances, be hygroscopic, such as in the case of propylene glycol. In some embodiments, the polyol is a triol other than glycerol or glycerin.

Many monohydric aliphatic alcohols, such as ethanol, can provide a stable solvent for tetracycline class drugs, however tetracycline class drugs have limited solubility in mixtures of ethanol and propylene glycol. Additionally, since ethanol is a volatile solvent, much of the solvent evaporates quickly when applied to the skin. This evaporation quickly increases the concentration of the tetracycline class drug on the surface of the skin and can lead to formation of solid deposits on the skin surface or in the upper layers of the skin, neither of which is desirable, particularly due to the potential for staining and/or skin pigmentation. The compositions provided herein are aimed, at least in part, in overcoming the shortcomings noted above. For example, consider a composition comprising 1.2% (w/w) minocycline hydrochloride (approximately 1% (w/w) minocycline free-base-equivalent), 1.2% (w/w) magnesium chloride, 77.6% (w/w) ethanol, and 20% (w/w) propylene glycol. The ethanol is much more volatile than the propylene glycol, such that even if all of the ethanol evaporates from the skin, the concentration of the minocycline free-base-equivalent in the residual composition following evaporation of ethanol would be approximately 4.5%. Considering that minocycline, when combined with magnesium chloride, is soluble in propylene glycol at levels up to approximately 7-8% minocycline free-base-equivalent (depending on temperature), this means that in the foregoing example, the minocycline will desirably remain in solution (i.e., in a dissolved state), especially at the elevated temperature of the skin. Moreover, the concentration of minocycline in the residual composition would be less than that described in this calculation, as some of the ethanol would transport minocycline into the skin rather than evaporating.

Exemplary compositions as provided herein will generally comprise a greater percent by weight of the monohydric aliphatic alcohol in comparison to the polyol. For example, advantageous compositions as described herein may comprise from about 50% (w/w) to about 95% (w/w) monohydric aliphatic alcohol, from about 5% (w/w) to about 40% (w/w) polyol, from about 0.1% (w/w) to about 10% (w/w) tetracycline class drug, and from about 0.2% (w/w) to about 15% (w/w) magnesium source. Some preferred compositions as described herein may comprise from about 60% (w/w) to about 90% (w/w) monohydric aliphatic alcohol, from about 5% (w/w) to about 35% (w/w) polyol, from about 0.2% (w/w) to about 5% (w/w) tetracycline class drug, and from about 0.2% (w/w) to about 10% (w/w) magnesium source.

Illustrative liquid compositions may contain, for example, any one or more of the following weight-weight percentages of monohydric aliphatic alcohol, including ranges between each of the following values: 50%, 55%, 60%, 65%, 70%, 75%, 80%, 85%, 90% or 95% alcohol, where preferably, the weight percent alcohol is greater than the weight percent polyol. Further representative ranges for the alcohol component, which may be combined with w/w amounts or ranges for the tetracycline drug and other formulation components as provided herein are from: 50-55% w/w, 50-60% w/w, 50-65% w/w, 50-70% w/w, 50-75% w/w, 50-80% w/w, 50-85% w/w, 50-90% w/w, 50-55% w/w, 55-60% w/w, 55-65% w/w, 55-70% w/w, 55-75% w/w, 55-80% w/w, 55-85% w/w, 55-90% w/w, 55-95% w/w, 60-65% w/w, 60-70% w/w, 60-75% w/w, 60-80% w/w, 60-85% w/w; 60-90% w/w, 60-95% w/w, 65-70% w/w, 65-75% w/w, 65-80% w/w, 65-85% w/w; 65-90% w/w, 65-95% w/w, 70-75% w/w, 70-80% w/w, 70-85% w/w, 70-90% w/w, 70-95% w/w, 75-80% w/w, 75-85% w/w, 75-90% w/w, 75-95% w/w, 80-85% w/w, 80-95% w/w, 80-95% w/w, 85-90% w/w, 85-95% w/w, 90-95% w/w.

Representative amounts of a polyol component, include, any one or more of the following: 5%, 10%, 15%, 20%, 25% 30%, 35% or 40% (w/w), including ranges between each of the foregoing, such as, for example: 5%-10% w/w, 5-15% w/w, 5-20% w/w, 5-30% w/w, 5-35% w/w, 5-40% w/w, 10-15% w/w, 10-20% w/w, 10-25% w/w, 10-30% w/w, 10-35% w/w, 10-40% w/w, 15-20% w/w, 15-25% w/w, 15-30% w/w, 15-35% w/w, 15-40% w/w, 20-25% w/w, 20-30% w/w, 20-35% w/w, 20-40% w/w; 25-30% w/w, 25-35% w/w, 25-40% w/w, 30-35% w/w, 30-40% w/w, or 35-40% w/w.

Generally, the ratio between the monohydric aliphatic alcohol and the polyol is in a range of 1:1 to 99:1 by weight. As set forth above, the composition will generally comprise a greater percent by weight of the monohydric aliphatic alcohol in comparison to the polyol. Exemplary w/w ratios of alcohol to polyol include, for example, about 1:1, 1.5:1, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, and 95:1. The composition may comprise a w/w ratio between the monohydric aliphatic alcohol and the polyol between about 1:1 to 20:1, or from about 1:1 to about 15:1, or from about 1:1 to about 10:1, or from about 2:1 to about 20:1, or from about 2:1 to about 10:1, or from about 2:1 to about 7:1.

In certain embodiments, the composition does not comprise a hydrophobic oil or wax. In some other embodiments, the composition does not comprise a fatty acid and/or a fatty acid derivative. In some embodiments, the liquid formulation is absent a foaming agent.

The instant compositions may also contain relatively small amounts, e.g., less than about 10% (w/w) of one or more auxiliary excipients suitable for topical use including but not limited to pH modifying agents, preservatives, thickening agents, gel-forming agents, emulsifying agents, antioxidants, scent agents, and the like. Compounds suitable for incorporation may be found, e.g., in R. C. Rowe, et al., *Handbook of Pharmaceutical Excipients* (4$^{th}$ Ed.), Pharmaceutical Press, London, 2003.

Gelling agents which may be used in the topical compositions include conventional gelling agents well known for their gelling properties, such as, for example, cellulose ethers such as hydroxypropyl cellulose, hydroxypropyl methylcellulose, carboxymethyl cellulose, sodium carboxymethyl cellulose, hydroxyethyl cellulose, and the like; vinyl alcohols; vinyl pyrrolidones; natural gums such as karaya gum, locust bean gum, guar gum, gelan gum, xanthan gum, gum arabic, tragacanth gum, carrageenan, pectin, agar, alginic acid, sodium alginate and the like, and methacrylates such as those available under the tradename Eudragit® from Rohm Pharma. Other gelling agents include polyoxyethylene-polyoxypropylene copolymers (poloxamers) such as those available under the tradename "Lutrol®", and the like. Preferred gelling agents are those absent free carboxyl groups such as, for instance, hydroxypropylcellulose, hydroxypropylmethylcellulose, hydroxyethylcellulose, methylcellulose, organo/cold water soluble cellulose, hydroxyethylmethylcellulose, ethylcellulose, ethyl(hydroxyethyl)cellulose. For substituted celluloses, a moderate to high degree of substitution is preferred in order to limit the impact of hydroxyl groups on the stability of the tetracycline drug and/or in order to increase the solubility of the gelling agent in a selected solvent system. The preferred degree of substitution is at least 1.0, or preferably in the range of 1.2 to 6.0, or more preferably in the range of 2.5 to 4.5.

The composition may also contain an antioxidant. The amount of antioxidant, if present, will typically range from about 0.005% to about 3.0% by weight of the composition. Illustrative ranges include from about 0.01% to about 2.5% by weight antioxidant, from about 0.05% to about 2% by weight antioxidant, and from about 0.1% to about 1.5% by weight antioxidant. Illustrative amounts of antioxidant include 0.01%, 0.025%, 0.05%, 0.075%, 0.1%, 0.2%, 0.3%, 0.4%, 0.5%, 0.6%, 0.7%, 0.8%, 0.9% and 1% by weight. In one embodiment, the amount of antioxidant comprised within the composition is 0.01% by weight. In another embodiment, the amount of antioxidant comprised within the formulation is 0.2% by weight. Suitable antioxidants include, for example, butylated hydroxyanisole (BHA), butylated hydroxytoluene (BHT), tertiary butyl hydroquinone, propyl gallate, α-tocopherol, sodium metabisulfite, and the like. One preferred class of antioxidants are sulfur-containing antioxidants such as sodium metabisulfite, glutathione, N-acetylcysteine, thioproline, and taurine. Additional preferred compositions comprise an antioxidant selected from the list consisting of a sulfite compound, BHT, sodium selenite, DL-alpha tocopherol, a combination of dithioerythreitol and DL-alpha tocopherol, and sodium erythorbate. Sulfurous acid salts and organic esters (referred to collectively as "sulfites") are also preferred, such as bisulfites, pyrosulfites, metabisulfites, and sulfites.

In one or more embodiments, the topical composition comprises a suitable amount (e.g., about 0.005% to about 3.0% by weight) of a sulfite compound, e.g., a sulfite, metabisulfite or bisulfite salt, where the sulfite is accompanied by a suitable counterion. As described in Example 19, sulfite antioxidants are particularly advantageous for use in the present topical formulations. As shown in Table 24, the sulfite-based antioxidants appear to be particularly beneficial in inhibiting 4-epi-minocycline formation in topical minocycline compositions. See, for example, the data in columns 5 and 6. Exemplary sulfite, bisulfite and metabisulfite salts, e.g., having a suitable counter-ion such as an inorganic or other cation (e.g., sodium, potassium, magnesium, calcium, and the like) are particularly effective in inhibiting formation of 4-epi-minocycline, as well as preventing significant color change (i.e., darkening) of the formulation upon storage. Organic sulfite compounds may also be employed, such as organic esters of sulfurous acid, acyclic sulfites, and cyclic sulfites. Exemplary organic sulfites include ethyl, p-tolyl and isopropyl sulfites, although any suitable organic sulfite may be employed.

As described in Example 19, preferred compositions comprising a sulfite-antioxidant show a low baseline 4-epi-minocycline concentration (relative to minocycline) and a small or no increase in 4-epi-minocycline formation over time, e.g., per week. For example, in some preferred compositions, the relative concentration of 4-epi-minocycline is less than 5.0% at baseline and increases less than 1.00% per week when measured over a 4-week period at 40° C. in closed glass vials, where the 4-week period starts immediately after the baseline measurement. In some preferred compositions, the relative concentration of 4-epi-minocycline is less than 1.0% at a baseline measurement and increases less than 1.00% per week when measured over a 4-week period at 40° C. in closed glass vials, wherein the 4-week period starts immediately after the baseline measurement. More preferably, the relative concentration of 4-epi-minocycline is less than 1.0% at a baseline measurement and increases less than 0.70% per week when measured over a 4-week period at 40° C. in closed glass vials, wherein the 4-week period starts immediately after the baseline measurement. Preferably, the relative concentration of 4-epi-minocycline is in the range of about 0.50% to about 1.00% at a baseline measurement and increases at a rate in the range of about 0.20% to about 0.40% per week when measured over a 4-week period at 40° C. in closed glass vials.

Preferred compositions additionally exhibit a high active minocycline relative concentration and a small or no decrease in active minocycline relative concentration over time. For example, in some preferred compositions, the relative concentration of active minocycline is at least 95.0% at a baseline measurement and decreases less than 1.50% per week when measured over a 4-week period at 40° C. in closed glass vials, wherein the 4-week period starts immediately after the baseline measurement. In some preferred compositions, the relative concentration of active minocycline is at least 98.0% at a baseline measurement and decreases less than 1.00% per week when measured over a 4-week period at 40° C. in closed glass vials, wherein the 4-week period starts immediately after the baseline measurement. More preferably, the relative concentration of 4-epi-minocycline is at least 98.50% at a baseline measurement and decreases less than 0.70% per week when measured over a 4-week period at 40° C. in closed glass vials, wherein the 4-week period starts immediately after the baseline measurement. Preferably, the relative concentration of 4-epi-minocycline is in the range of about 97.0% to about 99.0% at a baseline measurement and decreases at a rate in the range of about 0.30% to about 1.00% per week when measured over a 4-week period at 40° C. in closed glass vials, wherein the 4-week period starts immediately after the baseline measurement.

As shown in Table 24, the sulfite-based antioxidants also appear to be particularly advantageous in preventing a color change (i.e., darkening) of minocycline-containing formulations, as indicated in column 6. This study evaluated the difference in color between the compositions at baseline and after aging for 4 weeks at 40° C. in closed glass vials. The four compositions that included a sulfite salt antioxidant, i.e., compositions 2-ss, 3-sb, 17-ps, and 1-sbs, showed no significant difference in color between the aged and baseline compositions when observed visually. Compositions with non-sulfite-based antioxidants showed significant color change (darkening) over time under the storage conditions employed. Preferred compositions show no significant color change after aging for 4 weeks at 40° C. in closed glass vials. A suitable method for assessing color change is described in Example 19.

The composition may further contain one or more preservatives in an amount typically ranging from about 0.01% to about 2.0% by weight of the composition. Illustrative preservatives include, for example, phenoxyethanol, methyl paraben, propyl paraben, butyl paraben, benzyl alcohol, and the like.

The topical composition may also comprise a small amount, such as 0.1% to 10% by weight, of one or more compounds effective to introduce a favorable scent or aroma, such as a natural oil or other suitable agent. Suitable essential oils include, for example, plant essential oils from eucalyptus, frankincense, patchouli, peppermint, lemon, lavender, orange, rosehip, rosemary, tea tree, jasmine, and the like. For example, in one or more embodiments, the composition comprises a small amount, such as 0.1% to 5% by weight, of 1,8-cineole, or some other essential oil.

The combination of polyol and 1,8-cineole can be particularly effective in preventing the skin from scaling and extreme dryness, especially when administration is for an extended period of time, e.g., for 2 weeks or more. Signs of dry skin which can be prevented include both scaling and itching.

The topical composition may be in a number of different forms, including, for example, a solution, liquid, spray, foam, lotion, gel and the like. Preferably, the composition is a liquid, has good stability, adheres to the skin, and has a smooth feel. Preferably, the composition is not an emulsion. Generally, preferred compositions are absent nanoparticles and/or microparticles, although in some instances, the composition may comprises nanoparticles and/or microparticles. For additional information regarding suitable formulations, see, for example, "Remington: The Science and Practice of Pharmacology," 22nd edition, (Pharmaceutical Press, 2013).

In reference to the stabilities of the compositions provided herein, stability experiments were carried out on exemplary compositions to assess the extent of degradation of the tetracycline class drug in the composition over time as described in Example 3. The tetracycline compound, minocycline, undergoes C4 epimerization, e.g., in the presence of water or a polar protic solvent. The degradation product(s) possess negligible antibiotic activity, such that significant degradation of minocycline in a formulation over its shelf-life will result in reduced activity of the formulation. As can be seen by the results in Tables 3 and 4, the magnesium-containing compositions exhibited a significant improvement over the non-magnesium compositions with respect to the amount of epimer formed (and conversely, the amount of intact minocycline retained in the composition), based upon 18-month extrapolation data. Compositions designated as 90-Mg, 80-Mg and 75-Mg, containing from about 75-90% (w/w) ethanol (i.e., a monohydric aliphatic alcohol) and 10-25% (w/w) propylene glycol (i.e., a polyol) formed only from 3% (w/w) to about 7% (w/w) epimer under the test conditions, while for the magnesium-free compositions, 99-100% conversion to epimer was observed. This example demonstrates the significant stabilizing effect of magnesium on the instant compositions, e.g., in preventing/minimizing degradation/epimerization of the minocycline, and maintaining the activity of the formulation over time. When comparing further amongst the magnesium-containing compositions, the compositions containing from about 25-50% (w/w) ethanol (i.e., monohydric aliphatic alcohol) and from about 50-75% (w/w) polyol (propylene glycol) contained about twice the extrapolated amount of epimer in comparison to the Mg-containing compositions having higher weight percentages of the monohydric aliphatic alcohol and lower weight percentages of the polyol. Thus, in one or more embodiments, it appears that the ethanol component (e.g., monohydric alcohol) has a stabilizing effect on the topical compositions, especially in the presence of magnesium and when in combination with a polyol.

A wide variety of methods may be used for preparing the compositions described herein. Broadly speaking, the compositions may be prepared by combining together the components of the compositions, as described herein, at a temperature and for a time sufficient to provide a pharmaceutically effective and desirable composition. The term "combining together", as used herein, means that all of the components of the compositions are combined and mixed together at about the same time, or that various components are combined in one or more sequences or orders of addition to provide the desired product. The composition can be prepared on a weight/weight (w/w) or a weight/volume (w/v) basis. The composition will generally be readily spreadable, e.g., on a surface of the skin, and preferably will not be runny.

The composition may be prepared by, e.g., admixture of the ingredients typically through the use of vigorous agitation such as high shear mixing. Mixing can also be accomplished by any suitable method using any suitable manual or automated means. Optional additional steps include those which result in the addition of one or more of the optional auxiliary ingredients as set forth above. Methods for preparing a pharmaceutical formulation are well known in the art and are described, for example, in Handbook of Pharmaceutical Formulations: Liquid Products, Vol 3, S. Niazi., CRC Press, 2004.

The composition may be topically applied directly to the affected areas of the skin, for example, using the fingertips, a sponge applicator, a cotton applicator, by spraying, aerosolization, or any other suitable method. The compositions provided herein are useful for treating any condition that is susceptible to treatment with a tetracycline class drug such as minocycline. The compositions provided herein may be used, for example, for treating conditions such as acne, impetigo, cellulitis, erysipelas, folliculitis, furuncles, carbuncles, Lyme disease and other skin infections, rosacea, seborrheic dermatitis, bullous dermatoses, cutaneous sarcoidosis, Kaposi's sarcoma, and neutrophilic dermatoses, and inflammation associated therewith. Types of acne include, for example, acne vulgaris, acne rosacea, acne conglobata, acne fulminans, gram-negative folliculitis, and pyoderma faciale, among others. For example, the composition may be used for treating moderate to severe acne, and the acne may be nodular or cystic.

In one or more embodiments, the method comprises the step of administering a topical composition as provided herein to an accessible body surface of a human or an animal in need of such treatment. Generally, the composition is applied in a conventional amount from once to several times weekly or daily on the affected areas of the skin, until the acne or condition being treated has visibly diminished or disappeared. For example, the topical composition may be applied topically at least once daily for a period of at least 1 month, or may be applied to the skin once or twice daily for a period of from 6 to 52 weeks or even longer. The number of applications and course of treatment will vary with the severity of the condition being treated, patient considerations, and the like. Thus, the composition may, in certain instances by applied one daily, twice daily, once every other day, from one to three times weekly, from 1 to 4 times weekly, every 3 days, etc.

A conventional amount is an amount that is sufficient to spread, e.g., thinly spread, over the affected area. If desired, the efficacy of treatment may be quantified by using a grading system such as the Leeds system (O'Brien, S C., et al., J. Dermatol Treat 1998; 9:215-220), the Comprehensive Acne Severity Scale (Tan, J K, et al., J. Cutan Med Surg 2007 November; 11(6):211-6), or the Global Acne Grading System (Doshi, A., et al., Int. J. Dermatol 1997 June 36(6); 416-8). In one or more embodiments, the efficacy of treatment is assessed by a visual examination of the affected area. In some cases, prophylactic treatment may be continued even if the condition has visibly diminished or disappeared, as a preventative measure. In some embodiments, the efficacy of treatment is assessed by an evaluation of a reduction in total lesion count, where application of a topical composition as described herein is effective to result in a reduction in total lesion count as measured from the commencement of treatment.

Features of Solvent Systems and Topical Compositions

Turning now to consideration of the Examples, Example 1 demonstrates the solubility of magnesium-complexed minocycline in comparison to minocycline alone (i.e., non-complexed minocycline) in the same solvent system as a function of the concentration of ethanol and propylene glycol in the composition at room temperature and under atmospheric conditions. As can be seen, magnesium-complexed minocycline is considerably more soluble in a mixture comprising ethanol and propylene glycol than it is in either ethanol or propylene glycol independently. Additionally, magnesium-complexed minocycline is notably more soluble than minocycline in a mixture comprising ethanol and propylene glycol.

As demonstrated in Example 1, minocycline hydrochloride has a solubility exceeding 100 mg/ml (e.g., 100 mg/ml to about 165 mg/ml) at room temperature in select compositions comprising ethanol, propylene glycol, and magnesium chloride. Thus, in certain preferred embodiments, the topical composition comprises the foregoing components in addition to the tetracycline class drug, i.e., ethanol, propylene glycol, and magnesium chloride.

Moreover, as demonstrated in Example 1, the Applicants have discovered that adding a source of magnesium, such as magnesium chloride, to a topical composition as described herein increases the solubility of a tetracycline class drug, such as minocycline, in mixtures of a monohydric aliphatic alcohol, such as ethanol, and a polyol, such as propylene glycol, particularly for compositions in which the amount by weight of the alcohol exceeds the amount of the polyol. Thus in one or more preferred embodiments, the amount by weight of alcohol in the composition exceeds the amount by weight of the polyol component.

Figure 1B:
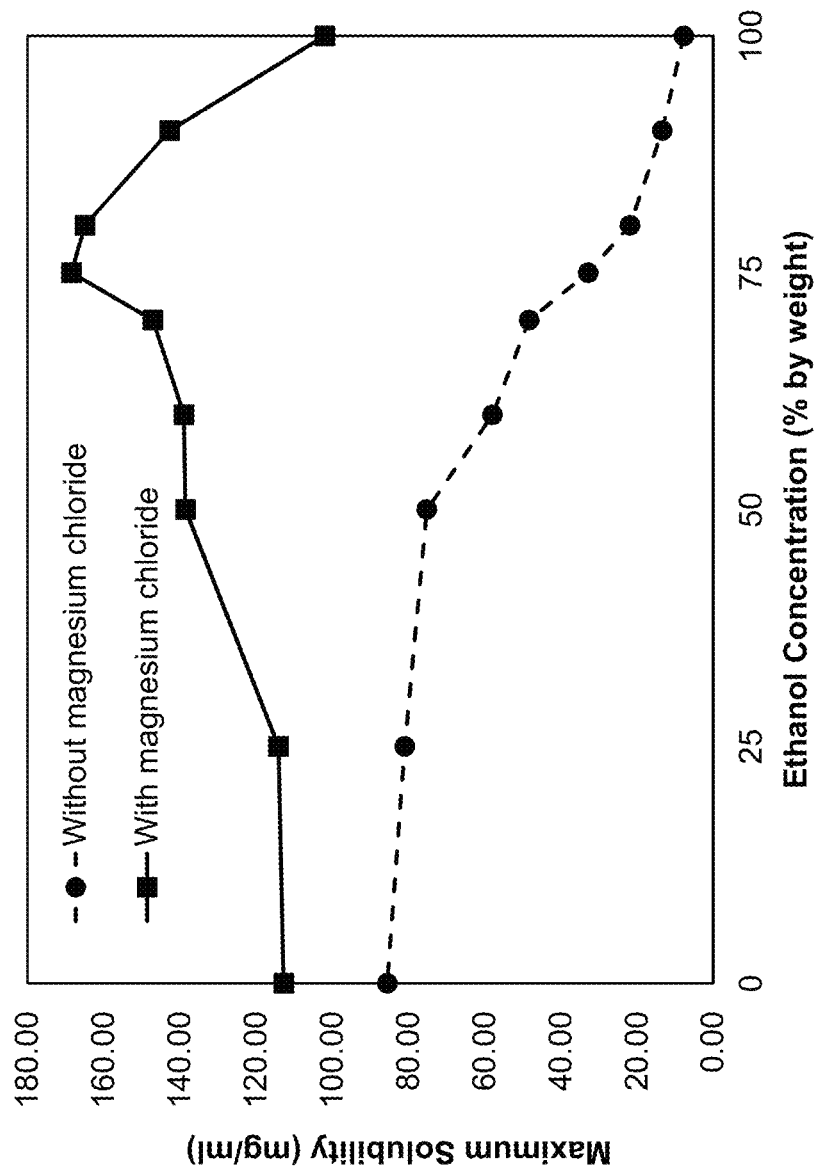

In the graphs presented as FIGS. 1a and 1b, the concentrations of minocycline hydrochloride are plotted as a function of ethanol concentration in the solvent system. Both FIGS. 1a and 1b illustrate that the incorporation of magnesium chloride into the instant compositions significantly increases the solubility of minocycline hydrochloride, particularly for ethanol alone (100% ethanol) and for compositions with high ethanol concentrations in mixtures of ethanol and propylene glycol. Moreover, the relative amounts of each of the composition components, e.g., monohydric aliphatic alcohol and polyol, required to achieve maximal drug solubility changes upon the addition of the magnesium salt. Notably, in Example 1, the peak (i.e., maximum) concentration of dissolved drug for mixtures of ethanol and propylene glycol shifts from approximately 25% ethanol to approximately 75% ethanol upon incorporation of a magnesium salt, and the maximum amount of drug that dissolves increases by approximately 2-fold upon incorporation of the magnesium salt.

In exemplary topical compositions, the ratio of the monohydric aliphatic alcohol to the polyol exceeds 1:1 (w/w), i.e., is between 1:1 and 99:1 (w/w), or is between 3:2 and 9:1 (w/w), or is between 2:1 and 4:1 (w/w), and the combined amount of the polyol and the monohydric aliphatic alcohol in the composition exceeds 50% (w/w), or preferably exceeds 75% (w/w) of the composition, or more preferably exceeds 90% (w/w), of the composition. In some compositions, the ratio of the ethanol to the propylene glycol exceeds 1:1 (w/w), such as between 1:1 and 99:1 (w/w), between 3:2 and 9:1 (w/w), or between 2:1 and 4:1 (w/w), and the combined amount of propylene glycol and ethanol in the composition exceeds 50% (w/w), or preferably exceeds 75% (w/w) of the composition, or more preferably exceeds 90% (w/w), of the composition. In such compositions, the tetracycline class drug is, in one or more embodiments, minocycline.

When a composition comprising a volatile monohydric aliphatic alcohol, such as ethanol or isopropanol, is applied to the skin, the volatile alcohol leaves the surface of the skin rapidly, through evaporation, penetration, or a combination of both. This rapid reduction in solvent content can significantly increase the concentration of the active tetracycline class drug on the skin surface or within the upper layers of the skin tissue. If the solubility of the material in the remaining solvent is insufficient to maintain the drug in solution, the drug may form a solid phase, which will reduce the subsequent penetration rate of the drug into the skin because the drug must first overcome the dissolution energy barrier before penetrating into the skin. For this reason, if a volatile monohydric aliphatic alcohol is used, it may be preferable to have the concentration of the volatile alcohol be higher than the point of maximum solubility.

In some compositions, the ratio of the monohydric aliphatic alcohol to the polyol exceeds 3:1 (w/w), such as between 3:1 and 99:1 (w/w), between 3:1 and 9:1 (w/w), or between 4:1 and 8:1 (w/w), and the combined amount of the polyol and the monohydric aliphatic alcohol in the composition exceeds 50% (w/w), or preferably exceeds 75% (w/w) of the composition, or more preferably exceeds 90% (w/w), of the composition. In some compositions, the ratio between ethanol and propylene glycol exceeds 3:1 (w/w), such as between 3:1 and 99:1 (w/w), between 3:1 and 9:1 (w/w), or between 4:1 and 8:1 (w/w), and the combined amount of propylene glycol and ethanol in the composition exceeds 50% (w/w), or preferably exceeds 75% (w/w) of the composition, or more preferably exceeds 90% (w/w), of the composition. In such compositions, the tetracycline class drug is preferably minocycline.

Additionally, for compositions in which the polyol is less volatile than the alcohol, the concentration of the drug in the composition at the skin surface will typically precipitate less quickly than if the polyol is not used. This slower rate of precipitation will allow the drug to have more time to penetrate into the skin, which can be beneficial for improving the efficiency of delivery of the drug to the target tissue (e.g. epidermis, dermis, or sebaceous gland) or target body fluid (e.g. sebum).

Turning now to Example 2, this example provides differential scanning calorimetry data demonstrating that the difference in solubility described in Example 1 appears to result from a eutectic that is formed by the interaction of the representative class components, minocycline, magnesium, ethanol, and propylene glycol.

Example 3 provides short-term stability data that indicates that minocycline is not sufficiently stable in propylene glycol alone, even when stabilized by the presence of magnesium. In contrast, a stable composition is produced by combining ethanol and propylene glycol. Magnesium stabilization notably improves the stability of the combination composition as can be seen by the results in Table 2. Preferred compositions are those having low amounts of epimer formation, when extrapolated to 18 months stability. Compositions in which the epimer formation is less than about 15% under the accelerated stability conditions employed are preferred.

Turning to Example 4, Example 4 presents data from ex vivo drug penetration studies on human tissue samples. These experiments quantify the amount of minocycline that penetrates beyond the first couple layers of the skin following topical application of the composition, and demonstrate (i) that the efficiency of penetration increases as propylene glycol is replaced with ethanol, and (ii) good efficiency of penetration into the skin.

In some embodiments, the efficiency of penetration multiplied by the concentration of the tetracycline class drug in the composition will desirably exceed the minimum inhibitory concentration of *P. acnes* ATCC 6919 bacteria for the tetracycline class drug. In some embodiments, the efficiency of penetration of the tetracycline class drug (in ex vivo human skin samples as described in Example 4) exceeds 5%, more preferably exceeds 8%, or even more preferably exceeds 10%. In some embodiments, the efficiency of penetration of the tetracycline class drug is in a range of from about 5% to 30%, or is in a range of about 5% to 10%, or more preferably, is in a range of 10% to 30%.

In considering the results provided in Example 5, this example illustrates that the MIC value for minocycline is altered by the presence of magnesium, suggesting that minocycline forms a complex with magnesium that is not formed with calcium. The MIC value (or, alternatively, a designated multiple thereof) can be used as a threshold for determining whether adequate delivery into a target tissue has been achieved. The data from Example 4 indicates that the efficiency of penetration is sufficient to exceed the MIC for minocycline for minocycline concentrations that are well below the solubility limits measured in Example 1.

Examples 6 and 7 show that not only does topically applied minocycline comprised within the formulations provided herein penetrate into the skin, but that it preferentially and advantageously partitions into sebaceous glands and oily reservoirs of the skin. Data is presented from experiments using Matrix-Assisted Laser Desorption/Ionization Time-of-Flight mass spectrometry (MALDI-TOF mass spectrometry) (Example 6) and fluorescent microscopy (Example 7) techniques. See, e.g., FIGS. 4a-c and FIGS. 5a-c, and FIG. 6. Based upon this data, it appears that the tetracycline is preferentially delivered to lipid-rich tissues, both on and within the skin.

Example 8 provides data from an in vivo study in Sprague-Dawley rats that indicates that repeated daily topical application of compositions according to the invention are non-irritating and non-staining to the skin. Thus, in one or more embodiments, the topical composition is non-irritating when applied to the skin. In yet another embodiment, the topical composition is non-staining when applied to the skin of a subject.

Example 9 describes a method for preliminary optimization of the molar ratio of magnesium to a tetracycline-class drug for a particular solvent system. The method demonstrates a rough correlation between stability of the drug within the formulation and its fluorescence emission. Using this method, an optimal ratio of magnesium to minocycline may be determined.

Various exemplary embodiments of the topical composition are described in Example 10 in accordance with the disclosure.

Providing additional support for the stability of the instant formulations, Example 11 provides 6-month room-temperature stability data that indicates that minocycline is stable in a solution comprising propylene glycol, ethanol, and magnesium chloride.

Further to the data described above in relation to Example 6 and 7, Example 12 provides further support for the excellent skin uptake of liquid formulations in accordance with the invention, and additionally demonstrates the superior nature of the present formulations in comparison to an illustrative lipophilic formulation. In both illustrative 1% and 4% minocycline formulations, uptake efficiency was 2-3 fold greater for hydrophilic formulations as provided herein (comprising minocycline, magnesium chloride, ethanol, propylene glycol and sodium metabisulfite) in comparison to a lipophilic formulation as described in Table 9. Additionally, formulations in accordance with the invention resulted in lower amounts of minocycline epimer detected in treated skin when compared to the lipophilic formulation, indicating the enhanced stability of the instant formulations in comparison to the lipophilic formulation. Fluorescent imaging results illustrated that the 4% minocycline formulation, BPX-4M, delivered increased quantities of minocycline to the layers of the stratum corneum, epidermis and pilosebaceous glands when compared to an illustrative 4% lipophilic formulation.

The instant formulations are effective to provide a therapeutically effective dose of tetracycline class drug when applied topically to the skin; see, e.g., Example 13. The supporting examples also illustrate the non-irritating nature of the instant compositions. See, e.g., Examples 14, 15, and 18. Additionally, results such as those described in Example 16 demonstrate that repeat dosing of a mammal can be performed safely for compositions as provided herein at dosage levels of minocycline in the range of 0.0 mg/cm$^2$/day to 0.5 mg/cm$^2$/day, or preferably in the range of about 0.025 mg/cm$^2$/day to about 0.5 mg/cm$^2$/day, or more preferably in the range of about 0.025 mg/cm$^2$/day to about 0.25 mg/cm$^2$/day. Higher doses of minocycline allow more aggressive treatments. Dosages of at least 0.01 mg/cm$^2$/day or dosages of at least 0.025 mg/cm$^2$/day are preferred.

Example 19 illustrates some of the advantages associated with use of a sulfite-based antioxidant in liquid topical compositions of the type describe herein when placed under storage conditions for a prolonged period of time. This example highlights the recognition that compositions as provided herein and comprising a sulfite compound (as an antioxidant) are significant more stable than compositions comprising non-sulfite anti-oxidants. Preferred compositions show a low baseline 4-epi-minocycline relative concentration and a small or no increase in 4-epi-minocycline relative concentration per week when stored under representative storage conditions. For example, in some preferred compositions, the relative concentration of 4-epi-minocycline is less than 5.0% at a baseline measurement and increases less than 1.00% per week when the liquid composition is measured (evaluated) over a 4-week period at 40° C. in closed glass vials, wherein the 4-week period starts immediately after the baseline measurement. In some preferred compositions, the relative concentration of 4-epi-minocycline is less than 1.0% at a baseline measurement and increases less than 1.00% per week when measured over a 4-week period at 40° C. in closed glass vials, wherein the 4-week period starts immediately after the baseline measurement. More preferably, the relative concentration of 4-epi-minocycline is less than 1.0% at a baseline measurement and increases less than 0.70% per week when measured over a 4-week period at 40° C. in closed glass vials, wherein the 4-week period starts immediately after the baseline measurement. Preferably, the relative concentration of 4-epi-minocycline is in the range of about 0.50% to about 1.00% at a baseline measurement and increases at a rate in the range of about 0.20% to about 0.40% per week when measured over a 4-week period at 40° C. in closed glass vials, wherein the 4-week period starts immediately after the baseline measurement.

Additionally, preferred compositions show a high active minocycline relative concentration and a small or no decrease in active minocycline relative concentration per week. For example, in some preferred compositions, the relative concentration of active minocycline is at least 95.0% at a baseline measurement and decreases less than 1.50% per week when measured over a 4-week period at 40° C. in closed glass vials, wherein the 4-week period starts immediately after the baseline measurement. In some preferred compositions, the relative concentration of active minocycline is at least 98.0% at a baseline measurement and decreases less than 1.00% per week when measured over a 4-week period at 40° C. in closed glass vials, wherein the 4-week period starts immediately after the baseline measurement. More preferably, the relative concentration of 4-epi-minocycline is at least 98.50% at a baseline measurement and decreases less than 0.70% per week when measured over a 4-week period at 40° C. in closed glass vials, wherein the 4-week period starts immediately after the baseline measurement. Preferably, the relative concentration of 4-epi-minocycline is in the range of about 97.0% to about 99.0% at a baseline measurement and decreases at a rate in the range of about 0.30% to about 1.00% per week when measured over a 4-week period at 40° C. in closed glass vials, wherein the 4-week period starts immediately after the baseline measurement. Calculations for determine relative concentrations of 4-epi-minocycline and active minocycline are described in Example 19.

As shown in Example 19, representative compositions that included a sulfite compound as an antioxidant, i.e., compositions 2-ss, 3-sb, 17-ps, and 1-sbs, did not have a significant difference in color between the aged and baseline compositions when examined under the storage conditions described above. Each of the other non-sulfite containing compositions showed a significant color difference. The strength of these color differences did not correlate with the amount of degradation of the relative concentration of the active minocycline. Preferred compositions show no significant color changes after aging for 4 weeks at 40° C. in closed glass vials. In a preferred composition, the color change after aging for 4 weeks at 40° C. in a closed glass vial is less than 50, or more preferably less than 20, in distance in 3-dimensional RGB space where each value is measured on a 0-255 range. Distance is calculated in 3-dimensional RGB space according to the following formula: distance$_{RGB}$= $((\Delta R)^2+(\Delta G)^2+(\Delta B)^2)^{0.5}$.

Additional advantages and features of the instant formulations are described throughout the instant document.

Thus, several advantageous properties are associated with the formulations and topical treatment methods described herein. The topical formulations are effective to deliver the tetracycline drug directly to the epidermis and sebaceous glands. Moreover, the formulations described herein are easy to apply, not sticky, and do not occlude the skin. The formulations provide effective delivery of tetracycline drug, e.g., minocycline, to sebaceous glands where P. acne resides, in therapeutically effective amounts, and demonstrate no or minimal irritation potential. Moreover, the formulations are stable over an extended period of time and upon application, e.g., as demonstrated by formation of minimal quantities of epimerization product.

EXAMPLES

The following examples are put forth to provide those of ordinary skill in the art with a complete disclosure and description of how the composition, its components, active ingredients, solvents, and the like, are prepared and evaluated, along with related methods, and are intended to be purely exemplary. Thus, the examples are in no way intended to limit the scope of what the inventors regard as their invention. There are numerous variations and combinations, e. g., component concentrations, desired solvents, solvent mixtures, antioxidants, and other mixture parameters and conditions that may be employed to optimize composition characteristics such as purity, yield, stability, odor, color, viscosity, penetration, and the like. Such are considered as well within the scope of the present disclosure.

Unless otherwise indicated, in each of the following examples, the form of minocycline hydrochloride that was used was minocycline hydrochloride dihydrate, which is referred to in the examples which follow as simply "minocycline hydrochloride". It will be evident to those skilled in the art how compositions can be made using other salts and hydrates of minocycline.

Example 1

Solubility of Minocycline and Magnesium-Stabilized Minocycline

A study was performed to assess the effect of magnesium chloride ($MgCl_2$) on the solubility of minocycline in mixtures of ethanol and propylene glycol. Mixtures of ethanol (Spectrum Chemicals, Gardena, Calif.), propylene glycol (Spectrum Chemicals, Gardena, Calif.), and 1,8-cineole (Penta International Company, Livingston, N.J.) were prepared as described in Table 1. The compositions correspond to the following approximate ratios by weight of ethanol and propylene glycol: 0:1, 1:3, 1:1, 3:1, 4:1, 9:1, and 1:0.

TABLE 1

MIXTURES FOR SOLUBILITY EXPERIMENTS WITH VARYING AMOUNTS OF MAGNESIUM CHLORIDE

| SAMPLE DESIGNATION | ETHANOL (% W/W) | PROPYLENE GLYCOL (% W/W) | 1,8-CINEOLE (% W/W) | TEST MATERIAL |
|---|---|---|---|---|
| 100-MNC | 99 | 0 | 1 | Minocycline*HCl |
| 90-MNC | 89.5 | 9.5 | 1 | Minocycline*HCl |
| 80-MNC | 79.5 | 19.5 | 1 | Minocycline*HCl |
| 75-MNC | 74.5 | 24.5 | 1 | Minocycline*HCl |
| 50-MNC | 49.5 | 49.5 | 1 | Minocycline*HCl |
| 25-MNC | 24.5 | 74.5 | 1 | Minocycline*HCl |
| 0-MNC | 0 | 99 | 1 | Minocycline*HCl |
| 100-Mg | 99 | 0 | 1 | Minocycline*HCl—$MgCl_2$ |
| 90-Mg | 89.5 | 9.5 | 1 | Minocycline*HCl—$MgCl_2$ |
| 80-Mg | 79.5 | 19.5 | 1 | Minocycline*HCl—$MgCl_2$ |
| 75-Mg | 74.5 | 24.5 | 1 | Minocycline*HCl—$MgCl_2$ |
| 50-Mg | 49.5 | 49.5 | 1 | Minocycline*HCl—$MgCl_2$ |
| 25-Mg | 24.5 | 74.5 | 1 | Minocycline*HCl—$MgCl_2$ |
| 0-Mg | 0 | 99 | 1 | Minocycline*HCl—$MgCl_2$ |
| 100-MNC-0C | 100 | 0 | 0 | Minocycline*HCl |
| 90-MNC-0C | 90 | 10 | 0 | Minocycline*HCl |
| 80-MNC-0C | 80 | 20 | 0 | Minocycline*HCl |
| 75-MNC-0C | 75 | 25 | 0 | Minocycline*HCl |
| 70-MNC-0C | 70 | 30 | 0 | Minocycline*HCl |
| 60-MNC-0C | 60 | 40 | 0 | Minociine*HCl |
| 50-MNC-0C | 50 | 50 | 0 | Minocycline*HCl |
| 25-MNC-0C | 25 | 75 | 0 | Minocycline*HCl |
| 0-MNC-0C | 0 | 100 | 0 | Minocycline*HCl |
| 100-Mg-0C | 100 | 0 | 0 | Minocycline*HCl—$MgCl_2$ |
| 90-Mg-0C | 90 | 10 | 0 | Minocycline*HCl—$MgCl_2$ |
| 80-Mg-0C | 80 | 20 | 0 | Minocycline*HCl—$MgCl_2$ |
| 75-Mg-0C | 75 | 25 | 0 | Minocycline*HCl—$MgCl_2$ |
| 70-Mg-0C | 70 | 30 | 0 | Minocycline*HCl—$MgCl_2$ |
| 60-Mg-0C | 60 | 40 | 0 | Minocycline*HCl—$MgCl_2$ |
| 50-Mg-0C | 50 | 50 | 0 | Minocycline*HCl—$MgCl_2$ |
| 25-Mg-0C | 25 | 75 | 0 | Minocycline*HCl—$MgCl_2$ |
| 0-Mg-0C | 0 | 100 | 0 | Minocycline*HCl—$MgCl_2$ |

Two test materials were employed as shown in Table 1. The first test material, "minocycline*HCl with $MgCl_2$," was formed by mixing minocycline hydrochloride (Euticals S.P.A, Origgio, Italy) with magnesium chloride (Sigma-Aldrich Corp., St. Louis, Mo.) in a 1:1 ratio (w/w). (As described supra, "minocycline hydrochloride dihydrate" was used in the Examples where "minocycline hydrochloride" is mentioned.) The mixture was blended in a vortex mixer (VORTEX GENIE, Scientific Industries, Inc. Bohemia, N.Y.) at approximately 3000 rpm until obtaining a uniform mixture or for at least 3 minutes. A ratio of 1:1 (w/w) of the magnesium chloride (anhydrous) and minocycline hydrochloride corresponds to a molar ratio of approximately 5.6:1 magnesium to minocycline. The second test material, "minocycline*HCl," was minocycline hydrochloride alone.

Two grams (2.0 g) of each of the solvents listed in Table 1 were placed in a 4 mL clear glass vial (Phenomenex, Torrance, Calif.). A small amount of the test material was added to each glass vial, the lid was placed on the vial, and the vial was agitated using a vortex mixer (VORTEX GENIE, Scientific Industries, Inc. Bohemia, N.Y.) and sonicated (Branson 3210, Branson Ultrasonics, Danbury, Conn.). These steps were repeated until the added test material would no longer dissolve completely after sonication. Each glass vial was then left overnight at room temperature in dark conditions with the lid sealed tightly. These steps created a saturated solution in each glass vial. A 100 microliter (µL) sample of the liquid portion of the mixture was removed from the top of each vial. During this sampling step, care was taken not to disturb any precipitated solids at the bottom of each vial. These sampled portions were each spun in a micro-centrifuge (SORVALL RMC 14, DuPont Sustainable Solutions, Wilmington, Del.) at 12,000 rpm for 2 minutes. A 20 microliter (µL) portion of the supernatant was mixed with ethanol in a 1:49 ratio. A 5 microliter (µL) portion of the resulting mixture was used in an HPLC method for assessment of minocycline as described in the next paragraph.

The HPLC method described in this paragraph and the calculations described in the next paragraph are used for all Examples described herein that describe measured minocycline concentrations except where a variation or an alternate method is described. A 5 microliter (µL) sample is injected into a high-performance liquid chromatography machine (HPLC) (Agilent, Santa Clara, Calif.). The HPLC column (Phenomenex, Inc. Torrance, Calif.) was a C-18 column 100×4.6 mm with a particle size of 5 micrometers (µm). The HPLC system also used a guard column (Phenomenex, Inc.) and a mobile phase consisting of a base solvent of 12% (v/v) Dimethylformamide (Spectrum Chemicals, Gardena, Calif.), 8% Tetrahydrofuran (Spectrum Chemicals, Gardena, Calif.), 18 mM EDTA (Spectrum Chemicals, Gardena, Calif.), and 0.12 M Ammonium Oxalate (Spectrum Chemicals, Gardena, Calif.). The mobile phase was pH adjusted to 7.1-7.2. The HPLC flow rate was 1 mL per minute with a column temperature of 40° C., a detection wavelength of 280 nm, and a runtime of at least 15 minutes. The amount of minocycline that was in solution was determined based on an external calibration. This allowed calculation of the concentration of the minocycline hydrochloride.

Degradation of minocycline to its epimer was quantified by evaluating the change in the relative concentration of 4-epi-minocycline, which was calculated as the 4-epi-minocycline peak area divided by the sum of the 4-epi-minocycline peak area and the active minocycline peak area. As a separate quantification, stability was quantified by evaluating the change in the relative concentration of active minocycline, which was calculated as the active minocycline peak divided by the sum of the peak areas for all peaks observed in the HPLC chromatograph. The term all peaks in this sense means the peaks occurring after elution of the solvent peaks. The solvent peaks generally eluted within the first 2 minutes and so the measurement of all peaks started at the 2 minute point. As will be apparent to those skilled in the art, the location of the solvent peaks may vary and the initiation point would be adjusted accordingly.

For this Example 1, the resulting concentration describes the concentration that was dissolved in the 2 grams of solvent mixture that was first added to each glass vial.

In FIGS. 1A and 1B, the resulting concentrations of minocycline hydrochloride are plotted as a function of the ethanol concentration in the solvent system. These graphs thus represent the solubility of active minocycline as a function of the ethanol concentration in the composition by weight for compositions with 1% cineole (FIG. 1A) and without cineole (FIG. 1B). The results demonstrate that adding magnesium chloride significantly increases the solubility of minocycline hydrochloride, particularly for ethanol alone (see data points at 100% ethanol concentration) and for compositions with high ethanol concentrations in mixtures of ethanol and propylene glycol. Additionally, the peak concentration for mixtures of ethanol and propylene glycol shifts from approximately 25% ethanol to approximately 75% ethanol in the presence of the magnesium salt.

Example 2

DSC Measurements

This experiment was performed to assess whether there was a difference in the melting point for a mixture of minocycline hydrochloride, magnesium chloride, ethanol, and propylene glycol relative to the individual melting points of minocycline hydrochloride and magnesium chloride.

A test mixture of minocycline hydrochloride (Euticals S.P.A, Origgio, Italy) with magnesium chloride (Sigma-Aldrich Corp., St. Louis, Mo.) in a 1:1 ratio (w/w) was prepared by blending in a vortex mixer (VORTEX GENIE, Scientific Industries, Inc. Bohemia, N.Y.) at approximately 3000 rpm until obtaining a uniform mixture or for at least 3 minutes. The dry mixture was placed into a ceramic mortar and manually agitated with stainless steel spatula while a solution consisting of ethanol (Spectrum Chemicals, Gardena, Calif.), and propylene glycol (Spectrum Chemicals, Gardena, Calif.) in a 3:1 ratio (w/w) was added drop wise to uniformly wet the mixture. The wet sample was then gently mixed to provide consistent drying at ambient conditions.

Thermal analysis was performed by Differential Scanning calorimetry (DSC) using a Q2000 DSC (TA instruments, New Castle, Del.) calibrated with indium. DSC measurements were performed for minocycline hydrochloride, magnesium chloride, and the dried test mixture. Samples of 2-7 mg were weighed and analyzed in sealed aluminum pans in the range of 25° C. to 250° C. at a heating rate of 10° C./min using nitrogen purge gas.

Comparison of the melting points of the dried test mixture to the melting points of the minocycline hydrochloride and magnesium chloride indicated a prominent melting point depression, which is indicative of formation of eutectic mixture.

In summary, it has been discovered by the Applicants that compositions comprising a tetracycline class drug, a source of magnesium, a monohydric aliphatic alcohol, and a polyol form a eutectic. This eutectic was demonstrated by evaporating the solvent from the composition to form a metastable deposit for evaluation with differential scanning calorimetry (DSC) and comparing the results to DSC results for the dry components to determine whether a reduction in melting point was achieved.

Example 3

Stability of Minocycline and Magnesium-Stabilized Minocycline

The effect of component contributions to drug potency stability and epimer formation for illustrative mixtures of minocycline hydrochloride, magnesium chloride, ethanol, and propylene glycol was assessed using the compositions described in Example 1.

The degradation and stability of minocycline in compositions were measured at Day 1 and Day 6 following storage in the dark at room temperature conditions within sealed glass vials.

In Table 2, the formation of 4-epi-minocycline was extrapolated to a period of 18 months. The extrapolation calculation assumed that the degradation mechanisms continue at the same mathematical rate as for days 1-6. This represents a worst case value and does not take into account the fact that 4-epi-minocycline may reach equilibrium with minocycline within the composition, such that the extremely high levels of 4-epi-minocycline, such as 99.76% and 100%, may not represent a physical reality. In such cases, these values simply indicate that the epimerization reaction will proceed until equilibrium is reached.

Figure 2A:
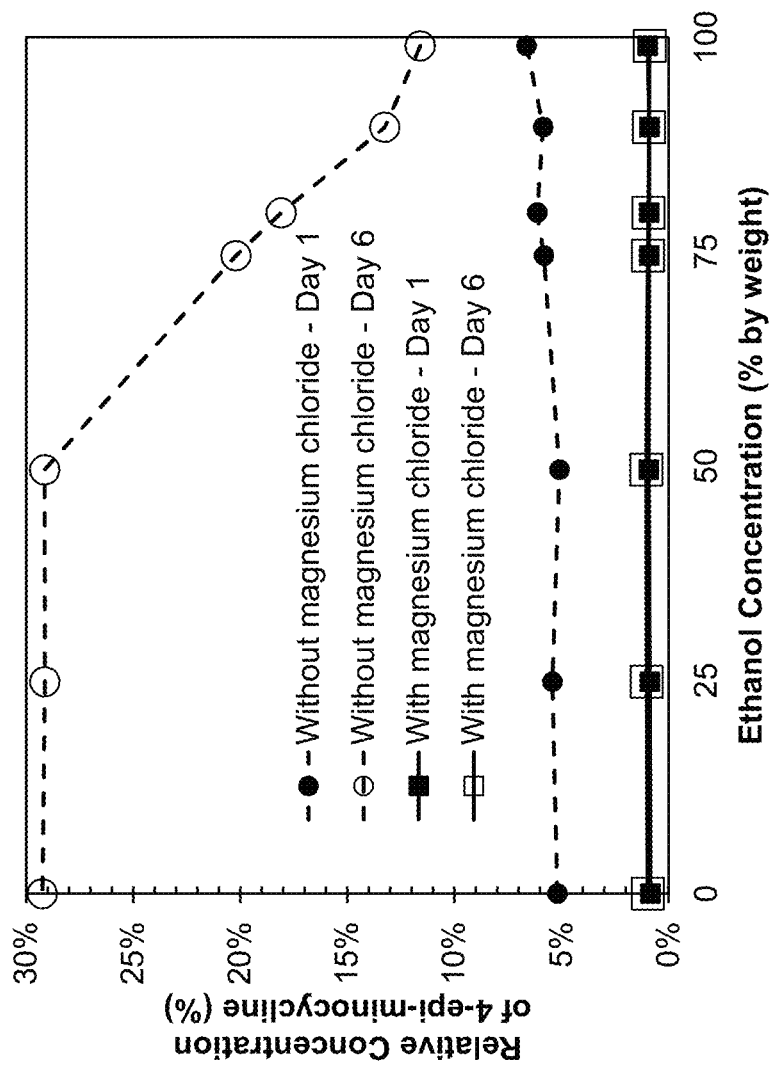
FIGS. 2A-2D are graphs illustrating the relative concentrations of 4-epi-minocycline and minocycline over time in compositions comprising minocycline hydrochloride, ethanol, and propylene glycol as described in Example 3. The dashed lines in the graphs are for compositions without magnesium chloride. The solid lines in the graphs are for similar liquid compositions with magnesium chloride.
Figure 2B:
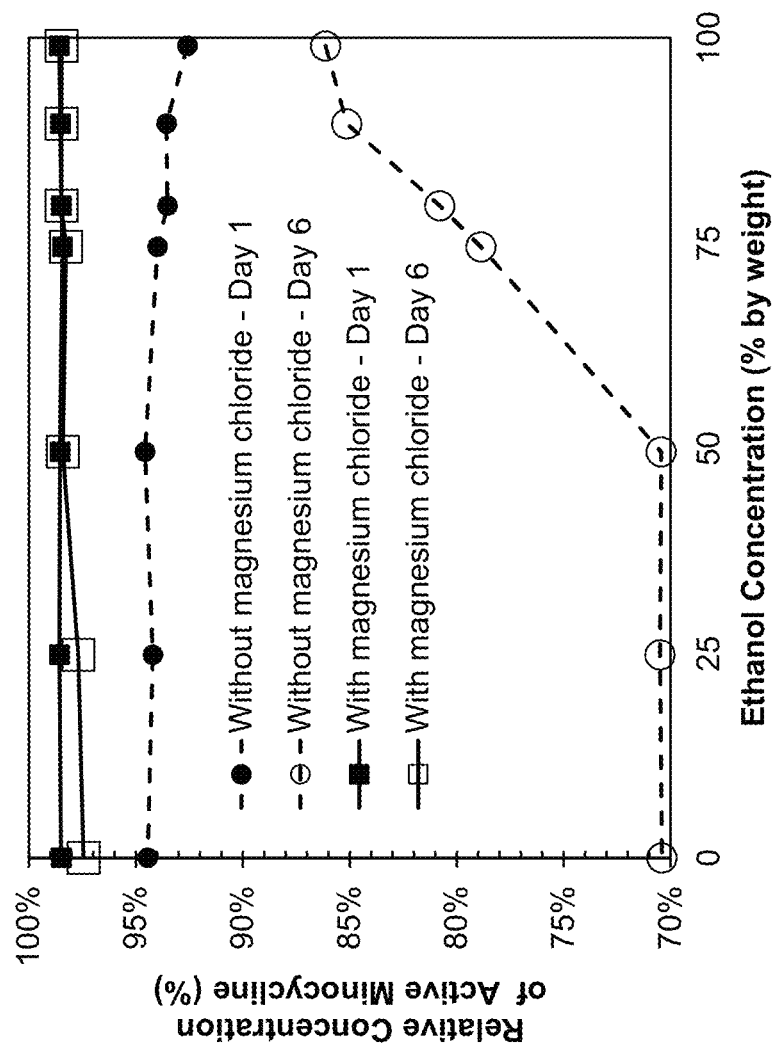
Figure 2C:
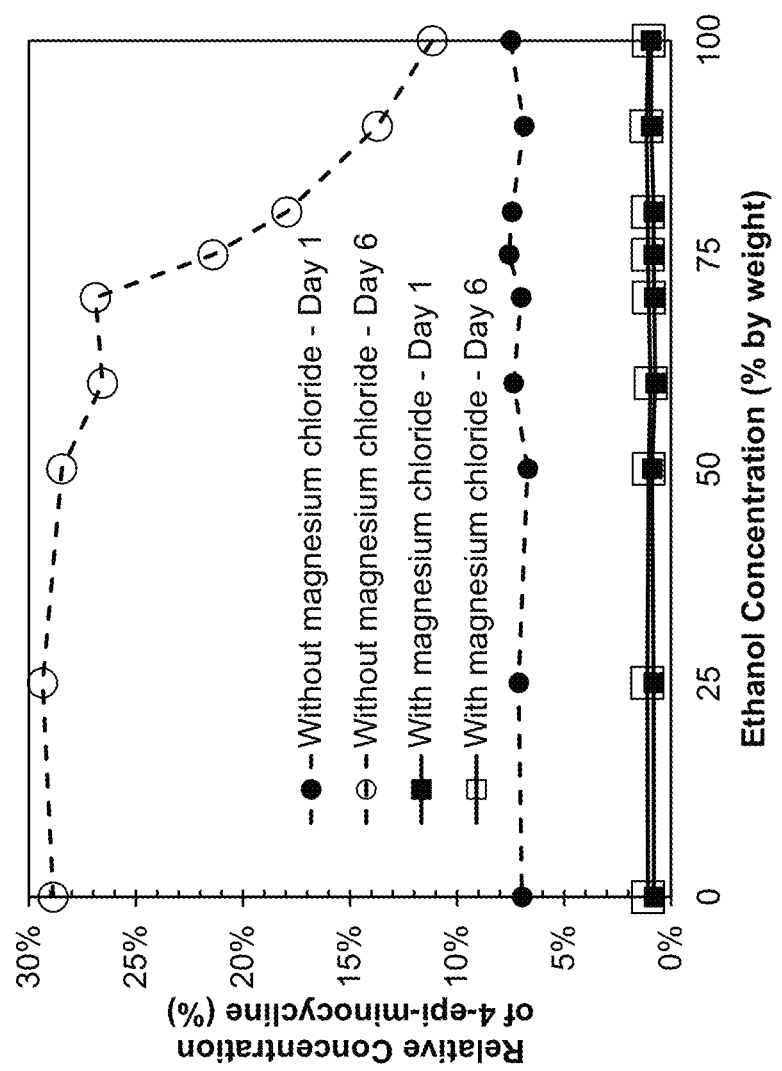
Figure 2D:
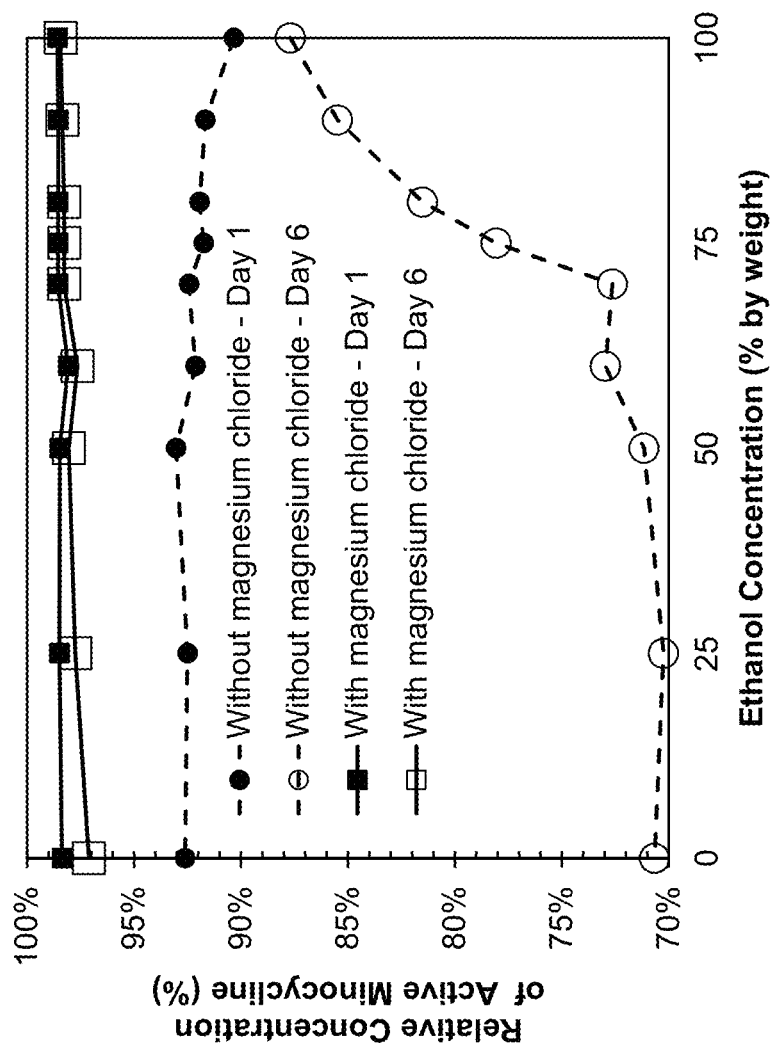

FIGS. 2a and 2b are graphs of the relative concentration of active minocycline as a function of the ethanol concentration by weight for compositions with 1% cineole. FIGS. 2c and 2d are graph of the relative concentration of active minocycline as a function of the ethanol concentration by weight for compositions with no cineole.

TABLE 2

RELATIVE CONCENTRATIONS OF 4-EPI-MINOCYCLINE

| SAMPLE DESIGNATION (SEE EXAMPLE 1) | DAY 1 | DAY 6 | CONCENTRATION CHANGE FROM DAY 1 TO DAY 6 (DIFFERENCE IN CONCENTRATIONS) | EXTRAPOLATED CONCENTRATION AT 18 MONTHS |
|---|---|---|---|---|
| 100-MNC | 6.63% | 11.59% | 4.96% | 99.76% |
| 90-MNC | 5.86% | 13.25% | 7.39% | 99.99% |
| 80-MNC | 6.13% | 18.08% | 11.95% | 100.00% |
| 75-MNC | 5.82% | 20.19% | 14.37% | 100.00% |
| 50-MNC | 5.09% | 29.14% | 24.05% | 100.00% |
| 25-MNC | 5.42% | 29.13% | 23.71% | 100.00% |
| 0-MNC | 5.19% | 29.25% | 24.06% | 100.00% |
| 100-Mg | 0.97% | 0.87% | −0.10% | 0.00% |
| 90-Mg | 0.89% | 0.91% | 0.02% | 3.05% |
| 80-Mg | 0.90% | 0.93% | 0.03% | 4.36% |
| 75-Mg | 0.90% | 0.95% | 0.05% | 6.68% |
| 50-Mg | 0.91% | 1.03% | 0.11% | 12.71% |
| 25-Mg | 0.87% | 1.01% | 0.14% | 15.23% |
| 0-Mg | 0.84% | 0.96% | 0.12% | 13.21% |
| 100-MNC-0C | 7.49% | 11.16% | 3.67% | 98.90% |
| 90-MNC-0C | 6.87% | 13.71% | 6.84% | 99.98% |
| 80-MNC-0C | 7.43% | 17.95% | 10.52% | 100.00% |
| 75-MNC-0C | 7.57% | 21.40% | 13.83% | 100.00% |
| 70-MNC-0C | 7.01% | 26.89% | 19.88% | 100.00% |
| 60-MNC-0C | 7.36% | 26.56% | 19.20% | 100.00% |
| 50-MNC-0C | 6.70% | 28.46% | 21.76% | 100.00% |
| 25-MNC-0C | 7.13% | 29.36% | 22.23% | 100.00% |
| 0-MNC-0C | 6.96% | 28.86% | 21.90% | 100.00% |
| 100-Mg-0C | 0.93% | 1.05% | 0.12% | 13.07% |
| 90-Mg-0C | 0.93% | 1.15% | 0.22% | 22.69% |
| 80-Mg-0C | 0.81% | 1.09% | 0.28% | 27.05% |
| 75-Mg-0C | 0.81% | 1.09% | 0.27% | 26.59% |
| 70-Mg-0C | 0.79% | 1.04% | 0.26% | 25.27% |
| 60-Mg-0C | 0.73% | 0.95% | 0.23% | 22.60% |
| 50-Mg-0C | 0.89% | 1.05% | 0.16% | 16.81% |
| 25-Mg-0C | 0.81% | 1.11% | 0.29% | 28.40% |
| 0-Mg-0C | 0.80% | 1.08% | 0.28% | 27.18% |

Table 3 presents the concentration of minocycline for each formulation normalized by all peak areas after 1 and 6 days storage at room temperature. The extrapolation calculation assumed that the degradation mechanisms continue at the same mathematical rate as for days 1-6.

TABLE 3

RELATIVE CONCENTRATIONS OF ACTIVE MINOCYCLINE

| SAMPLE DESIGNATION (SEE EXAMPLE 1) | DAY 1 | DAY 6 | CONCENTRATION CHANGE (DIFFERENCE IN CONCENTRATIONS) | EXTRAPOLATED CONCENTRATION AT 18 MONTHS | EXTRAPOLATED CHANGE OVER 18 MONTHS (% OF MINOCYCLINE RELATIVE CONCENTRATION AT DAY 1) |
|---|---|---|---|---|---|
| 100-MNC | 92.59% | 86.13% | −6.47% | 0.03% | −99.96% |
| 90-MNC | 93.57% | 85.14% | −8.44% | 0.00% | −100.00% |

TABLE 3-continued

RELATIVE CONCENTRATIONS OF ACTIVE MINOCYCLINE

| SAMPLE DESIGNATION (SEE EXAMPLE 1) | DAY 1 | DAY 6 | CONCENTRATION CHANGE (DIFFERENCE IN CONCENTRATIONS) | EXTRAPOLATED CONCENTRATION AT 18 MONTHS | EXTRAPOLATED CHANGE OVER 18 MONTHS (% OF MINOCYCLINE RELATIVE CONCENTRATION AT DAY 1) |
|---|---|---|---|---|---|
| 80-MNC | 93.53% | 80.79% | −12.74% | 0.00% | −100.00% |
| 75-MNC | 93.99% | 78.87% | −15.12% | 0.00% | −100.00% |
| 50-MNC | 94.57% | 70.44% | −24.13% | 0.00% | −100.00% |
| 25-MNC | 94.21% | 70.49% | −23.72% | 0.00% | −100.00% |
| 0-MNC | 94.45% | 70.40% | −24.05% | 0.00% | −100.00% |
| 100-Mg | 98.58% | 98.48% | −0.11% | 87.58% | −11.16% |
| 90-Mg | 98.53% | 98.48% | −0.05% | 92.95% | −5.66% |
| 80-Mg | 98.49% | 98.48% | −0.01% | 97.38% | −1.13% |
| 75-Mg | 98.43% | 98.26% | −0.17% | 81.91% | −16.78% |
| 50-Mg | 98.55% | 98.41% | −0.13% | 85.20% | −13.55% |
| 25-Mg | 98.57% | 97.69% | −0.88% | 37.03% | −62.44% |
| 0-Mg | 98.49% | 97.45% | −1.05% | 30.55% | −68.98% |
| 100-MNC-0C | 90.34% | 87.69% | −2.65% | 3.48% | −96.14% |
| 90-MNC-0C | 91.67% | 85.49% | −6.18% | 0.04% | −99.95% |
| 80-MNC-0C | 91.94% | 81.52% | −10.42% | 0.00% | −100.00% |
| 75-MNC-0C | 91.74% | 78.07% | −13.67% | 0.00% | −100.00% |
| 70-MNC-0C | 92.44% | 72.63% | −19.80% | 0.00% | −100.00% |
| 60-MNC-0C | 92.13% | 72.96% | −19.17% | 0.00% | −100.00% |
| 50-MNC-0C | 93.04% | 71.16% | −21.88% | 0.00% | −100.00% |
| 25-MNC-0C | 92.50% | 70.25% | −22.26% | 0.00% | −100.00% |
| 0-MNC-0C | 92.62% | 70.66% | −21.96% | 0.00% | −100.00% |
| 100-Mg-0C | 98.58% | 98.43% | −0.15% | 83.39% | −15.41% |
| 90-Mg-0C | 98.54% | 98.35% | −0.19% | 79.73% | −19.09% |
| 80-Mg-0C | 98.55% | 98.27% | −0.28% | 72.11% | −26.83% |
| 75-Mg-0C | 98.55% | 98.26% | −0.30% | 70.90% | −28.06% |
| 70-Mg-0C | 98.56% | 98.27% | −0.29% | 71.44% | −27.51% |
| 60-Mg-0C | 98.08% | 97.65% | −0.43% | 60.55% | −38.26% |
| 50-Mg-0C | 98.47% | 98.05% | −0.42% | 61.33% | −37.72% |
| 25-Mg-0C | 98.49% | 97.75% | −0.74% | 42.95% | −56.39% |
| 0-Mg-0C | 98.37% | 97.11% | −1.25% | 24.11% | −75.49% |

Propylene glycol is hygroscopic, which typically contributes to the instability of tetracycline class drugs in compositions with significant amounts of propylene glycol. However, as shown in this example, compositions with moderate amounts of propylene glycol (or other similar hygroscopic polyols) are demonstrated to be stable, particularly in the presence of a magnesium salt.

Example 4

Penetration into Ex Vivo Human Skin

Penetration experiments with ex vivo skin tissue were conducted to determine whether active tetracycline class drug penetrates into the skin in sufficient concentrations to achieve a desired therapeutic effect when comprised within compositions comprising a source of magnesium, a monohydric aliphatic alcohol, and a polyol and applied to the skin surface. The penetration into abdominal skin was assessed for four different human donors. Test compositions included mixtures consisting of minocycline hydrochloride, magnesium chloride, ethanol, and propylene glycol.

Solvent mixtures of ethanol (Spectrum Chemicals, Gardena, Calif.), propylene glycol (Spectrum Chemicals, Gardena, Calif.), and 1,8-cineole (Penta International Company, Livingston, N.J.) were prepared in the proportions described in Table 4. To each solvent mixture was added the equivalent of 0.5% (w/w) minocycline hydrochloride (Euticals S.P.A, Origgio, Italy) and 0.5% (w/w) magnesium chloride (Sigma-Aldrich Corp., St. Louis, Mo.).

TABLE 4

SOLVENT MIXTURES FOR SKIN PENETRATION EXPERIMENT

| SAMPLE NUMBER | ETHANOL (% W/W) | PROPYLENE GLYCOL (% W/W) | 1-8,CINEOLE (% W/W) |
|---|---|---|---|
| SP-0 | 0 | 99 | 1 |
| SP-25 | 24.5 | 74.5 | 1 |
| SP-50 | 49.5 | 49.5 | 1 |
| SP-75 | 74.5 | 24.5 | 1 |
| SP-80 | 79.5 | 19.5 | 1 |
| SP-90 | 89.5 | 9.5 | 1 |
| SP-100 | 99 | 0 | 1 |

The compositions were applied to skin samples from four human donors at a dose of 12 mg/cm$^2$. Tissue was maintained in a damp environment to limit drying of the tissue and incubated at 32° C. for 3-4 hours. At the end of the incubation period, excess composition was wiped from the surface using first a dry gauze pad, second a gauze pad soaked with 70% isopropyl alcohol, and finally with a dry gauze pad. Tape stripping was performed to remove the upper layers of the stratum corneum. A six (6) millimeter punch biopsy was taken from within the test area. Minocycline was extracted from each biopsy using acidified methanol. The supernatants were analyzed by high performance liquid chromatography by the same method described in Example 1.

Figure 3:
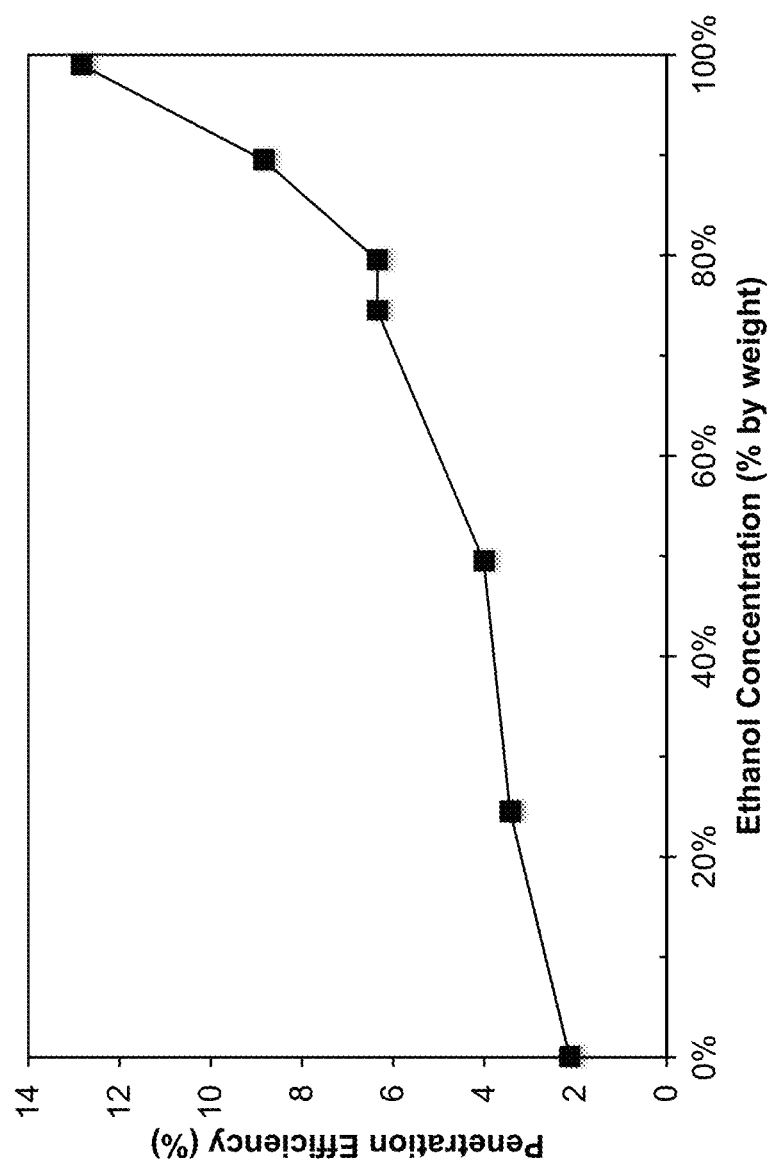
FIG. 3 is a graph illustrating the average penetration efficiency of minocycline into ex vivo human abdominal skin versus ethanol concentration following application of compositions comprising minocycline hydrochloride, magnesium chloride, ethanol, and propylene glycol as described in Example 4.

The average values of the four donor samples for each concentration are presented in FIG. 3. The results demonstrate that the efficiency of penetration increases as propylene glycol is replaced with ethanol; good efficiency of penetration into the skin is also demonstrated.

Example 5

Minimum Inhibitory Concentration (MIC) Measurements—P. Acnes

The antimicrobial activity of minocycline was assessed by measuring the Minimum Inhibitory Concentration (MIC). MIC was also assessed for several other materials and combinations and relative MIC values were calculated as multiples of the minocycline MIC value. MIC was measured using the broth microdilution method as described by the Clinical and Laboratory Standards Institute and represents the lowest concentration of a test material that completely inhibits visible growth of the bacteria in the growth medium.

Test material was dissolved in water, diluted by two-fold serial titrations for a total of 11 concentrations. A 96-well plate was prepared by adding 196 µL of broth medium seeded with a strain of P. acnes ATCC 6919 bacteria. A 4 µL aliquot of a test substance dilution was added to each well to bring the total volume in each well to 200 µL. The test substance concentrations tested ranged from 0.0078 to 16 µg/mL. Plates were incubated at 37° C. for 2 days in anaerobic conditions. 96-well plates were read by a TECAN INFINITE F50 ELISA microplate reader (Männedorf, Switzerland) in absorbance mode with a wavelength of 620 nm. Each well was evaluated for whether growth occurred or was inhibited. The lowest concentration for which growth was inhibited was recorded as the MIC. Each test substance was evaluated in duplicate. The experiment also included controls: vehicle-control (water), untreated control (media only), and a positive control (active reference agent, tetracycline).

MIC values were measured for three test substances: 1) Minocycline (Euticals S.P.A, Origgio, Italy), 2) magnesium chloride anhydrous (Sigma-Aldrich Corp., St. Louis, Mo., part number M8266), and 3) a mixture of minocycline and magnesium chloride anhydrous in a 1:1.5 ratio (w/w).

The results showed that minocycline mixed with magnesium chloride had a MIC value of 0.5 micrograms per milliliter. Minocycline alone had a MIC value of 0.125 micrograms per milliliter. Magnesium chloride alone did not inhibit growth at any of the concentrations tested.

Thus, the results indicate that the magnesium chloride interacts with the minocycline to increase the MIC of the minocycline. Additional HPLC measurements show that this reduction is not due to a degradation of the active minocycline through epimerization. Instead, the magnesium appears to be strongly interacting with minocycline.

Example 6

MALDI-TOF Demonstration of Preferential Location of Minocycline in Oily Tissue and Penetration into Dermal Tissue Topical drug compositions must penetrate into the desired tissue or material in order to have an intended effect. For dermatological diseases, such as acne, penetration into skin, sebocytes, and/or sebum is required. Ideally, the concentration of the topical drug is higher in selected locations in comparison to areas that are less important from a pharmacological perspective, thus potentially increasing effectiveness and reducing side effects for a given dose.

A topical minocycline composition was applied to the surface of ex vivo human facial skin and a vertical cross section of the skin was imaged using Matrix-Assisted Laser Desorption/Ionization Time-of-Flight (MALDI-TOF) mass spectrometry. The data show that not only does the minocycline penetrate into the skin tissue, but that larger concentrations are found in sebaceous glands and in sebum-rich regions.

MALDI-TOF mass spectrometry is a method that comprises the controlled ablation of tissue that has been coated in a matrix material with an ultraviolet laser. This triggers the ablation and desorption of the sample. The resulting ionized particles are ejected into a gas phase mass spectrometer to measure the mass spectral signature of the ablated material. The ablation step uses a nitrogen laser with a wavelength of 377 nm, which is very strongly absorbed by chemical matrix applied to a skin tissue sample. The laser has a high intensity and short pulse duration (~1 millisecond) leading to ablation of the surface matrix layer at each location of focused laser energy (x-y directions). The skin tissue sample can be precisely moved using a controlled x-y translation stage. Thus, a precise two-dimensional "image" can be created of the skin tissue sample.

The use of time-of-flight mass spectrometry allows precise identification of the presence of selected materials at each two-dimensional location within the skin tissue sample. For example, minocycline has a molecular mass to charge ratio (i.e. "m/z") of approximately 458.4 and a component of sebum that has a m/z value of approximately 494.36. Within the skin, phosphatidylcholine, which has a m/z value of 756.1, is primarily located within the sebaceous glands. Thus, these m/z values can be used to identify sebum-rich regions and sebaceous gland locations in the skin with MALDI-TOF mass spectrometry. These can be used to assess whether the locations of high minocycline concentrations are correlated with sebum-rich regions and/or sebaceous glands. In this way, the relative concentrations of minocycline in sebum-rich regions and/or sebaceous glands can be determined.

Fresh human facial skin sections were placed in a 32° C. incubator for 30 minutes on a piece of gauze dampened with saline solution (0.9% sodium chloride solution). One of the test compositions was applied to the skin surface with a controlled mass of composition per unit area. The tissue samples were incubated for 24 hours at 32° C. in a humid environment. At the end of the incubation period, excess composition was wiped from the surface using first a dry gauze pad, second a gauze pad soaked with 70% isopropyl alcohol, and finally with a dry gauze pad. Two six (6) millimeter punch biopsies were taken from within the test area. Two additional six (6) millimeter punch biopsies were taken from outside the test area to serve as controls. The punch biopsies were wrapped in aluminum foil and frozen using liquid nitrogen until they were ready for MALDI-TOF mass spectrometry analysis.

Just prior to MALDI-TOF mass spectrometry analysis, the frozen tissue was sliced into 12-micrometer (µm) vertical sections using a cryostat. Serial sections were taken so that comparisons could be made between images from MALDI-TOF mass spectrometry analysis and tissue stained with hematoxylin and eosin (H&E). For the sections to be analyzed with MALDI-TOF mass spectrometry, a solution of 2,5-dihydroxybenzoic acid (DHB) was applied to the tissue using a 50% acetonitrile (ACN) airbrush. MALDI-TOF mass spectrometry analysis (Protea Biosciences, Inc., Morgantown, W. Va.) was performed on the resulting tissue with mass spectrometry being performed by a time-of-flight mass spectrometer (ultrafleXtreme, Bruker Daltonics, Inc., Billerica, Mass.) in reflection positive ion mode.

Two different compositions were assessed. The first composition contained 67.77% (w/w) ethanol (Spectrum Chemicals, Gardena, Calif.), 18.59% (w/w) propylene glycol (Spectrum Chemicals, Gardena, Calif.), 9.83% (w/w) 1,8-cineole (Spectrum Chemicals, Gardena, Calif.), 1.03% (w/w) hydroxypropyl cellulose (Ashland, Inc., Covington, Ky.), 1.34% (w/w) ODS-modified silica (made according to the method described in U.S. patent application Ser. No. 14/532,987), 0.99% (w/w) minocycline base (Hovione Inter Ltd., Loures, Portugal), and 0.45% (w/w) magnesium chloride (Sigma-Aldrich Corp., St. Louis, Mo.).

The second composition contained 68.03% (w/w) ethanol (Spectrum Chemicals, Gardena, Calif.), 20.15% (w/w) propylene glycol (Spectrum Chemicals, Gardena, Calif.), 10% (w/w) 1,8-cineole (Spectrum Chemicals, Gardena, Calif.), 1.39% (w/w) hydroxypropyl methylcellulose (Dow Chemicals, Pittsburgh, Calif.), 0.30% (w/w) minocycline base (Hovione Inter Ltd., Loures, Portugal), and 0.13% (w/w) magnesium chloride (Sigma-Aldrich Corp., St. Louis, Mo.).

Figure 4A:
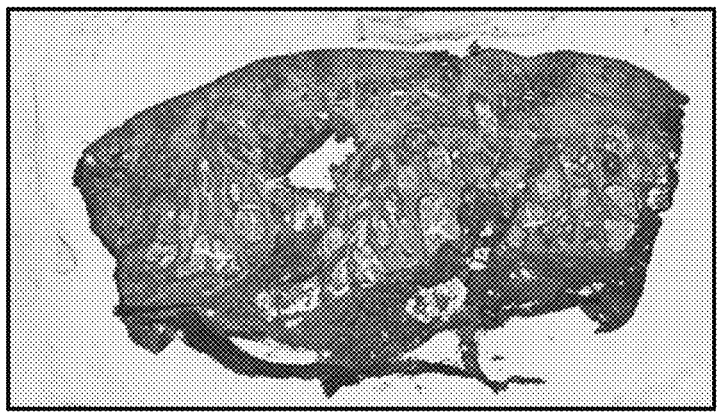
FIGS. 4A-C present results of the "Control" tissue from Example 6.
Figure 4B:
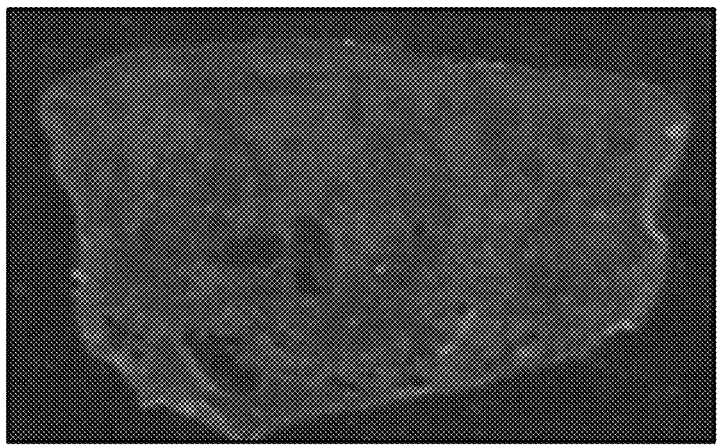
Figure 4C:
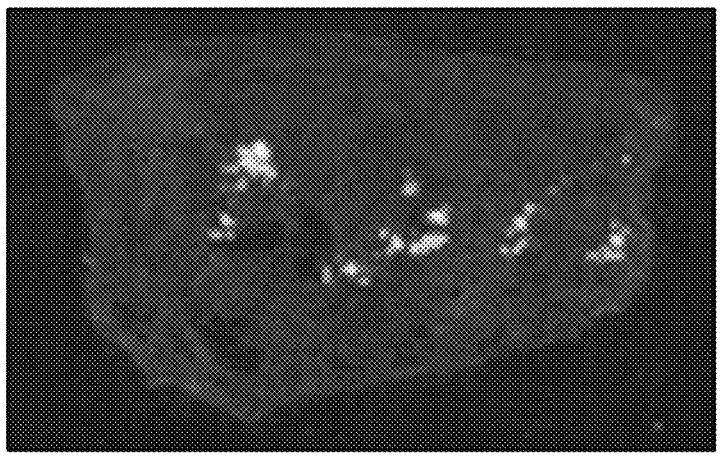
Figure 5A:
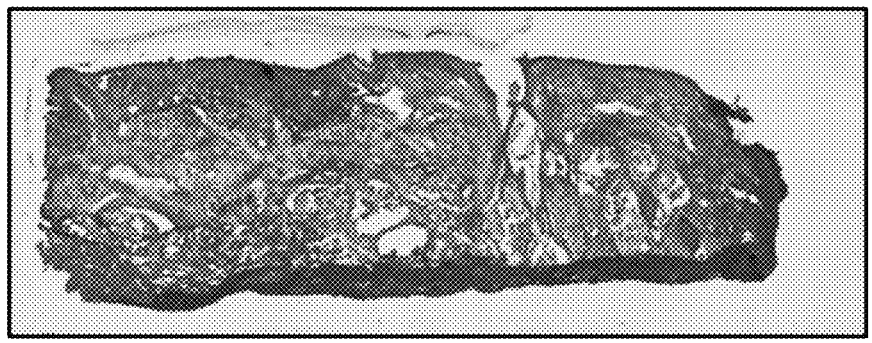
FIGS. 5A-C present the results of the "Treated" tissue from Example 6.
Figure 5B:
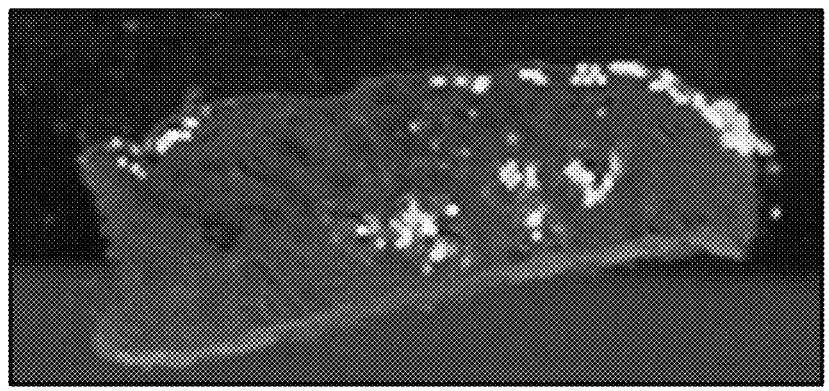
Figure 5C:
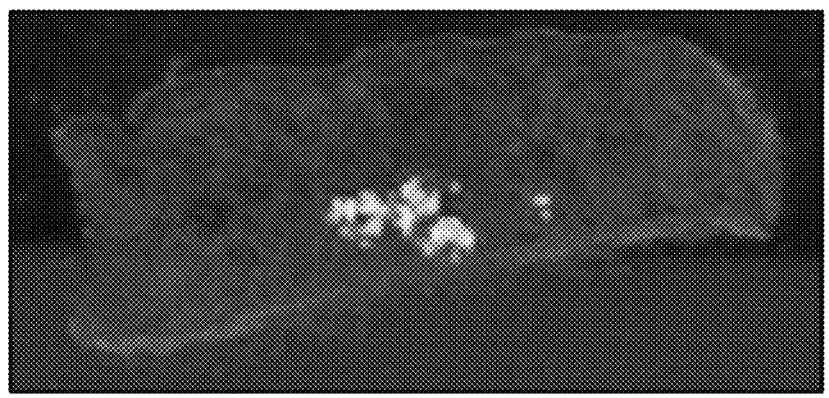

FIGS. 4a and 5a show H&E-stained skin sections from the control tissue (i.e. skin sample that did not have the test composition applied) and first "treated" tissue (i.e. skin sample to which the first test composition was applied ex vivo). Both the control tissue and first treated tissue were from the same human donor. FIGS. 4b, 4c, 5b, and 5c show images constructed from the data collected during MALDI-TOF mass spectrometry analysis. FIGS. 4b and 4c show images from the control tissue. FIGS. 5b and 5c show images from the first treated tissue. FIGS. 4b and 5b show images constructed from MALDI-TOF mass spectrometry data corresponding to a m/z value of 458.5, which is associated with minocycline. In these images, the lighter tones correspond to higher minocycline concentrations. FIGS. 4c and 5c show images constructed from MALDI-TOF mass spectrometry data corresponding to a m/z value of 494.36, which is associated with a component of sebum. In these images, the lighter tones correspond to higher sebum concentrations. Based on a comparison of FIGS. 5a, 5b, and 5c, minocycline was shown to penetrate into the skin, with heavier concentrations of minocycline located in both the epidermis and sebum-rich regions of the skin, while no minocycline was detected in the control tissue.

The second similar (uncontrolled) experiment confirmed the association between higher minocycline concentrations and sebaceous glands by using MALDI-TOF mass spectrometry to detect minocycline at a m/z value of 458.3 and phosphatidylcholine at a m/z value of 756.1.

Thus, the results show that locations of high concentration of sebaceous lipid and/or phosphatidylcholine are strongly correlated with locations of high concentration of minocycline. Thus, the experiment shows that the minocycline penetrates into the skin tissue sample and that minocycline strongly partitions into sebum-rich regions and sebaceous glands of the skin. Control samples without applied test composition show no detectable minocycline.

Example 7

Penetration of Minocycline and
Magnesium-Stabilized Minocycline and Partitioning
in Lipid-Rich Portions of the Skin Fluorescence microscopy of histological sections can be used to demonstrate the location of many tetracycline class drugs within skin layers and tissue structures. Different dermatological conditions or diseases may benefit from preferential targeting of the drug to different locations within the skin. For example, treatment of acne may be beneficially improved if a tetracycline class drug is delivered to the sebaceous gland. On the other hand, treatment of psoriasis may be beneficially improved if the tetracycline class drug is delivered to the dermis.

Two experiments were performed to identify localization of the compositions within the skin. Two compositions were prepared. The first composition contained 64.89% (w/w) ethanol (Spectrum Chemicals, Gardena, Calif.), 17.8% (w/w) propylene glycol (Spectrum Chemicals, Gardena, Calif.), 9.41% (w/w) 1,8-cineole (Penta International Company, Livingston, N.J.), 0.99% hydroxypropyl cellulose (Ashland, Inc., Covington, Ky.), 4.2% (w/w) ODS-modified silica (made according to the method described in U.S. patent application Ser. No. 14/532,987), 0.1% (w/w) sodium meta-bisulfate (Spectrum Chemicals, Gardena, Calif.), 1.0% (w/w) minocycline hydrochloride (RIA International, East Hanover, N.J.) (approximately 0.86% (w/w) minocycline free-base-equivalent), and 1.61% (w/w) magnesium chloride (Sigma-Aldrich Corp., St. Louis, Mo.). The second composition contained 61.97% (w/w) ethanol, 17% (w/w) propylene glycol, 8.99% (w/w) 1,8-cineole, 0.94% (w/w) hydroxypropyl cellulose, 4.0% (w/w) ODS-modified silica, and 0.18% (w/w) sodium meta-bisulfate, 3.84% (w/w) minocycline hydrochloride (approximately 3.3% (w/w) minocycline free-base-equivalent), and 3.08% (w/w) magnesium chloride.

Approximately 50 mg/cm$^2$ of each of these compositions was applied to ex vivo human tissue samples and incubated for 24 hours. The composition was then cleaned from the skin, embedded in Optimal Cutting Temperature compound (OCT), frozen, and sliced using a cryostat into transverse histological cross-sections approximately 15 micrometers (μm) thick. The histological sections were examined using fluorescence microscopy. The excitation wavelength range was 340-480 nm and the emission wavelength range was 620-700 nm.

Figure 6:
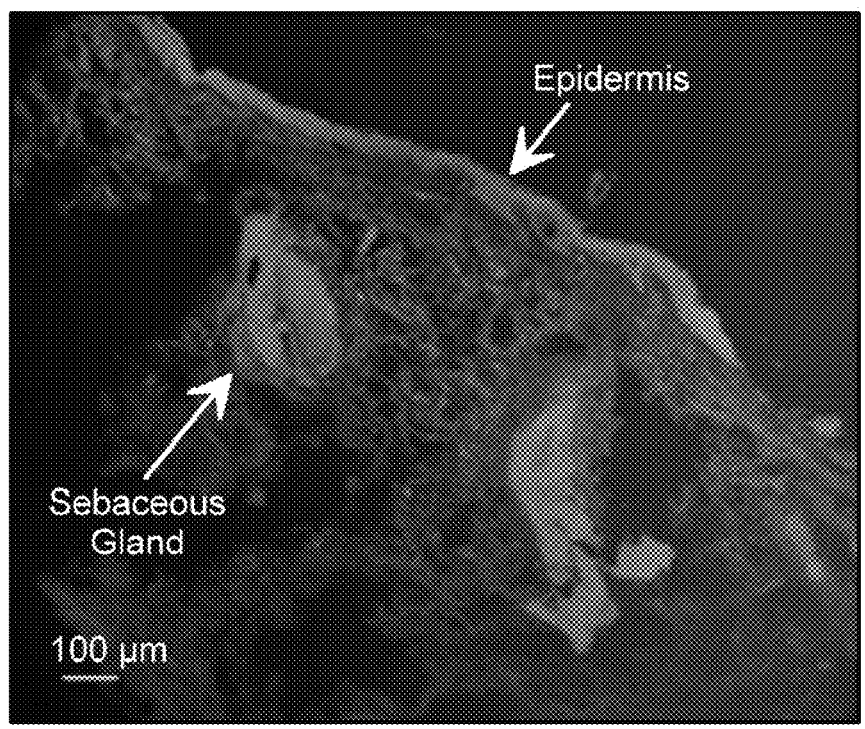
FIG. 6 is a fluorescence micrograph showing minocycline within a cross section of human skin tissue as described in Example 7.

The first composition was applied to the upper skin surface (i.e. stratum corneum) of the tissue illuminated in FIG. 6. It shows minocycline penetrated to the stratum corneum, viable epidermis, dermal epidermal junction, dermis, hair follicle, and sebaceous gland. The brighter (pink) areas of the micrograph indicate fluorescence of the minocycline. Minocycline was concentrated in the upper epidermis and sebaceous gland. This targeted delivery of minocycline to the sebaceous gland shows that the composition is advantageous for the treatment of acne.

Figure 7A:
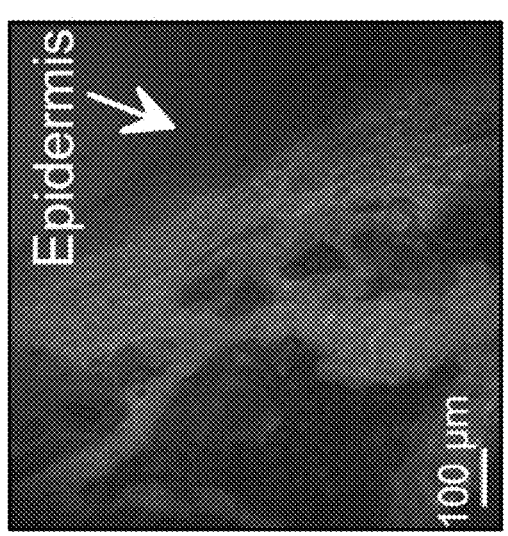
FIG. 7A-C are fluorescence micrographs showing minocycline within transverse sections of human skin tissue as described in Example 7.
Figure 7B:
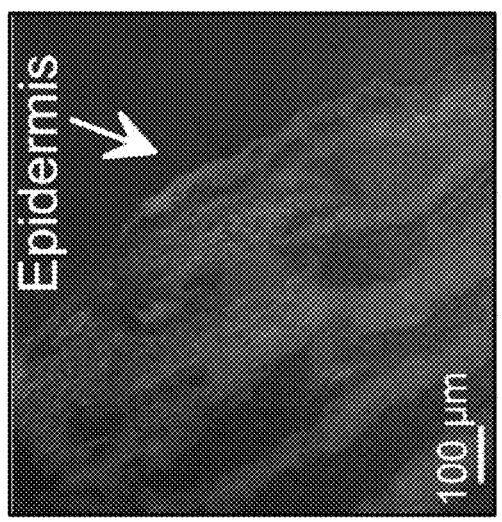
Figure 7C:
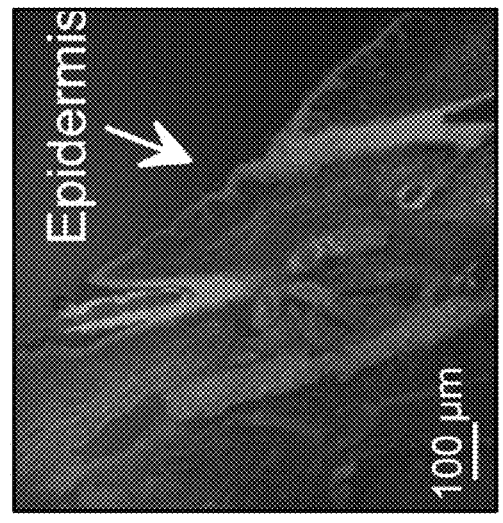

A second experiment evaluated how the concentration of minocycline within the composition affected the uptake of minocycline. The first and second compositions were applied to skin samples and incubated and prepared as in the first experiment. They were then compared to an untreated skin tissue sample from the same donor. The fluorescent micrographs are presented in FIGS. 7a-c. FIG. 7a shows the untreated histological section, FIGS. 7b and 7c show the histological sections from the skin treated with the first and second compositions, respectively. The increased concentration of minocycline shows a dose dependent increase of minocycline within the skin and at sebaceous glands.

The results of these two experiments demonstrate that in addition to delivering a tetracycline class drug into all layers of the skin, the tetracycline class drug is preferentially delivered to both the sebaceous gland and the stratum corneum. Both of these structures are lipid-rich, indicating a preferential delivery of the tetracycline class drug to lipid-rich tissues, both on and within the skin. Since the tetracycline class drug is delivered preferentially to the sebaceous gland and minocycline is known to be beneficial for the treatment of acne (when taken orally), these results demonstrate the utility of the instant compositions for the treatment of acne.

Example 8

In Vivo Rat Repeat Dose Study Skin Irritation and Staining

Mixtures of a monohydric aliphatic alcohol such as ethanol, and a polyol such as propylene glycol, can be potentially irritating when applied to skin in high concentrations, such as in compositions comprising 50-99.9% (w/w) of these two materials, compositions comprising 70-99% (w/w) of these two materials, or compositions comprising 90-99% (w/w) of these two materials. This example evaluated whether such irritation results for compositions such as provided herein including a tetracycline class drug and a source of magnesium.

Both skin uptake and blood plasma levels of minocycline hydrochloride were assessed following a 14-day treatment with a placebo formulation or with one of four formulations containing approximately 0.5%, 1%, 2%, or 4% by weight minocycline as described in Table 5 below. Compositions were prepared in the proportions described in Table 5.

TABLE 5

COMPOSITIONS USED (ALL PERCENTAGES ARE LISTED BY WEIGHT (I.E. (W/W))

| | COMPOSITION NUMBER | | | | |
|---|---|---|---|---|---|
| | 0-B | 0.5-B | 1-B | 2-B | 4-B |
| Minocycline hydrochloride | 0% | 0.6% | 1.2% | 2.3% | 4.6% |
| Hydroxypropyl cellulose | 0.6% | 0.6% | 0.6% | 0.6% | 0.6% |
| Magnesium chloride (anhydrous) | 0% | 0.6% | 1.2% | 2.3% | 4.6% |
| Ethanol (anhydrous) | 78.2% | 77.0% | 75.8% | 68.6% | 59.0% |
| Propylene Glycol | 20.0% | 20.0% | 20.0% | 25.0% | 30.0% |
| 1,8-Cineole | 1.0% | 1.0% | 1.0% | 1.0% | 1.0% |
| Sodium meta-bisulfate | 0.2% | 0.2% | 0.2% | 0.2% | 0.2% |

Ten male Sprague-Dawley rats were evaluated for irritation and scored. Patches of skin on either the anterior or posterior of each rat (two 4 cm² areas) were shaved at the beginning of the experiment and the rats were randomly divided into 5 treatment groups (each receiving application of one of the formulations listed in Table 5 (0-B, 0.5-B, 1-B, 2-B, or 4-B, corresponding to placebo and about 0.5%, about 1.0%, about 2.0% and about 4.0% minocycline equivalent base, respectively), applied at a dose of either 10 mg or 20 mg per test area. Each composition was applied daily to each of two shaved patches on a pair of rats, for a total of 4 test sites per composition. The rats received either 10 mg or 20 mg of one composition in each 4 cm² area (i.e., 2.5 mg/cm² or 5 mg/cm²) over a 14-day period. Following each 24-hour treatment, the application site was cleansed with 2% soap solution followed by 1×PBS soaked gauze pads, and then dried. White light images of the animals were taken daily, as were UV images. Observations were made up to and beyond 72 hours. Daily application of each of the compositions (0.5%, 1%, 2% and 4% minocycline free base equivalent) at amounts up to 20 mg per 4 cm² area did not produce any significant erythema, redness, irritation, and/or edema. No abnormal weight changes were observed in any treatment group; nor was minocycline detected in the blood. Thus, in vivo studies in rats for skin irritation showed no significant erythema or edema at or beyond the treatment site.

Additionally, staining of the skin was not observed for any of the rats at the end of the 14-day repeat application study and no residual fluorescence was noted after the composition was rinsed from the skin at the end of the experiment. This indicates that the composition is non-staining, despite relatively high concentrations of applied minocycline (up to 5 mg/cm² of composition).

Finally, efficiency of skin uptake for the formulation series was determined. Efficiency calculated for the 10 mg per 4 cm² and 20 mg per 4 cm² patches was very similar (~5-8.5% efficiency) for the 0.5%, 2% and 4% minocycline formulations. The 1% minocycline formulation displayed a higher efficiency at both treatment amounts, of approximately 12.9% for the 10 mg per 4 cm² patch and 19.6% for the 20 mg per 4 cm² patch. The 10 mg per 4 cm² patch group for the 1% formulation easily satisfies the penetration requirement for achieving a local concentration in the skin indicative of a therapeutic dose. At approximately 5.3 µg/cm², the minocycline uptake for the 1% formulation and the 10 mg per 4 cm² patch translates into 0.95 µg/g of minocycline in skin, which is at least an order of magnitude above the minimum inhibitory concentration (MIC) for inhibiting *P. acnes*.

Example 9

Fluorescence Intensity as a Function of Magnesium Concentration

As shown previously, magnesium contributes to the stabilization of the minocycline within the composition. This experiment is aimed at determining the optimal level of magnesium in a composition. Fluorescence intensity can be used to estimate the approximate ratio beyond which adding further magnesium does not significantly improve stability and/or solubility. A fluorescence intensity study was performed to evaluate the concentration of magnesium at which the rate of increase in fluorescence following the addition of further magnesium dropped significantly and/or abruptly.

A base solution of 77.59% (w/w) ethanol anhydrous, 21.2% (w/w) propylene glycol, 0.76% (w/w) minocycline hydrochloride (approximately 0.66% (w/w) minocycline FBE), 0.39% (w/w) hydroxypropyl cellulose HF (HPC HF), 0.06% (w/w) sodium metabisulfite. Magnesium chloride anhydrous was added to 4 mL (3.13 g) of the base solution at the concentration is 4.4% (w/w) to create a solution with a molality of magnesium chloride of 464.3 mmol/kg. The molar ratio between magnesium and minocycline was 30.18. The prepared solution was serially diluted 2-fold with the base solution to form preparations of the base solution with magnesium chloride at different molar ratios of magnesium to minocycline: 0, 0.47, 0.94, 1.89, 3.77, 7.55, 15.09, and 30.18.

The results of fluorescence measurements and of measurements of 4-epi-minocycline concentration after 7 days at 50° C. are presented in Table 6.

TABLE 6

COMPOSITIONS FOR FLUORESCENCE EXPERIMENT (ALL PERCENTAGES ARE LISTED BY WEIGHT (I.E., W/W))

| MNC*HCL (%) | MgCl$_2$ (%) | MOLAR RATIO [MG]/[MNC] | FLUO-RES-CENCE | CHANGE IN 4-EPI-MINO-CYCLINE OVER 7 DAYS @ 50° C. |
|---|---|---|---|---|
| 0.76 | 4.42 | 30.18 | 963 | 0.19 |
| 0.76 | 2.21 | 15.09 | 818 | 0.21 |
| 0.76 | 1.11 | 7.55 | 679 | 0.27 |
| 0.76 | 0.55 | 3.77 | 615 | 0.36 |
| 0.76 | 0.28 | 1.89 | 416 | 0.49 |
| 0.76 | 0.14 | 0.94 | 233 | 0.73 |
| 0.76 | 0.07 | 0.47 | 73 | 1.82 |
| 0.76 | 0.00 | 0.00 | 0 | 26.04 |

MNC = minocycline

Figure 8A:
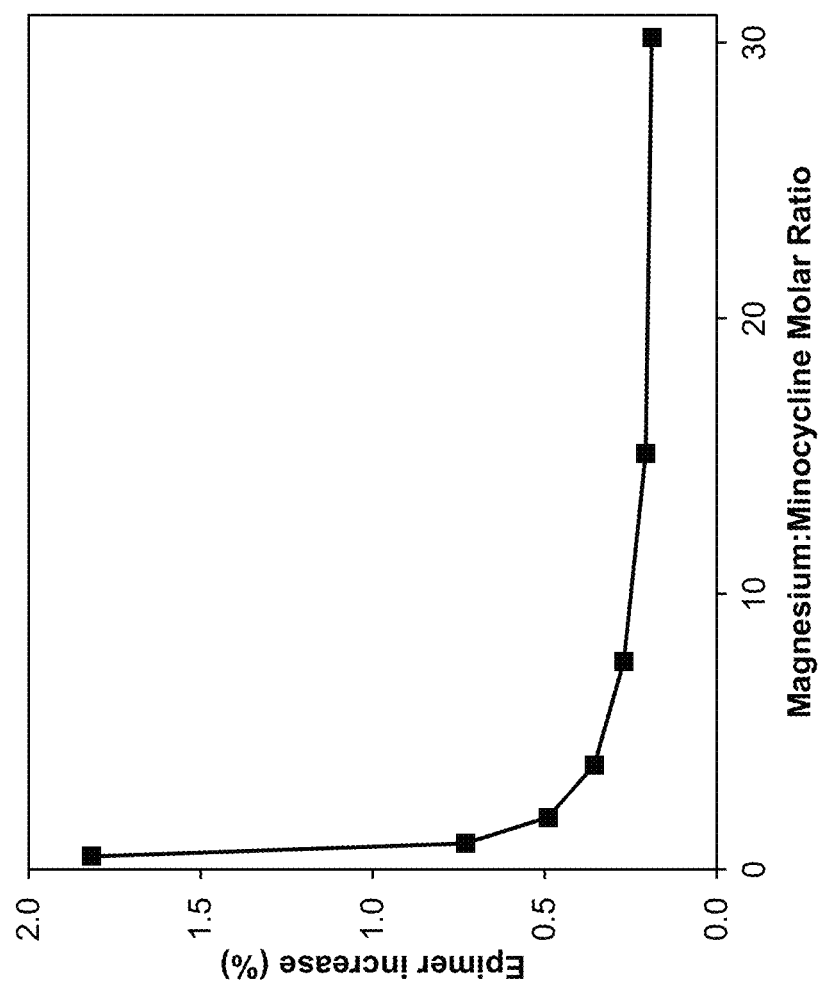
FIG. 8A is a graph illustrating the increase in relative 4-epi-minocycline concentration as a function of the molar ratio of magnesium to minocycline free base equivalent following 7 days of forced degradation at 50° C. as described in Example 9.
Figure 8B:
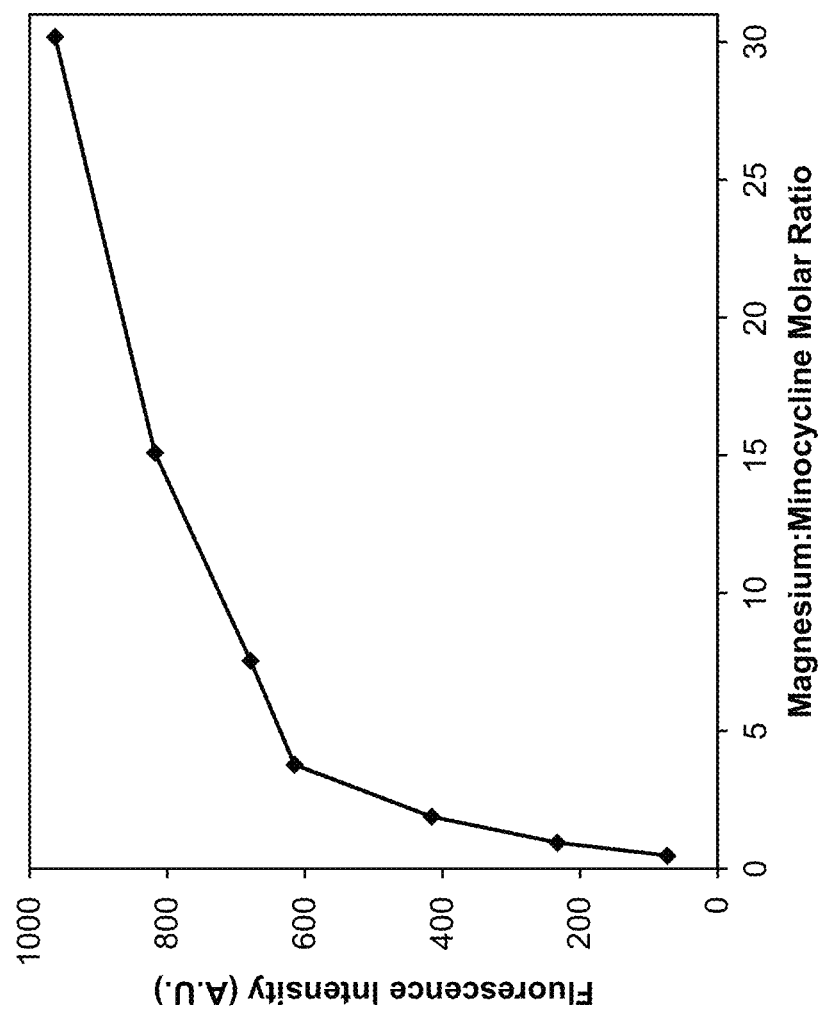
FIG. 8B is a graph demonstrating the fluorescence (A.U.) of exemplary minocycline compositions as a function of the molar ratio of magnesium to minocycline free-base equivalent as described in Example 9.

The fluorescence intensity of each of the resulting compositions was measured using a fluorescence spectrometer with an excitation wavelength of 380 nm. Fluorescence emission intensity was assessed at a wavelength of 473 nm. The fluorescence of the samples without magnesium chloride was lower than the detection limit of the measurement apparatus. As shown in FIG. 8b, the fluorescence intensity increases sharply as the molar ratio between magnesium and minocycline increases from 0 to about 3.8. For molar ratios above about 3.8, the rate of increase as a function of molar ratio is significantly lower than the corresponding rate of increase for molar ratios below about 3.8. Increasing the amount of magnesium chloride above this level does not continue to increase the fluorescence of the composition as significantly. Since fluorescence intensity is correlated with the rigidity of tetracycline class drugs, such as minocycline, in a local environment, the data indicate that the minocycline-magnesium complex formation in this composition is made more rigid as the molar ratio is increased to about 3.8 in the mixture. In the other words, the structural rigidity of minocycline continues to improve significantly beyond a molar ratio for magnesium to minocycline of 1:1 or 2:1 and does not reach its primary plateau until the molar ratio exceeds about 3.8 for this composition. So, the molar ratio of 3.8:1 may differ for other compositions constructed according to the teachings herein.

The stability of minocycline was assessed by monitoring epimer formation in each of the prepared samples described above. The amount of the epimer 4-epi-minocycline was measured via HPLC analysis prior to and after forced thermal degradation in an oven at 50° C. for 7 days. The ratio between the epimer peak area and the sum of the epimer peak area and the active minocycline peak area gives an indication of the stability of the minocycline in the each composition. Epimer formation was calculated as the difference in this ratio for the samples collected prior to and after the forced thermal degradation. Higher molar ratios of magnesium to minocycline corresponded to lower epimer formation. Adding magnesium above a molar ratio of about 3.8 reduces the epimer formation. However, the amount by which the epimer formation is reduced diminishes for higher molar ratios.

The amount of fluorescence is indicative of the rigidity of the tetracycline class drug. FIG. 8a is a graph of the change in the concentration of 4-epi-minocycline after 7 days of forced degradation at 50° C. Change in the concentration of 4-epi-minocycline is an indicator of stability of minocycline in composition. Adding magnesium chloride up to a molar ratio of about 3.8:1 with minocycline increases the rigidity of the minocycline in the composition and thus improves the stability by reducing the reactivity of the minocycline. Adding magnesium chloride above this concentration enhances stability less. So, a molar ratio of approximately 3.8:1 would be a good concentration around which to begin an optimization of this particular composition.

The stoichiometry of a magnesium-minocycline has been proposed to be 1:1 or 2:1. These proposed ratios, however, may not apply when the magnesium and minocycline are in a non-aqueous solvent mixture in which a eutectic is formed, such as in the topical composition described herein. Differences in minocycline fluorescence as a function of magnesium concentration reflect differences in chemical energy levels and differences in ionic interactions. The formation of a complex between minocycline and magnesium can limit epimerization reactions and thus promote stability. These methods and results suggest the optimal molar ratio between minocycline and magnesium ion exceeds 2:1 in the present solvent system. The stoichiometry and precise ratio will depend on the particular components employed in a composition.

Example 10

6-Month Stability Measurement

Multiple samples of an exemplary composition were tested for potency after storage for 6 months at room temperature. The initial composition contained consisted of 69.36% (w/w) ethanol, 17.92% (w/w) propylene glycol, 9.41% (w/w) 1,8-cineole, 1.0% (w/w) minocycline hydrochloride (about 0.86% (w/w) minocycline free-base-equivalent), 1.61% (w/w) magnesium chloride, 0.6% (w/w) hydroxypropyl cellulose HF, and 0.1% (w/w) sodium metabisulfite. The amount of minocycline was measured using high performance liquid chromatography for the initial samples and for samples after 6-months of storage at room temperature conditions in sealed vials. For the initial samples, the minocycline peak contained about 100.0% of the minocycline in the composition and minocycline represented about 97.3% when normalized by all peak areas. The 4-epi-minocycline peak for the initial samples was about 0.54% when normalized by all peak areas. Note that the minocycline and 4-epi-minocycline peak percentages add up to more than 100% due to small errors in calibration curves. After 6 months of storage, the active minocycline peak represented 97.1% of the minocycline in the composition and minocycline represented about 95.0% when normalized by all peak areas. Thus, these measurements indicated that after 6 months of storage at room temperature, the active minocycline was reduced by about 2.9% of the minocycline in the composition and about 2.3% when normalized by all peak areas. The 4-epi-minocycline peak for samples after 6 months of storage at room temperature was about 1.68% when normalized by all peak areas, representing an increase in the 4-epi-minocycline peak of about 1.1% after 6 months of storage at room temperature.

Example 11

Topical Compositions

Table 7 provides additional illustrative topical compositions. The compositions are prepared by mixing the various components as previously described. As mentioned above, these exemplary compositions are in no way intended to limit the scope of what the inventors regard as their invention. Each column lists the percentage by weight of the component listed at the left side of each row in the composition. Each column adds to a total of 100%.

TABLE 7

EXEMPLARY COMPOSITIONS

| | \multicolumn{10}{c}{EXEMPLARY COMPOSITION #} |
|---|---|---|---|---|---|---|---|---|---|---|
| | 1 | 2 | 3 | 4 | 5 | 6 | 7 | 8 | 9 | 10 |
| Tetracycline class drug | | | | | | | | | | |
| Minocycline hydrochloride | 0.3 | 0.6 | 1.2 | 2.3 | 4.6 | 1.2 | 1.2 | 4.6 | 4.6 | 4.6 |
| Magnesium source | | | | | | | | | | |
| Magnesium chloride anhydrous | 0.3 | 0.6 | 1.2 | 2.3 | 4.6 | 1.2 | 1.2 | 4.6 | 4.6 | 4.6 |
| Monohydric aliphatic alcohol | | | | | | | | | | |
| Ethanol | 78.6 | 78.0 | 76.8 | 69.6 | 60.0 | 75.8 | 76.0 | 60.6 | 60.4 | 55.4 |
| Polyol | | | | | | | | | | |
| Propylene glycol | 20 | 20 | 20 | 25 | 30 | 20 | 20 | 30 | 30 | 30 |
| Other components | | | | | | | | | | |
| Sodium metabisulfate | 0.2 | 0.2 | 0.2 | 0.2 | 0.2 | 0.2 | — | 0.2 | 0.2 | 0.2 |
| Hydroxypropyl cellulose HF (HPC HF) | 0.6 | 0.6 | 0.6 | 0.6 | 0.6 | 0.6 | 0.6 | — | 0.2 | 0.2 |
| Cineole | — | — | — | — | — | 1 | 1 | — | — | 5 |

| | \multicolumn{10}{c}{EXEMPLARY COMPOSITION #} |
|---|---|---|---|---|---|---|---|---|---|---|
| | 11 | 12 | 13 | 14 | 15 | 16 | 17 | 18 | 19 | 20 |
| Tetracycline class drug | | | | | | | | | | |
| Minocycline hydrochloride | — | — | — | — | — | 1.2 | 1.2 | 1.2 | 1.2 | 1.2 |
| Minocycline base | 1.2 | — | — | — | — | — | — | — | — | — |
| Tetracycline hydrochloride | — | 1.2 | — | — | — | — | — | — | — | — |
| Doxycycline | — | — | 1.2 | — | — | — | — | — | — | — |
| Tigecycline | — | — | — | 1.2 | — | — | — | — | — | — |
| Lymecycline | — | — | — | — | 1.2 | — | — | — | — | — |
| Magnesium source | | | | | | | | | | |
| Magnesium chloride anhydrous | 1.2 | 1.2 | 1.2 | 1.2 | 1.2 | — | — | — | 1.2 | 1.2 |
| Magnesium chloride hexahydrate | — | — | — | — | — | 2.6 | — | — | — | — |
| Magnesium acetate | — | — | — | — | — | — | 1.2 | — | — | — |
| Magnesium nitrate | — | — | — | — | — | — | — | 0.4 | — | — |
| Monohydric aliphatic alcohol | | | | | | | | | | |
| Ethanol | 76.8 | 76.8 | 76.8 | 76.8 | 76.8 | 75.4 | 76.8 | 77.6 | 76.8 | 76.8 |
| Polyol | | | | | | | | | | |
| Propylene glycol | 20 | 20 | 20 | 20 | 20 | 20 | 20 | 20 | — | — |
| Dipropylene glycol | — | — | — | — | — | — | — | — | 20 | — |
| Glycerol | — | — | — | — | — | — | — | — | — | 20 |
| Other components | | | | | | | | | | |
| Sodium metabisulfate | 0.2 | 0.2 | 0.2 | 0.2 | 0.2 | 0.2 | 0.2 | 0.2 | 0.2 | 0.2 |
| Hydroxypropyl cellulose HF (HPC HF) | 0.6 | 0.6 | 0.6 | 0.6 | 0.6 | 0.6 | 0.6 | 0.6 | 0.6 | 0.6 |

TABLE 7-continued

EXEMPLARY COMPOSITIONS

| EXEMPLARY COMPOSITION # | | | | | | | | | | |
|---|---|---|---|---|---|---|---|---|---|---|
| | 21 | 22 | 23 | 24 | 25 | 26 | 27 | 28 | 29 | 30 |
| Tetracycline class drug | | | | | | | | | | |
| Minocycline hydrochloride | 1.2 | 1.2 | 0.1 | 0.3 | 0.6 | 0.3 | 0.6 | 0.3 | 0.6 | 1.2 |
| Magnesium source | | | | | | | | | | |
| Magnesium chloride anhydrous | 1.2 | 0.5 | 1.8 | 0.3 | 0.6 | 0.3 | 0.6 | 0.3 | 0.6 | 1.2 |
| Monohydric aliphatic alcohol | | | | | | | | | | |
| Ethanol | 76.8 | 77.5 | 77.3 | — | — | — | — | — | — | — |
| Isopropanol | — | — | — | 78.6 | 78.0 | — | — | — | — | — |
| Propyl alcohol | — | — | — | — | — | — | — | 78.6 | 78.0 | 76.8 |
| 1-butyl alcohol | — | — | — | — | — | 78.6 | 78.0 | — | — | — |
| Polyol | | | | | | | | | | |
| Propylene glycol | 20 | 20 | 20 | 20 | 20 | 20 | 20 | 20 | 20 | 20 |
| Other components | | | | | | | | | | |
| Sodium metabisulfate | 0.2 | 0.2 | 0.2 | 0.2 | 0.2 | 0.2 | 0.2 | 0.2 | 0.2 | 0.2 |
| Hydroxypropyl cellulose HF (HPC HF) | — | 0.6 | 0.6 | 0.6 | 0.6 | 0.6 | 0.6 | 0.6 | 0.6 | 0.6 |
| Hydroxypropyl methyl cellulose (HPMC) | 0.6 | — | — | — | — | — | — | — | — | — |

| EXEMPLARY COMPOSITION # | | | | | | | | | | |
|---|---|---|---|---|---|---|---|---|---|---|
| | 31 | 32 | 33 | 34 | 35 | 36 | 37 | 38 | 39 | 40 |
| Tetracycline class drug | | | | | | | | | | |
| Minocycline hydrochloride | 0.1 | 0.1 | 0.25 | — | 0.1 | — | — | — | 10 | 5 |
| Minocycline base | — | — | — | — | — | — | — | 0.5 | — | — |
| Tetracycline hydrochloride | — | — | 0.25 | — | — | 0.25 | — | — | — | — |
| Doxycycline | — | 0.1 | — | 0.5 | — | — | 0.3 | 0.5 | — | — |
| Tigecycline | — | — | — | — | — | 0.25 | — | — | — | — |
| Lymecycline | — | — | — | 0.5 | — | — | — | — | — | — |
| Magnesium source | | | | | | | | | | |
| Magnesium chloride anhydrous | 0.5 | 0.6 | — | 4 | 0.9 | — | — | 4 | 5 | — |
| Magnesium chloride hexahydrate | — | — | — | — | — | 1.2 | 0.2 | — | — | 15 |
| Magnesium acetate | — | — | 0.2 | — | — | — | — | — | — | — |
| Magnesium sulfate | — | — | — | — | — | — | 0.1 | — | — | — |
| Monohydric aliphatic alcohol | | | | | | | | | | |
| Ethanol | — | 88.7 | 98.5 | 64.2 | 78.2 | 38 | 46.4 | 64.8 | 50 | 45 |
| Isopropanol | 90 | — | — | — | — | 38.5 | — | — | — | — |
| Propyl alcohol | — | — | — | — | — | — | — | — | — | — |
| 1-butyl alcohol | — | — | — | — | — | — | 46.4 | — | — | — |
| Polyol | | | | | | | | | | |
| Propylene glycol | — | — | — | 30 | 10 | 10 | — | 30 | 35 | — |
| Dipropylene glycol | 8.5 | — | — | — | 10 | — | 5 | — | — | 29.6 |
| Glycerol | — | 10 | — | — | — | 10 | — | — | — | — |

TABLE 7-continued

EXEMPLARY COMPOSITIONS

Other components

| | | | | | | | | | | |
|---|---|---|---|---|---|---|---|---|---|---|
| Sodium meta-bisulfate | 0.1 | 0.2 | 0.2 | 0.2 | 0.2 | 0.2 | — | 0.2 | — | 0.2 |
| Hydroxypropyl cellulose HF (HPC HF) | 0.8 | — | 0.6 | 0.6 | 0.6 | 0.6 | 0.6 | — | — | 0.2 |
| Hydroxypropyl methyl cellulose (HPMC) | — | 0.3 | — | — | — | — | — | — | — | — |
| Cineole | — | — | — | — | — | 1 | 1 | — | — | 5 |

Example 12

Minocycline Uptake in Ex Vivo Human Facial Tissue—a Quantitative and Qualitative Comparison Study A skin penetration study was conducted to determine and compare the uptake of minocycline by ex-vivo human facial skin tissue in a hydrophilic liquid formulation containing 1% or 4% minocycline (BPX-1M and BPX-4M, respectively) with a lipophilic-based formulation as described in U.S. Patent Publication No. 2015/0056149. The delivery of minocycline was measured using HPLC to quantitatively measure the amount of minocycline into the skin in relation to time, and by fluorescence microscopy to visually determine the presence of minocycline in the pilosebaceous gland and epidermis.

The following topical formulations were evaluated.

TABLE 8

BPX-1M AND BPX-4M FORMULATIONS

| | PERCENT IN FORMULATION | | |
|---|---|---|---|
| MATERIAL | BPX-1M 1% MINO-CYCLINE | BPX-4M 4% MINO-CYCLINE | BPX PLACEBO |
| Minocycline HCl | 1.2% | 4.6% | — |
| Hydroxypropyl cellulose (KLUCEL HF) | 0.6% | 0.6% | 0.6% |
| Magnesium Chloride, anhydrous | 1.2% | 4.6% | 0.6% |
| Ethanol, anhydrous | 75.8% | 59.0% | 77.59% |
| Propylene Glycol | 20.0% | 30.0% | 20.0% |
| Eucalyptol | 1.0% | 1.0% | 1.0% |
| Sodium Metabisulfite | 0.2% | 0.2% | 0.2% |
| Quinoline Yellow | — | — | 0.01% |

TABLE 9

Lipophilic Formulation

| | PERCENT IN FORMULATION | | |
|---|---|---|---|
| MATERIAL | 1% LIPO-PHILIC | 4% LIPO-PHILIC | LIPOPHILIC PLACEBO |
| Minocycline HCl | 1.20 | 4.80 | — |
| Soybean oil | 50.00 | 50.00 | 50.00 |
| Coconut oil | 23.60 | 23.60 | 23.60 |
| Light Mineral oil | 4.35 | 0.75 | 5.55 |
| Cyclomethicone | 5.00 | 5.00 | 5.00 |
| Cetostearyl alcohol | 3.50 | 3.50 | 3.50 |
| Stearic acid | 3.00 | 3.00 | 3.00 |
| Myristyl alcohol | 2.50 | 2.50 | 2.50 |
| Hydrogenated castor | 2.00 | 2.00 | 2.00 |
| Beeswax | 2.00 | 2.00 | 2.00 |
| Stearyl alcohol | 1.50 | 1.50 | 1.50 |
| Behenyl alcohol | 1.10 | 1.10 | 1.10 |
| Silicon dioxide | 0.25 | 0.25 | 0.25 |

The lipophilic formulation is described in U.S. Patent Application Publication No. 20150056149, Composition 244B Example 4 Part A.

Human facial skin (female, 60 s) was removed from a −20° C. freezer and thawed at 32° C. The hypodermis and fatty layer were removed. Skin pieces were cut to ~0.7 cm$^2$ and placed on a gauze pad-lined petri dish (hydrated with 0.9% sodium chloride with 0.2% sodium azide). The skin surface was blotted dry. The hydrophilic BPX formulations that had been stored at −4° C. were brought to room temperature. Lipophilic formulations were solid at room temperature and therefore were warmed (32° C., ~3 min) to a fluid liquid state immediately before application. A dose of 2.5 mg/cm$^2$ was used. Using a pipette, each formulation was applied evenly over the target area of 0.42 cm$^2$. Spreading was evenly carried out until dry (~7 seconds). The tissue in the petri dish was placed uncovered in a 32° C. incubator, with the gauze pad staying moderately hydrated. Formulations were applied for 2 and 4 hours.

TABLE 10

Application Amounts

| Formulation | Target Minocycline Amount (mg/0.42 cm$^2$) | Formulation Amount (mg/0.42 cm$^2$) | Formulation Volume (μl/0.42 cm$^2$) | Formulation Amount for Histology (mg) | Formulation Volume for Histology (μl/0.42 cm$^2$) |
|---|---|---|---|---|---|
| Untreated | — | — | — | — | — |
| Lipophilic Placebo | — | 1.05 | 1.17 | 25 | 27.4 |
| BPX Placebo | — | 1.05 | 2.6 | | 39 |
| BPX-1M | 0.0105 | 1.05 | 2.10 | 25 | 37 |

TABLE 10-continued

Application Amounts

| Formulation | Target Minocycline Amount (mg/0.42 cm²) | Formulation Amount (mg/0.42 cm²) | Formulation Volume (μl/0.42 cm²) | Formulation Amount for Histology (mg) | Formulation Volume for Histology (μl/0.42 cm²) |
|---|---|---|---|---|---|
| 1% Lipophilic | | 1.05 | 1.10 | 25 | 26.6 |
| BPX-4M | 0.0441 | 1.05 | 2.08 | 25 | 34.8 |
| 4% Lipophilic | | 1.05 | 1.138 | 25 | 26 |

At the end of each time point, the formulation was removed with a 70% isopropanol alcohol-soaked gauze pad then blotted dry with a dry gauze pad. A biopsy punch (6 mm) was taken from each test site. (The full thickness of the skin was used for each biopsy.) Minocycline was then extracted from each biopsy with 500 μl of acidified methanol (10 μl of 5N HCl to 1 ml MeOH) for 24 hours at 25° C. The supernatant was analyzed by HPLC (20 μl injection, 15 minute run, 350 nm). The intact minocycline as well as an epi-minocycline (4-epi) peak area were measured in each sample. Donor data was averaged amongst the given treatment group. HPLC standards were run (0.01, 0.1, and 1 mg/ml) for minocycline-HCl and acidified methanol; with minocycline-base standards calculated.

Histology: Tissue was prepared in the same manner as described above. An amount corresponding to 50 mg/cm² was applied uniformly with a pipette (Table 3). Tissue in the petri dish was placed in a 32° C. incubator with a parafilmed cover for 24 hours. At 24 hours, excess formulation was gently wiped off and areas of skin where formulation was not applied were cut off. The remaining tissue was then embedded in O.C.T. Tissue block sections were cut (~12 μm). Two sections were cut serially with ~100 μm distance between each serially-cut set. Slides were washed with 1×PBS then cover-slipped with glycerol to obtain fluorescent images.

For the hydrophilic BPX-1M formulation, 5.9 μg/cm² and 5.3 μg/cm² of minocycline was detected at 2 and 4 hours, respectively (see FIG. 9a). For the lipophilic 1% formulation, 2.4 μg/cm² and 2.1 μg/cm² of minocycline was detected at 2 and 4 hours, respectively (FIG. 9a). Minocycline was not detected in the lipophilic placebo, BPX placebo and un-treated skin samples. The hydrophilic BPX-1M formulation yielded significantly greater minocycline amounts in comparison to the lipophilic formulation.

Figure 10:
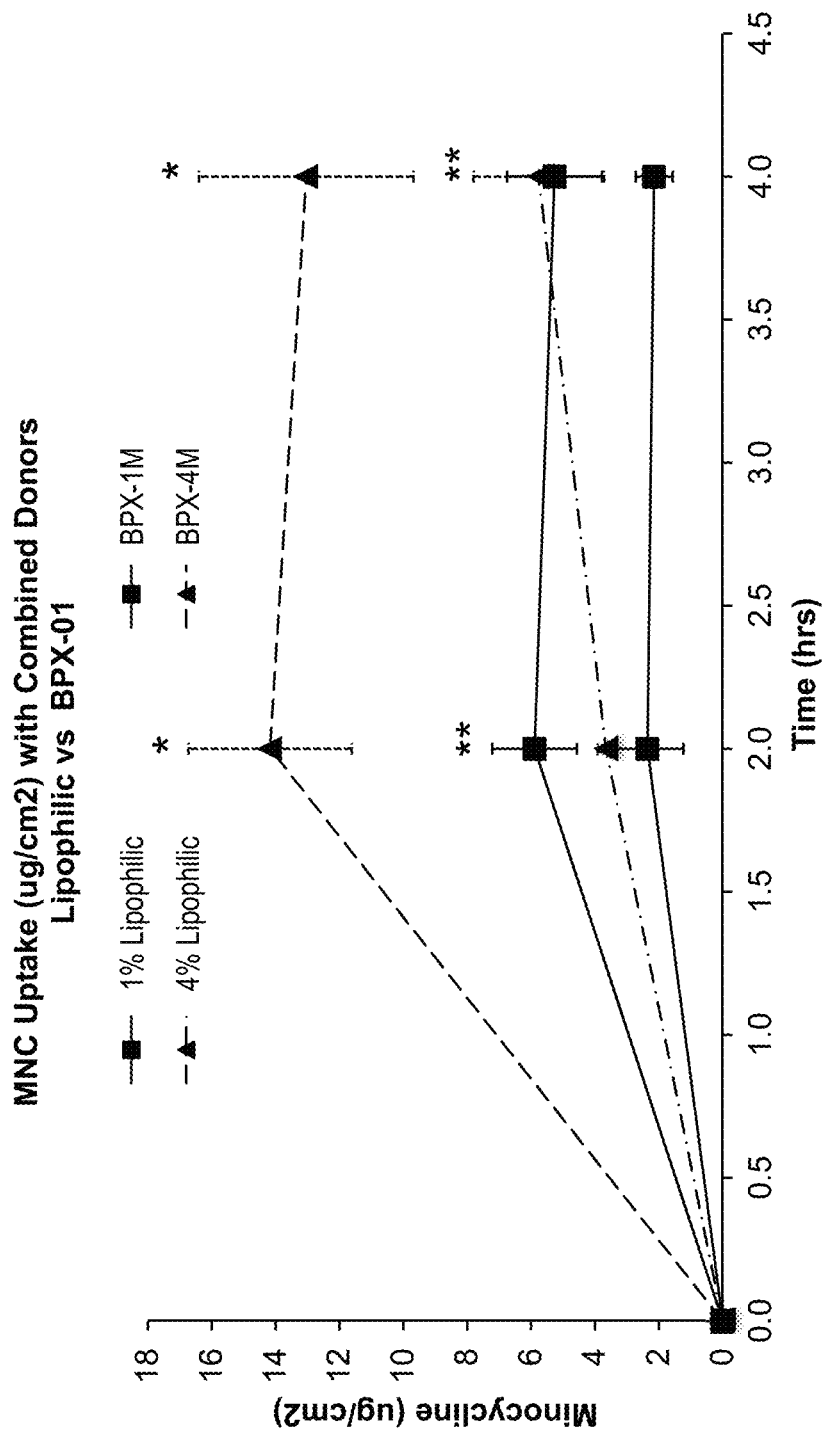
FIG. 10 is a plot illustrating the concentration of minocycline ($\mu g/cm^2$) in facial skin over time in an ex vivo study as described in Example 12 for topical formulations containing 1% and 4% minocycline.

The hydrophilic BPX-4M formulation demonstrated 14.2 μg/cm² and 13.0 μg/cm² of minocycline at 2 and 4 hours, respectively (FIG. 9b). For the lipophilic 4% formulation, 3.7 μg/cm² and 5.8 μg/cm² of minocycline was detected at 2 and 4 hours, respectively (FIG. 9b). No minocycline was detected in untreated skin tissue. Similarly, no minocycline was detected in the skin tissue treated with lipophilic placebo or with BPX-01 placebo. The hydrophilic BPX-4M formulation yielded a significantly greater amount of minocycline in comparison to the lipophilic formulation. A similar uptake was seen with the hydrophilic BPX-1M and lipophilic 4% formulations (FIG. 10) at both time-points tested despite the lipophilic formulation having 4 times higher concentration of the minocycline drug.

Figure 11A:
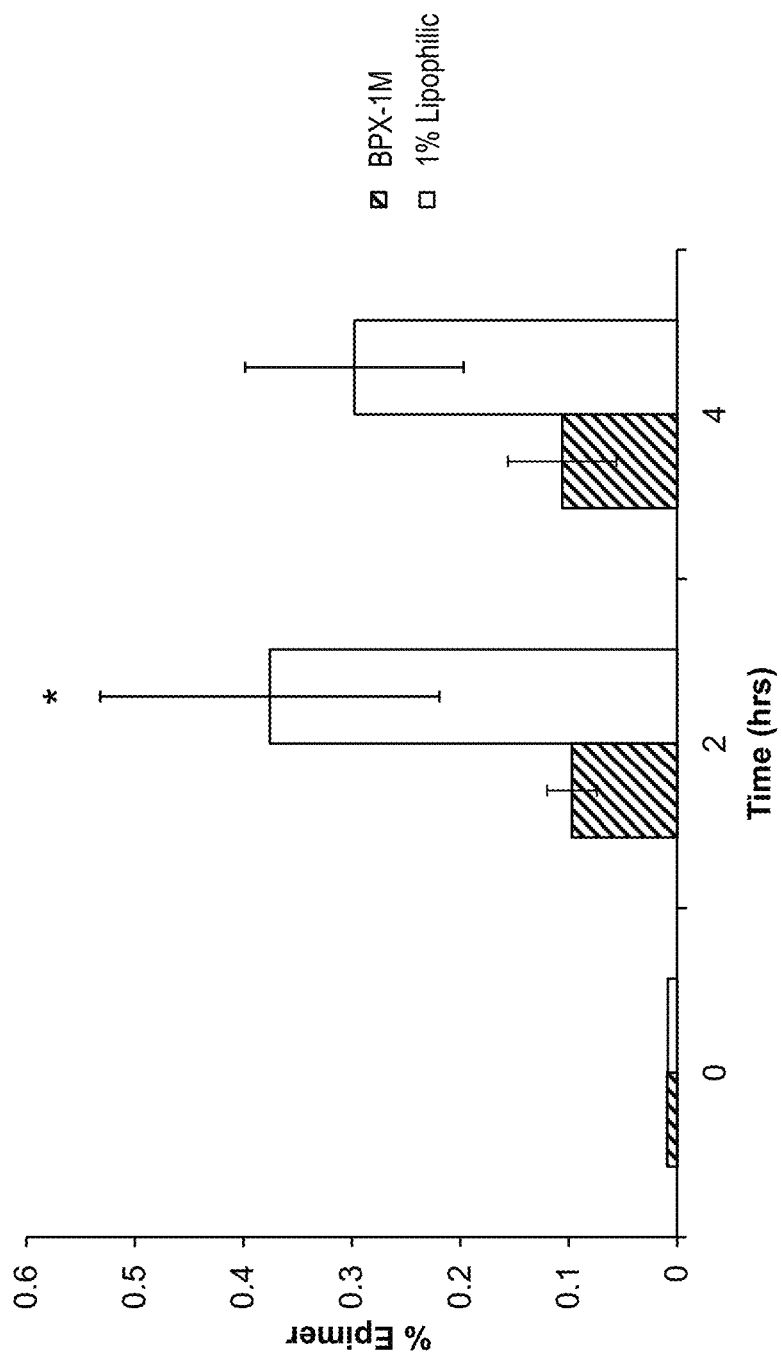
FIGS. 11A and 11B illustrate the epimerization of minocycline resulting from ex vivo topical application of formulations containing 1% and 4% minocycline, respectively, as described in Example 12.

Prior to application, minocycline epimer concentration was measured in the 1% formulations with values of 0.93% and 0.86% for the BPX-1M formulation and lipophilic formulation, respectively (FIG. 11a). From treated skin samples, minocycline epimerization was measured at 9.7% and 10.6% for the hydrophilic BPX-1M formulation at 2 and 4 hours, respectively. Increased epimerization values of 37.6% and 29.8% were determined for the lipophilic 1% formulation measured at 2 and 4 hours, respectively (FIG. 11a).

Figure 11B:
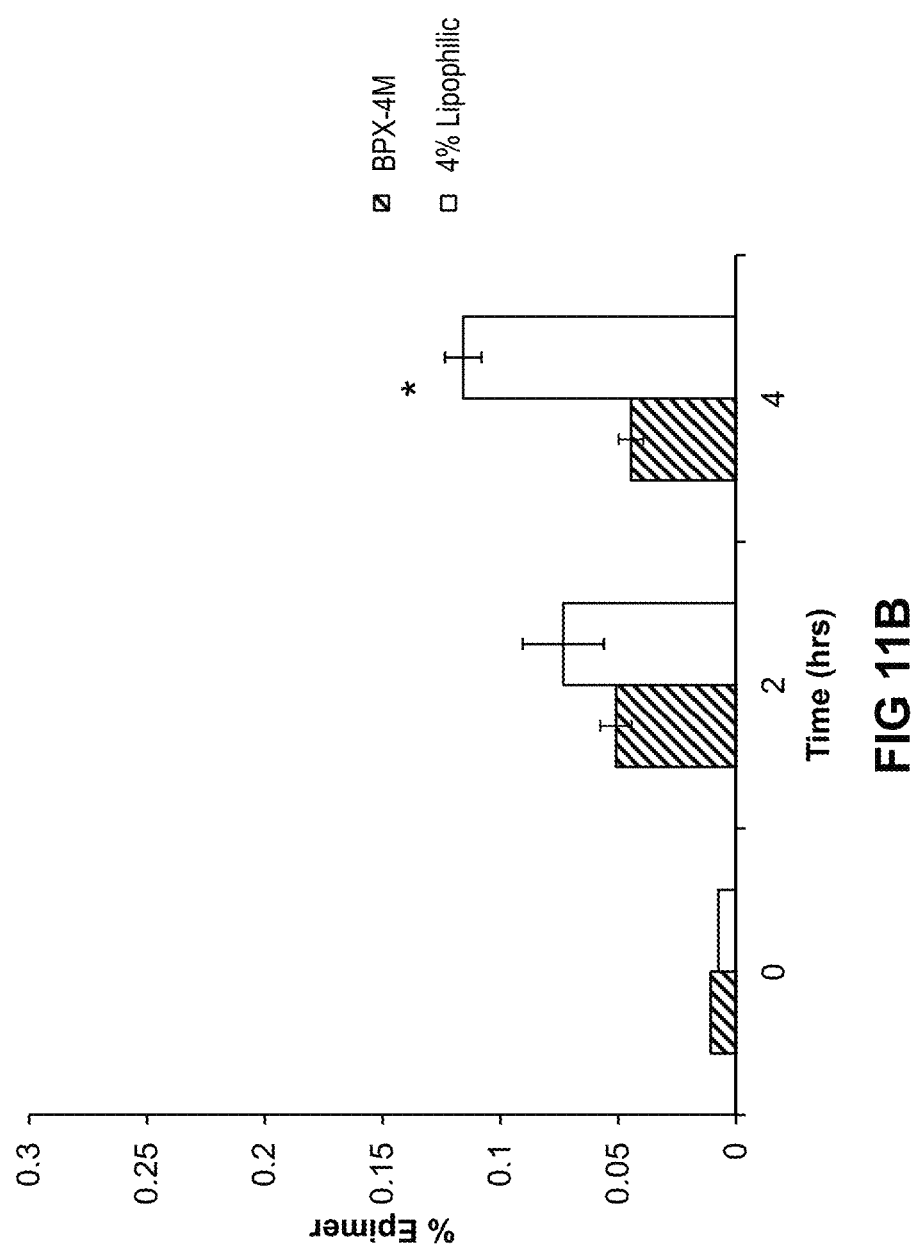

Prior to application, minocycline epimer concentration was measured in the 4% formulations with values of 1.08% and 0.75% for the BPX-1M and lipophilic formulation, respectively (FIG. 11b). From skin samples treated with the hydrophilic BPX-4M formulation, minocycline epimerization was measured at 5.1% and 4.5% at 2 and 4 hours, respectively. Increased epimerization values of 7.3% and 11.6% were determined for the lipophilic 4% formulation measured at 2 and 4 hours, respectively (FIG. 11b).

The hydrophilic formulations penetrated better into ex vivo human skin than the lipophilic formulation, and the minocycline that did penetrate into the skin did not degrade as significantly in the hydrophilic formulations as it did in the lipophilic formulation.

Figure 12A:
FIGS. 12A-E are fluorescence micrographs of facial skin to which topical formulations containing 4% minocycline were applied ex vivo as described in Example 12.
Figure 12B:
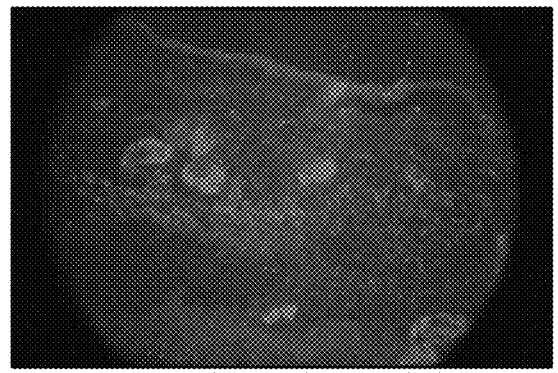
Figure 12C:
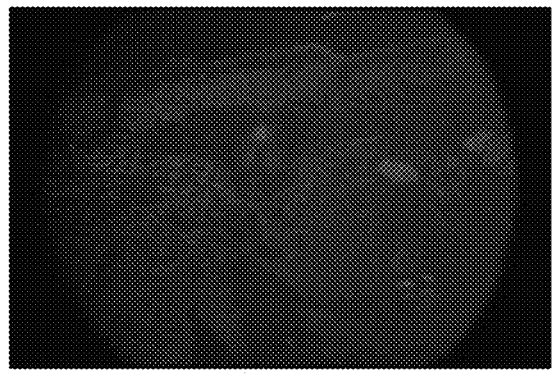
Figure 12D:
Figure 12E:

A notable increase in fluorescence intensity is observed in the stratum corneum, epidermis and in the sebaceous glands for the hydrophilic BPX-4M formulation (FIG. 12D) in comparison to the 4% lipophilic formulation (FIG. 12A). The data show penetration of minocycline into sebaceous glands where P. acnes bacteria are located. For comparison, fluorescence intensity is also shown for the lipophilic placebo (FIG. 12B), no treatment (FIG. 12C), and the BPX placebo (FIG. 12E).

Example 13

In Vivo Minipig 7- and 20-Day Repeat Dose Patch Study

A minipig topical application study was conducted over a period of either 7 days or 20 days, respectively, to evaluate the skin and plasma uptake and dermal toxicity associated with repeat dose applications of formulations of minocycline containing different amounts of minocycline equivalent base (placebo, 0.5%, 1%, 2%, and 4%). The study was performed using 4 non naïve, antibiotic free female minipigs, weighing between 20 and 30 kg and of 12-18 months age. The test articles applied were the same as described in Example 8, Table 5 (i.e., compositions 0-B, 0.5-B, 1-B, 2-B, and 4-B).

On Day 0, the animals were weighed and anesthetized. The right and left flank area were carefully clipped and shaved, and six test application sites, of 3 cm×3 cm each or approximately about 10 cm² were marked. Test and control articles were applied topically using a positive displacement pipette and spreading in the marked test area using metal spatula. Dosing continued daily until Day 6 (Group 1) and Day 20 (Group 2). Prior to daily dosing, treatment sites were gently wiped once with soap followed by a gentle wash with phosphate buffer saline (PBS). Body weights were measured once weekly.

TABLE 11

SUMMARY OF DOSING SITES TREATMENT

| Dosing Site | Animals 151/251 | | | Animals 152/252 | | |
|---|---|---|---|---|---|---|
| | Test Article | Dose/ Formulation | Volume (µL) | Test Article | Dose/ Formulation | Volume (µL) |
| L1 | 0-B | Vehicle, 0% Minocycline | 25 | 0-B | Vehicle, 0% Minocycline | 125 |
| L2 | 0.5-B | 0.5% | 25 | 0.5-B | 0.5% | 125 |
| L3 | 1-B | 1% | 25 | 1-B | 1% | 125 |
| L4 | 2-B | 2% | 25 | 2-B | 2% | 125 |
| L5 | 4-B | 4% | 25 | 4-B | 4% | 125 |

Dosing sites was evaluated daily for erythema and edema using a modified Draize scoring system. Photographs were taken prior to dose administration on Day 0 and daily thereafter. Skin pigmentation was visually noted daily. Additionally, UV lamp photos of the dosing sites were taken on Day 0 and at the end of the dosing (Day 7 for Group 1 and Day 20 for Group 2). At the end of the study, animals were sacrificed and skin tissues were collected from the dosing sites, along with one untreated site.

Results: No abnormal weight changes were observed in any treatment group. No skin irritation was noted throughout the treatment period as indicated by a lack of erythema and edema. The total amount of formulation applied over the course of the 7 or 20 day treatment was 54.3 mg (#151), 91.9 mg (#152), 155 mg (#251), and 262.5 mg (#252). The lower detection limit of the plasma extraction protocol was 1.0 ng/ml. In these analyses, no minocycline was detected in any of the plasma samples analyzed.

Transient and differential yellowing of the patch was observed with the 1.0% formulations at 125 mg of application amount starting at Day 4 and was sustained throughout the duration of the experiment (FIG. 1). 125 mg of formulation is equivalent to 12.5 mg/cm$^2$ of treatment, which is equivalent to about a 5 g daily application in humans (assuming 400 cm$^2$ area in a human face). Yellowing was seen the 2% and 4% groups with staining observed as early as the second day of treatment.

In all application sites, at least 1 µg/cm$^2$ of minocycline was detected, with at least 2-3 times that amount of minocycline found in the 1%, 2% and 4% formulation groups. The increase of minocycline uptake was not linear. In the 20-day treatment group, a degree of saturation was observed at the 25 mg application level. The 7-day and 20-day groups showed similar trends in minocycline uptake in skin, suggested that the treatment regimen may be approaching saturation.

In the image analysis (now shown), minocycline was localized within the pilosebacous glands in 0.5%, 1%, 2%, and 4% formulation groups. Minocycline was detected in the stratum corneum and the hair follicles. An increased amount of minocycline was detected in the 4% groups. No differences were observed between the 7 day and 20 day treatment groups. In this study, even at the 0.5% 25 mg application group, at least 1.03 µg/cm$^2$ of minocycline uptake was observed, which appears to meet the penetration requirement to achieve a local concentration within the skin that is indicative of a therapeutic dose. At ~1.03 µg/cm$^2$, this translates into 0.18 µg/g of minocycline in skin, which is at least an order of magnitude above the MIC necessary to inhibit *P. acnes*.

Example 14

In Vivo Rat Single Dose Study Skin Irritation, Pharmacokinetics Dose Ranging, and Histology A skin irritation study was conducted in rats topically administered compositions comprising minocycline and a magnesium salt in a solvent system comprising ethanol and propylene glycol (e.g., from 50-99.9 w/w %); pharmacokinetic parameters were also evaluated. The water content for each of the compositions applied, as measured by Karl Fischer titration, was in the range of 0.5% to 1%. The pH value for each of the compositions was in the range of 3.9 to 4.4. Single dose pharmacokinetic parameters were evaluated and demonstrated that the systemic exposure to the topically-applied minocycline compositions was lower than that of oral dosage forms effective to provide similar concentrations of drug in the skin.

Blood plasma levels of minocycline hydrochloride were assessed following a single treatment with four formulations containing approximately 0.5%, 1%, 2%, or 4% by weight minocycline as described in Table 12 below.

TABLE 12

TOPICAL FORMULATIONS OF MINOCYCLINE USED IN STUDY (ALL PERCENTAGES ARE LISTED BY WEIGHT (I.E. (W/W))

| | COMPOSITION NUMBER | | | | |
|---|---|---|---|---|---|
| | 0-B-2 | 0.5-B | 1-B | 2-B-2 | 4-B |
| Minocycline hydrochloride | 0% | 0.6% | 1.2% | 2.3% | 4.6% |
| Hydroxypropyl cellulose | 0.6% | 0.6% | 0.6% | 0.6% | 0.6% |
| Magnesium chloride (anhydrous) | 0.6% | 0.6% | 1.2% | 2.3% | 4.6% |
| Ethanol (anhydrous) | 77.59% | 77.0% | 75.8% | 73.6% | 59.0% |
| Propylene Glycol | 20.0% | 20.0% | 20.0% | 20.0% | 30.0% |
| 1,8-Cineole | 1.0% | 1.0% | 1.0% | 1.0% | 1.0% |
| Sodium meta-bisulfate | 0.2% | 0.2% | 0.2% | 0.2% | 0.2% |
| D&C Yellow #10 | 0.01% | 0.00% | 0.00% | 0.00% | 0.00% |
| Measured pH for composition | 4.86 | 4.35 | 4.19 | 3.90 | 3.90 |
| Measured water content for composition | 0.39% | 0.48% | 0.52% | 0.63% | 0.86% |

The day before treatment, a 15 cm$^2$ area was shaved on the dorsal area in the region of the shoulders and back of each of twenty one male Sprague-Dawley rats and a 10 cm$^2$ area was marked as the application test site. The rats were randomly divided evenly into 7 treatment groups. Each group received application of one of the compositions listed in Table 12 (0-B-2, 0.5-B, 1-B, 2-B-2, or 4-B) in the amount described in Table 13. The composition was applied to each of the rats in each treatment group. The compositions were applied uniformly to the application test site on each rat at time T=0.

TABLE 13

TREATMENT GROUPS

| Treatment Group | Composition Number Applied | Amount of Composition Applied Per Animal |
|---|---|---|
| Group 1 | 0-B-2 | 2.5 mg/cm$^2$ |
| Group 2 | 0.5-B | 2.5 mg/cm$^2$ |
| Group 3 | 1-B | 2.5 mg/cm$^2$ |

TABLE 13-continued

TREATMENT GROUPS

| Treatment Group | Composition Number Applied | Amount of Composition Applied Per Animal |
| --- | --- | --- |
| Group 4 | 2-B-2 | 2.5 mg/cm² |
| Group 5 | 4-B | 2.5 mg/cm² |
| Group 6 | 4-B | 5.0 mg/cm² |
| Group 7 | no composition applied | NA |

Blood draws were collected just prior to application and over the next 24 hour period at the following time points: 10, 20, and 30 minutes, 1, 2, 4, 6, 8, 12, and 24 hours after application. For each treatment group, the average level of minocycline in the plasma is presented in Table 14. The lower limit of quantification (LLOQ) for the analysis method was 10 ng/mL. Values of less than the LLOQ are reported as zero. The maximum serum concentration ($C_{max}$) in Sprague Dawley rats was less than 550 ng/mL for all compositions tested when measured at the above mentioned time points in an experiment in which the applied composition was allowed to penetrate unassisted for a 24-hour period in a shaved application test site of 10 cm² area with the composition uniformly applied in an amount of 2.5 or 5.0 mg/cm².

In all but one of these compositions, $C_{max}$ was less than 150 ng/mL. These levels of $C_{max}$ compare favorably to dosages for orally consumed minocycline that are effective to achieve the same levels of drug in the skin since such doses are delivered to the skin systemically and thus require higher levels in the blood.

TABLE 14

MINOCYCLINE LEVELS (NG/ML) IN PLASMA AS A FUNCTION OF ELAPSED TIME AFTER APPLICATION OF TESTED COMPOSITION.

| Treatment Group | 0 minute | 10 minute | 20 minute | 30 minute | 1 hour | 2 hour | 4 hour | 6 hour | 8 hour | 12 hour | 24 hour |
| --- | --- | --- | --- | --- | --- | --- | --- | --- | --- | --- | --- |
| Group 1 | 0 | 0 | 0 | 0 | 0 | 0 | 0 | 0 | 0 | 0 | 0 |
| Group 2 | 0 | 0 | 0 | 0 | 0 | 0 | 0 | 0 | 0 | 0 | 0 |
| Group 3 | 0 | 0 | 0 | 0 | 0 | 0 | 0 | 0 | 0 | 0 | 0 |
| Group 4 | 0 | 0 | 12 | 29 | 39 | 36 | 21 | 20 | 16 | 14 | 0 |
| Group 5 | 0 | 0 | 0 | 0 | 124 | 149 | 134 | 61 | 29 | 12 | 0 |
| Group 6 | 0 | 33 | 129 | 279 | 533 | 434 | 270 | 125 | 62 | 31 | 12 |
| Group 7 | 0 | 0 | 0 | 0 | 0 | 0 | 0 | 0 | 0 | 0 | 0 |

Irritation was evaluated using the modified Draize scoring system. Evaluations were performed prior to and immediately after application and at the following time points: 30 minutes, 1, 3, 6, and 24 hours after application. No measurable erythema, redness, irritation, and/or edema were observed. The modified Draize score was 0 for each of the time points and each of the rats in the study. This indicates that each of the compositions tested was non-irritating.

No abnormal weight changes were observed in any treatment group.

The rats were euthanized shortly after the 24-hour time point. Biopsies were taken from the skin of the rats and frozen or fixed in 10% formalin to allow further histological analysis, including staining with hematoxylin and eosin. No significant changes were observed in any of the skin sections when the groups treated with minocycline were compared to those treated with composition 0-B-2 or those not treated with any composition.

Example 15

In Vivo Rat Multiple Dose Study Skin Irritation and Pharmacokinetics Dose Ranging A multiple-dose toxicokinetic study was performed in Sprague-Dawley rats topically administered compositions comprising minocycline and a magnesium salt in a solvent system comprising ethanol and propylene glycol (e.g., from 50-99.9 w/w %). The potential toxicity of exemplary compositions were evaluated. Multiple-dose pharmacokinetic parameters were evaluated and demonstrated that the systemic exposure to the topically-applied minocycline compositions was lower than that of oral dosage forms effective to provide similar concentrations of drug in the skin. The amount of minocycline applied daily to each animal in the study was in the range of 0.0 to 0.5 mg/cm². The concentration of minocycline was approximately 0%, 1%, and 4% in compositions 0-B-2, 1-B-2, or 4-B-2 as described in Table 15.

TABLE 15

TOPICAL FORMULATIONS OF MINOCYCLINE USED IN STUDY (ALL PERCENTAGES ARE LISTED BY WEIGHT (I.E. (W/W))

| COMPOSITION NUMBER | 0-B-2 | 1-B-2 | 4-B-2 |
| --- | --- | --- | --- |
| Minocycline hydrochloride | 0% | 1.1% | 4.3% |
| Hydroxypropyl cellulose | 0.6% | 0.6% | 0.6% |
| Magnesium chloride (anhydrous) | 0.6% | 1.1% | 4.3% |
| Ethanol (anhydrous) | 77.59% | 75.9% | 69.6% |
| Propylene Glycol | 20.0% | 20.0% | 20.0% |
| 1,8-Cineole | 1.0% | 1.0% | 1.0% |
| Sodium meta-bisulfate | 0.2% | 0.2% | 0.2% |
| D&C Yellow #10 | 0.01% | 0.00% | 0.00% |

Twenty healthy male rats and twenty healthy female rats were divided evenly into four groups of five male and five female rats each. The rats were approximately 8 weeks of age at the start of the study and had body weights ranging from 280 to 330 grams. Compositions were applied daily to each rat in the study for 28 days based on the group number for each rat as described in Table 16. Rats were not moved among the groups during the study.

The animals were housed individually. Water and a standard diet of Lab Diet Rodent Feed No. 5001 were available to each rat ad libitum, except as required for procedures.

One day before the first application, a 15 cm$^2$ area was shaved on the dorsal region of the shoulders and back using standard animal clippers. The skin surface was gently wiped with acetone to remove sebum and to ensure the skin was clean. A 10 cm$^2$ area was marked using a non-toxic permanent ink marker. Cannulas were filled with approximately 150 µl of 1% heparin saline solution.

Prior to daily dosing, sites were cleaned with waterless shampoo (Sullivan E-Z Clean) and PBS. On Days 1-27, the appropriate test composition was applied using a positive displacement pipette and carefully spread in the marked test area of 10 cm$^2$ using a clean metal spatula. The applied composition was then allowed to dry and each rat was returned to its cage.

Blood plasma levels of minocycline hydrochloride were assessed after application during the first day of application (which was labeled as Day 1), the fourteenth day of application (which was labeled as Day 14), and the twenty-eighth day of application (which was labeled as Day 28). For each of the nights prior to sampling of plasma, the rats were fasted overnight, with free access to water.

TABLE 16

GROUPS

| Group | Number of Animals | Composition Number Applied Daily | Amount of Composition Applied Per Animal (mg/cm$^2$/day) | Minocycline Dose Per Animal (mg/cm$^2$/day) |
|---|---|---|---|---|
| 1 | 5 Males and 5 Females | 0-B-2 | 2.5 | 0 |
| 2 | 5 Males and 5 Females | 1-B-2 | 2.5 | 0.025 |
| 3 | 5 Males and 5 Females | 4-B-2 | 6.25 | 0.25 |
| 4 | 5 Males and 5 Females | 4-B-2 | 12.5 | 0.5 |

Significant dermal irritation was not observed in Groups 1 and 2 and included slight erythema Groups 3 and 4, with a greater incidence and severity of irritation occurring in Group 4.

There were no test article-related effects on body weight or changes, food consumption, clinical pathology parameters, gross pathology findings or organ weights. In addition, no differences in hematology or clinical chemistry were seen for any of the Groups other than the levels of minocycline measured in the plasma.

Minimal to mild acanthosis in application skin areas was observed and noted. These lesions were considered patchy in distribution with a slight increase in epidermal cellularity and occasional basal mitotic figures mostly observed in Group 4. Based on these results, the no-observed-adverse-effect level (NOAEL) was considered to be, in both males and females, about 0.25 mg/cm$^2$/day, which corresponded to 6.25 mg/cm$^2$/day of a composition comprising about 4% of minocycline.

The toxicokinetic characteristics of the compositions were measured in the plasma of each of the animals after daily administration of the compositions. For each of the Groups, minocycline was detected for each of the days on which an assessment was performed (i.e., Days 1, 14, and 28). A dose-dependent increase of minocycline was measured in the plasma as described in more detail by the data in Table 17. Minocycline was not detected at significant levels in the rats in Group 1. Gender differences in exposure was present in this study and was attributed to differences in hair density.

TABLE 17

SUMMARY OF TOXICOKINETIC PARAMETERS IN RAT PLASMA

| Group | Sampling Day | Cmax (ng/mL) Male | Cmax (ng/mL) Female | AUC (ng * hr/mL) Male | AUC (ng * hr/mL) Female | Tmax (hr) Male | Tmax (hr) Female |
|---|---|---|---|---|---|---|---|
| 2 | 1 | 54 | 98.1 | 347.6 | 961.3 | 1 | 2 |
|   | 14 | 28.7 | 294.4 | 406.4 | 2833.5 | 1 | 2 |
|   | 28 | 39.1 | 33.1 | 14.0 | 21.8 | 4 | 4 |
| 3 | 1 | 3914.8 | 11308.1 | 17070.5 | 75525.9 | 1 | 2 |
|   | 14 | 2199.3 | 10519.1 | 17395.5 | 77513.3 | 2 | 1 |
|   | 28 | 761.5 | 937.7 | 281.6 | 175.7 | 4 | 4 |
| 4 | 1 | 2392.8 | 3149.1 | 30076 | 30899.9 | 2 | 2 |
|   | 14 | 6936.7 | 12553.3 | 72168.8 | 142035.5 | 4 | 2 |
|   | 28 | 8618.5 | 9082.3 | 923.7 | 550.4 | 4 | 4 |

This study, as described in Example 15, demonstrated that repeat dosing of a mammal can be performed safely at dosage levels of minocycline in the range of 0.0 mg/cm$^2$/day to 0.5 mg/cm$^2$/day, or preferably in the range of about 0.025 mg/cm$^2$/day to about 0.5 mg/cm$^2$/day, or more preferably in the range of about 0.025 mg/cm$^2$/day to about 0.25 mg/cm$^2$/day. Higher doses of minocycline allow more aggressive treatments. Dosages above 0.25 mg/cm$^2$/day are preferred. To avoid the level of irritation identified in Group 4, dosages less than 0.5 mg/cm$^2$/day are preferred.

Example 16

In Vivo Minipig Multiple Dose Toxicokinetic Study

A multiple-dose toxicokinetic study was performed in Göttingen minipigs with topically administered compositions comprising minocycline and a magnesium salt in a solvent system comprising ethanol and propylene glycol (e.g., from 50-99.9 w/w %). The potential toxicity of exemplary compositions were evaluated. Toxicokinetic parameters were evaluated. The amount of each formulation applied daily to each animal in the study was in the range of 0.0 to 12.5 mg/cm$^2$. The concentration of minocycline was approximately 0%, 1%, and 4% in compositions 0-B-2, 1-B-2, and 4-B-2 as described in Table 15 of Example 15.

Fifteen healthy male Göttingen minipigs and fifteen healthy female Göttingen minipigs were randomly divided into five groups of three male and three female minipigs each. The minipigs were approximately 20 weeks of age at the start of the study and had body weights ranging from 7.4 to 10.3 kilograms. Compositions were applied daily to each minipig in the study for 28 days based on the group number for each minipig as described in Table 18. Group 1 was a sham (i.e., non-treated) control group. Minipigs in Group 1 went through the same procedures as minipigs in Groups 2-5, except that no test composition was applied to the marked treatment area.

The animals were housed individually. Each minipig had free access to water and was provided a twice daily ration of a standard diet.

One day before the first application and as needed thereafter, the dorsal region of each minipig was prepared by close clipping the hair with standard animal clippers. Care was taken during the clipping procedure to avoid abrasion of the skin. The skin surface was gently wiped with gauze soaked in waterless shampoo (SULLIVAN E-Z CLEAN, Sullivan Supply, Inc. Dunlap, Iowa), then with gauze soaked in warm (37-43° C.) reverse osmosis water, and then with dry gauze to ensure the skin was clean. The target surface area for application for each minipig was calculated once per week according to the following formula: target surface area in square meters=[9.5*(body weight in grams)$^{2/3}$]/10,000. The corresponding area was marked on each minipig with indelible ink. This target surface area corresponds to approximately 15% of the total body surface area (Spector, W.S. Handbook of Biological Data. Philadelphia: W.B. Saunders Co. 1956; 175).

Prior to daily dosing, sites were cleaned as described previously. On Days 1 to 28, the appropriate test composition was applied to minipigs in Groups 2 to 5 and carefully spread in the marked test area using a clean disposable plastic applicator. The applied composition was then allowed to dry and each minipig was returned to its cage.

Blood plasma levels of minocycline were assessed after application during the first day of application (which was labeled as Day 1), the fourteenth day of application (which was labeled as Day 14), and the day after the twenty-eighth day of application (which was labeled as Day 28). For each of the nights prior to sampling of plasma, the minipigs were fasted overnight, with free access to water.

Urinalysis was performed for each minipig on Day 14 and after necropsy. Urine was collected overnight via cage pan drainage on Day 14 and via cystocentesis at necropsy. Minipigs were fasted overnight for the night prior to their scheduled necropsy.

TABLE 18

GROUPS

| Group | Number of Animals | Composition Number Applied Daily | Amount of Composition Applied Per Animal (mg/cm$^2$/day) | Minocycline Dose Per Animal (mg/cm$^2$/day) |
|---|---|---|---|---|
| 1 | 3 Males and 3 Females | No test composition (Sham control group) | 0 | 0 |
| 2 | 3 Males and 3 Females | 0-B-2 | 2.5 | 0 |
| 3 | 3 Males and 3 Females | 1-B-2 | 2.5 | 0.025 |
| 4 | 3 Males and 3 Females | 4-B-2 | 6.25 | 0.25 |
| 5 | 3 Males and 3 Females | 4-B-2 | 12.5 | 0.5 |

The following parameters and endpoints were evaluated in the study: clinical changes, dermal scores, body weights, food consumption, ophthalmological changes, electrocardiographic rhythms, clinical pathology parameters (including parameters from hematology, coagulation, clinical chemistry, urinalysis), toxicokinetic parameters, gross pathology findings, organ weights, and histopathologic features.

No adverse clinical signs were observed in Groups 1 to 4. In Group 5, some minipigs demonstrated increased activity, vocalization, excessive scratching, and tremors during the last two weeks of the study immediately after administration of the dose. Such symptoms resolved within 1 to 3 hours postdose.

No dermal irritation was observed in Groups 1 to 3. In Groups 4 and 5, some dermal irritation was observed. The average severity of dermal irritation was higher for Group 5 than for Group 4 and included two cases of ulceration and one case of fissuring.

There were no test article related effects on body weight, food consumption, opthalomological changes, electrocardiographic rhythms, clinical pathology parameters, gross pathology findings, organ weights, or histopathologic features.

No minipigs died prior to scheduled necropsy.

The toxicokinetic characteristics were measured in the plasma of each of the minipigs after daily topical administration of the compositions. A dose-dependent increase of minocycline was measured in the plasma as described in more detail by the data in Table 19. Minocycline was below the lower limit of quantitation of 1 ng/mL throughout the entire sampling period in Groups 1 to 3 and for Day 1 in Group 4.

TABLE 19

SUMMARY OF MEAN TOXICOKINETIC PARAMETERS IN MINIPIG PLASMA BY GROUP

| | Sampling | Cmax (ng/mL) | | AUC (ng * hr/mL) | | Tmax (hr) | |
|---|---|---|---|---|---|---|---|
| Group | Day | Male | Female | Male | Female | Male | Female |
| 4 | 1 | NC | NC | NC | NC | NC | NC |
|   | 14 | 8.06 | 8.27 | 116 | 132 | 2 | 2 |
|   | 28 | 25.6 | 15.2 | 408 | 273 | 8 | 2 |
| 5 | 1 | 5.86 | 6.60 | 47.4 | 75.4 | 8 | 2 |
|   | 14 | 62.0 | 23.7 | 647 | 270 | 2 | 1 |
|   | 28 | 71.6 | 42.5 | 921 | 681 | 4 | 8 |

NC = not calculable because below level of quantitation

On Day 28, the treated areas were cleaned as described above and minipigs in the study were euthanized. Skin samples were extracted to measure the level of minocycline present in the skin.

TABLE 20

SUMMARY OF MEAN MINOCYCLINE LEVELS IN MINIPIG SKIN BY GROUP

| | Skin Minocycline Level (µg/mL) | |
|---|---|---|
| Group | Male | Female |
| 1 | NC | NC |
| 2 | NC | NC |
| 3 | 7.3 | 7.4 |
| 4 | 75.6 | 11.2 |
| 5 | 20.0 | 27.7 |

NC = not calculable because below level of quantitation

In summary, dermal administration of each of the compositions tested in this study was well tolerated in minipigs. Based on the results, the no-observed-adverse-effect level (NOAEL) was considered to be, in both males and females, about 0.25 mg/cm$^2$/day (corresponding to 0.269 mg/cm$^2$/day of minocycline-hydrochloride), which corresponded to 6.25 mg/cm$^2$/day of a composition comprising about 4% of minocycline and corresponded to a Cmax of 25.6 ng/mL in males and 15.2 ng/mL in females and an AUC of 408 hr*ng/mL in males and 273 hr*ng/mL in females after 28 day repeat application.

This study, as described in Example 16, demonstrated that repeat dosing of a mammal can be performed safely at dosage levels of minocycline in the range of 0.0 mg/cm$^2$/day to 0.5 mg/cm$^2$/day, or preferably in the range of about 0.025 mg/cm$^2$/day to about 0.5 mg/cm$^2$/day, or more preferably in the range of about 0.025 mg/cm$^2$/day to about 0.25 mg/cm$^2$/day. Higher doses of minocycline allow more aggressive treatments. Dosages of at least 0.01 mg/cm$^2$/day or dosages of at least 0.025 mg/cm$^2$/day are preferred. To avoid the level of irritation identified in Group 5, dosages less than 0.5 mg/cm$^2$/day are preferred.

Example 17

In Vitro Eye Irritation Test in Epiocular Eit Model

The eye irritation effects for two compositions comprising minocycline, a magnesium salt, and sodium metabisulfite in a solvent system comprising ethanol and propylene glycol were evaluated. These were compared to a vehicle composition without minocycline as well as positive and negative controls.

The United Nations publishes the "Globally Harmonized System of Classification and Labelling of Chemicals (GHS)" for classification of eye effects (Globally Harmonized System of Classification and Labelling of Chemicals (GHS); Chapter 3: Serious Eye Damage/Irritation—Second Revised Edition, United Nations; No. ST/SG/AC. 10/30, Rev 2, 2007). Tested chemicals and compositions are classified into one of 3 categories: no eye damage (i.e., GHS category "No Category"), irreversible eye damage (i.e., GHS category 1), or reversible eye irritation (i.e., GHS category 2).

In our study, the eye irritation effects were evaluated by following the procedure described in the MATTEK EPIOCULAR Eye Irritation Test (EIT) Protocol (EpiOcular™ Eye Irritation (OCL-200-EIT) for the Prediction of Acute Ocular Irritation of Chemicals, Reference No. MK-24-007-0055, MatTek Corporation, Ashland, Mass.). The MATTEK EPIOCULAR model is a commercially available 3-dimensional model of the human corneal epithelium derived from normal human epidermal keratinocytes. The endpoint of the test is an estimation of cell viability by MTT assay (methylthiazolyldiphenyltetrazolium bromide). Since the region of the eye that is most commonly damaged by a composition would be the outer surface of the cornea and this model emulates the outer portion of the cornea, this model is commonly used to evaluate the eye irritation potential for chemicals. The use of the EPIOCULAR EIT protocol is specified in OECD Test Guideline No. 492. This test thus provided an indication of the level of eye irritation or damage that would be observed in an in vivo test.

Compositions were classified as having no eye damage (i.e., GHS category "Not Classified") if the MTT cell viability was greater than 60% relative to control samples of ultrapure water. Ethyl acetate was used as a positive control. Cell viability was measured via optical density as measured by a MULTISKAN SPECTRUM plate reader (Thermo Fisher Scientific Oy, Vantaa, Finland). MTT cell viability for MATTEK EPIOCULAR models were tested following an exposure to a compositions (or a control) in a humidified incubator maintained at 37° C. in a 5% CO$_2$ atmosphere for 30 minutes. The cell viability scale was measured relative to the post-exposure cell viability for the negative control (ultrapure water). The mean cell viability for the negative control was used to set the value that corresponded to 100% cell viability. Compositions were classified as having eye irritation or damage (i.e., GHS category 1 or 2) if the post-exposure cell viability was less than or equal to 60% of the corresponding mean cell viability for the negative control sample. In this study, compositions 0-B-2, 1-B-2, and 4-B-2 as described in Table 15 of Example 15 were assessed.

The results of the study showed that the mean post-exposure MTT cell viability relative to the negative control was 48% for composition 0-B-2, 64% for composition 1-B-2, and 49% for composition 4-B-2. Thus, it was determined that compositions 0-B-2 and 4-B-2 were eye irritating or damaging (UN GHS category 1 or 2) and composition 1-B-2 caused no eye damage (i.e. UN GHS category "No Category").

Thus, some compositions according to the invention have a MTT cell viability after exposure to the composition relative to the initial value for MTT cell viability of greater than 60% when tested with the MATTEK EPIOCULAR model according to the MATTEK EPIOCULAR EIT Protocol.

Example 18

In Vivo Guinea Pig Dermal Sensitization Study

The dermal sensitization potential for compositions comprising minocycline, a magnesium salt, and sodium metabisulfite in a solvent system comprising ethanol and propylene glycol was evaluated. The study used Hartley-derived albino guinea pigs according to the Groups shown in Table 21.

TABLE 21

| GROUPS TESTED IN DERMAL SENSITIZATION STUDY | | | | |
|---|---|---|---|---|
| Group | Number of Animals | Induction Phase (weekly treatments for 3 weeks) | Challenge Phase | Re-challenge Phase |
| 1 (Vehicle control) | 5 Males and 5 Females | 0-B-2 | 0-B-2 | 0-B-2 |
| 2 (treatment group) | 10 Males and 10 Females | 4-B-2 | 4-B-2 | 4-B-2 |
| 3 (common challenge control) | 5 Males and 5 Females | None | 0-B-2 and 4-B-2 | None |
| 4 (common rechallenge control) | 5 Males and 5 Females | None | None | 0-B-2 and 4-B-2 |
| 5 (HCA Test) | 5 Males and 5 Females | 5.0% HCA in ethanol | 2.5% and 1.0% HCA in acetone | None |
| 6 (HCA Positive Control) | 5 Males and 5 Females | None | 2.5% and 1.0% HCA in acetone | None |

Ten (10) male and 10 female guinea pigs (Group 2) were topically treated with 4-B-2 (approximately 4% minocycline) once per week, for 3 consecutive weeks. Additionally, a control group of 5 male and 5 female guinea pigs (Group 1) was topically treated with Vehicle (0-B-2) once per week, for 3 consecutive weeks. Following an approximate 2-week rest period, a challenge was performed whereby the guinea pigs of Groups 1 and 2 were retreated with 4-B-2 or 0-B-2, respectively and a previously untreated (naïve) challenge group of control guinea pigs (Group 3) was treated with 4-B-2 and 0-B-2. For the previously untreated (naïve) challenge group of control guinea pigs, both compositions 4-B-2 and 0-B-2 were applied to two distinct locations on each test animal. Challenge responses in the test animals in Groups 1 and 2 were compared with those of the challenge control animals in Group 3.

Following an approximate 1-week rest period, a re-challenge was performed during which the animals in Groups 1, 2, and 4 were topically treated with the appropriate material as described in Table 21. Re-challenge responses in the test animals (Groups 1 and 2) were compared to those of the control animals of Group 4.

An α-Hexylcinnamaldehyde (HCA) positive control was included in this study. This positive control consisted of 10 guinea pigs in an HCA test group (Group 5) and 10 guinea pigs in an HCA control group (Group 6). The animals were treated as described in Table 21 with the HCA test animals receiving 5% w/v HCA in ethanol for induction and 2.5% and 1.0% w/v HCA in acetone for challenge. For the challenge, both 1.0% and 2.5% w/v HCA compositions were applied to two distinct locations on each test animal.

All animals exceeded their starting weight during the study, which was indicative of good health in the animals. Isolated findings of slight weight loss, between challenge and re-challenge dose administration, were noted in test and/or vehicle-tested animals; these decreases were minimal and therefore were not considered to be related to the application of the 4-B-2 or 0-B-2 composition. Irritation was noted with several animals during the challenge administration. This irritation was not seen at the time of the re-challenge. In addition, only one test animal noted with barely perceptible erythema at the third induction had irritation at challenge. If the material resulted in sensitization, the response would be expected at both challenge and re-challenge as well as in a greater number of animals.

Based on the results of this study, the 4-B-2 and 0-B-2 were not considered to be a contact sensitizer in guinea pigs. This study, as described in Example 18, demonstrated that dosing of a mammal can be performed without developing a sensitization response at dosage levels of minocycline in the range of 0.1% to 4.0%, or preferably in the range of about 0.25% to about 2%, or more preferably in the range of about 0.5% to about 1.5%. Higher doses of minocycline allow more aggressive treatments. Dosages of at least about 0.20% or dosages of at least about 1.0% are preferred.

Example 19

Antioxidant Effect on Stability of Minocycline and Magnesium-Stabilized Minocycline The effect of the selection of antioxidant on drug potency, stability and epimer formation was evaluated for illustrative compositions. The degradation and stability of minocycline in compositions were evaluated at baseline and after storage for 1, 2, and 4 weeks in the dark at 40° C. within sealed glass vials. Efforts were taken to minimize (to the extent practical in a typical lab environment) the amount of empty space in the vial above each composition to reduce the interaction between the composition and any water vapor in the air.

Degradation of minocycline to its epimer was quantified by evaluating the change in the relative concentration of 4-epi-minocycline, which was calculated as the 4-epi-minocycline peak area divided by the sum of the 4-epi-minocycline peak area and the active minocycline peak area. As a separate quantification, stability was quantified by evaluating the change in the relative concentration of active minocycline, which was calculated as the active minocycline peak divided by the sum of the peak areas for all peaks observed in the HPLC chromatograph. For these measurements, a runtime of 20 minutes was used for the HPLC.

Each of the compositions evaluated in the study described in this example includes the materials described in Table 22.

The first six materials, i.e., minocycline hydrochloride, hydroxypropyl cellulose, magnesium chloride (anhydrous), ethanol (anhydrous), propylene glycol, and 1,8-cineole make up 99.8% of each of the evaluated compositions. The remaining 0.2% consisted of one of the antioxidants listed in Table 23 or consisted of ethanol (anhydrous) as a control.

TABLE 22

COMPOSITIONS FOR STABILITY EXPERIMENTS
WITH DIFFERENT ANTIOXIDANTS

| Component | Amount of composition by weight (i.e. (w/w)) |
|---|---|
| Minocycline hydrochloride | 1.2% |
| Hydroxypropyl cellulose | 0.6% |
| Magnesium chloride (anhydrous) | 1.2% |
| Ethanol (anhydrous) | 75.8% |
| Propylene Glycol | 20.0% |
| 1,8-Cineole | 1.0% |
| Antioxidant or ethanol (anhydrous) as defined in Table 23 | 0.2% |

The compositions were prepared as follows: The ethanol (anhydrous), propylene glycol, 1,8-cineole, and the antioxidant or ethanol (anhydrous) as defined in Table 23 were mixed until well dispersed. Magnesium chloride (anhydrous) and minocycline hydrochloride were added to the mixture and mixed until clear, or for 15 minutes if the mixture did not become clear. Hydroxypropyl cellulose (KLUCEL HF, Ashland Specialty Chemical, Wilmington Del.) was added slowly and mixed until clear, or for 15 minutes if mixture did not become clear.

TABLE 23

ANTIOXIDANTS FOR STABILITY EXPERIMENTS
WITH DIFFERENT ANTIOXIDANTS

| Composition Number | Antioxidant or Ethanol (anhydrous) |
|---|---|
| 2-ss | Sodium sulfite |
| 3-sb | Sodium bisulfite |
| 17-ps | Potassium sulfite |
| 1-sbs | Sodium metabisulfite |
| 5-bht | BHT |
| 16-ss | Sodium selenite |
| 6-toc | DL-alpha-tocopherol |
| 14-comb2 | Dithioerythreitol and DL-alpha-tocopherol |
| 9-se | Sodium erythorbate |
| 12-control | Ethanol (no antioxidant) |
| 13-comb1 | Ascorbic acid and DL-alpha-tocopherol |
| 8-dtt | Dithioerythreitol |
| 11-cat | Catechin |
| 10-pg | Propyl gallate |
| 15-comb3 | Dithioerythreitol and sodium erythorbate |
| 4-aa | Ascorbic acid |
| 7-sp | Sodium phosphite |
| 18-sn | Sodium nitrite |

Table 24 describes the measured relative concentration of 4-epi-minocycline and relative concentration of active minocycline within each composition. Measurements were taken at baseline and after 1-, 2-, and 4-weeks of aging at 40° C. in closed glass vials. The computer program JMP Statistical Software Tool (SAS Institute, Inc., Cary, N.C.) was used to evaluate the change in concentration per week based on the measured data for each composition to obtain a linear least squares best fit equation for each composition. The slope of this linear least squares best fit equation is presented in Table 24 as the rate of change in concentration over the 4-week aging period. Table 24 describes the baseline measurement and the best fit slope for the change per week.

TABLE 24

RELATIVE CONCENTRATIONS OF 4-EPI-MINOCYCLINE AND ACTIVE
MINOCYCLINE FOR 4-WEEK AGING STUDY AT 40° C.

| Composition Number (see Table 23) | Baseline relative concentration of 4-epi-minocycline (%) | Best fit relative concentration of 4-epi-minocycline increase per week at 40° C. (%/week) | Baseline relative concentration of active minocycline (%) | Best fit relative concentration of active minocycline decrease per week at 40° C. (%/week) | Significant color change after 4 weeks at 40° C. in closed glass vials |
|---|---|---|---|---|---|
| 2-ss | 0.58 | 0.271 | 98.64 | 0.317 | No |
| 3-sb | 0.59 | 0.340 | 98.76 | 0.365 | No |
| 17-ps | 0.77 | 0.399 | 98.51 | 0.400 | No |
| 1-sbs | 0.70 | 0.443 | 98.62 | 0.435 | No |
| 5-bht | 0.64 | 1.271 | 98.65 | 1.192 | Yes |
| 16-ss | 1.35 | 1.261 | 97.59 | 1.186 | Yes |
| 6-toc | 0.62 | 1.260 | 98.75 | 1.297 | Yes |
| 14-comb2 | 0.80 | 1.567 | 98.23 | 1.440 | Yes |
| 9-se | 0.84 | 1.092 | 97.64 | 1.509 | Yes |
| 12-control | 0.69 | 1.244 | 98.51 | 1.616 | Yes |
| 13-comb1 | 0.83 | 1.473 | 98.07 | 1.631 | Yes |
| 8-dtt | 0.83 | 1.702 | 98.48 | 1.639 | Yes |
| 11-cat | 0.84 | 1.645 | 98.66 | 1.646 | Yes |
| 10-pg | 0.83 | 1.711 | 98.77 | 1.726 | Yes |
| 15-comb3 | 0.83 | 1.078 | 97.14 | 1.831 | Yes |
| 4-aa | 0.70 | 1.397 | 97.70 | 2.270 | Yes |
| 7-sp | 0.86 | 2.682 | 98.33 | 2.773 | Yes |
| 18-sn | 25.94 | 14.145 | 61.34 | 13.595 | Yes |

Preferred compositions show a low baseline 4-epi-minocycline relative concentration and a small or no increase in 4-epi-minocycline relative concentration per week. For example, in some preferred compositions, the relative concentration of 4-epi-minocycline is less than 5.0% at a baseline measurement and increases less than 1.00% per week when measured over a 4-week period at 40° C. in closed glass vials, wherein the 4-week period starts immediately after the baseline measurement. In some preferred compositions, the relative concentration of 4-epi-minocycline is less than 1.0% at a baseline measurement and increases less than 1.00% per week when measured over a 4-week period at 40° C. in closed glass vials, wherein the 4-week period starts immediately after the baseline measurement. More preferably, the relative concentration of 4-epi-minocycline is less than 1.0% at a baseline measurement and increases less than 0.70% per week when measured over a 4-week period at 40° C. in closed glass vials, wherein the 4-week period starts immediately after the baseline measurement. Preferably, the relative concentration of 4-epi-minocycline is in the range of about 0.50% to about 1.00% at a baseline measurement and increases at a rate in the range of about 0.20% to about 0.40% per week when measured over a 4-week period at 40° C. in closed glass vials, wherein the 4-week period starts immediately after the baseline measurement.

Preferred compositions show a high active minocycline relative concentration and a small or no decrease in active minocycline relative concentration per week. For example, in some preferred compositions, the relative concentration of active minocycline is at least 95.0% at a baseline measurement and decreases less than 1.50% per week when measured over a 4-week period at 40° C. in closed glass vials, wherein the 4-week period starts immediately after the baseline measurement. In some preferred compositions, the relative concentration of active minocycline is at least 98.0% at a baseline measurement and decreases less than 1.00% per week when measured over a 4-week period at 40° C. in closed glass vials, wherein the 4-week period starts immediately after the baseline measurement. More preferably, the relative concentration of 4-epi-minocycline is at least 98.50% at a baseline measurement and decreases less than 0.70% per week when measured over a 4-week period at 40° C. in closed glass vials, wherein the 4-week period starts immediately after the baseline measurement. Preferably, the relative concentration of 4-epi-minocycline is in the range of about 97.0% to about 99.0% at a baseline measurement and decreases at a rate in the range of about 0.30% to about 1.00% per week when measured over a 4-week period at 40° C. in closed glass vials, wherein the 4-week period starts immediately after the baseline measurement.

This study further evaluated the difference in color between the compositions at baseline and after aging for 4 weeks at 40° C. in closed glass vials. The four compositions that included a sulfite compound as an antioxidant, i.e., compositions 2-ss, 3-sb, 17-ps, and 1-sbs, did not have a significant difference in color between the aged and baseline compositions. Each of the other compositions showed significant color differences. The strength of these color differences did not correlate with the amount of degradation of the relative concentration of the active minocycline. For example, compositions 5-bht, 12-control, and 16-ss darkened more significantly than compositions 8-dtt and 4-aa despite slower degradation of the relative concentration of the active minocycline for the three former compositions in comparison to the two latter compositions. Preferred compositions show no significant color changes after aging for 4 weeks at 40° C. in closed glass vials.

In preferred compositions, color change after aging for 4 weeks at 40° C. in closed glass vials is less than 50, or more preferably less than 20, in distance in 3-dimensional RGB space where each value is measured on a 0-255 range. Distance is calculated in 3-dimensional RGB space according to the following formula:

$$\text{distance}_{RGB} = ((\Delta R)^2 + (\Delta G)^2 + (\Delta B)^2)^{0.5}$$

Color change can be evaluated using a spectrocolorimeter (PANTONE CAPSURE, Model RM200, X-Rite, Inc., Grand Rapids, Mich.). Two microscope slides are used and a 1 mm spacer is placed between the slides. A pipette dispenses the composition to fill the space between the slides in the area to be evaluated. The microscope slides with the interposed composition are placed over a white piece of standard non-glossy copy paper. The spectrocolorimeter is placed on top of the upper microscope plate such that the field of view of the spectrocolorimeter is filled by the composition and the paper serves as a background for any light that penetrates through the composition.

It has been discovered that compositions employing a sulfite compound as an antioxidant were significantly more stable than those formulated using other antioxidants. Each of the evaluated compositions that comprised a sulfite-containing antioxidant, i.e., compositions 2-ss, 3-sb, 17-ps, and 1-sbs, showed at least 97.0% relative active minocycline concentration and showed a decrease in relative active minocycline concentration per week that was less than the corresponding decrease for all other compositions that were tested, including the control composition, i.e. composition 12-control. These four compositions comprised the antioxidants sodium sulfite, sodium bisulfite, potassium sulfite, and sodium metabisulfite, respectively. This demonstrates that sulfite compounds have superior antioxidant properties over generic antioxidants. Furthermore, many antioxidants, including those in compositions 13-comb1, 8-dtt, 11-cat, 10-pg, 15-comb3, 4-aa, 7-sp, and 18-sn, actually increased the rate of degradation of the active minocycline, despite the inclusion of an antioxidant. For these reasons, preferred compositions comprise an antioxidant selected from the list consisting of a sulfite compound, BHT, sodium selenite, DL-alpha tocopherol, a combination of dithioerythreitol and DL-alpha tocopherol, and sodium erythorbate. More preferably, compositions comprise a sulfite compound. More preferably, compositions comprise a sulfite salt selected from the list consisting of sodium sulfite, sodium bisulfite, potassium sulfite, and sodium metabisulfite.

Example 20

Stability Study of Minocycline and Magnesium-Stabilized Minocycline with Varied Water Content and pH The effects of the water content on drug potency stability and epimer formation were evaluated for illustrative compositions. Additionally, data were collected over a 12-month period to evaluate long-term drug potency stability and epimer formation for select illustrative compositions.

The stability of minocycline and epimer formation in compositions were evaluated at baseline and after storage within sealed glass vials which were kept at conditions specified by the International Conference on Harmonisation of Technical Requirements for Registration of Pharmaceuticals for Human Use (ICH)(Geneva, Switzerland) in its guideline "Stability Testing of New Drug Substances and Products" (dated Feb. 6, 2003). The test conditions evaluated include the following ICH designated conditions: "long term" (i.e., 25° C. and 60% relative humidity (RH)), "intermediate" (i.e., 30° C. and 65% RH), and "accelerated" (i.e., 40° C. and 75% RH).

The HPLC method described in this paragraph and the calculations described in the next paragraph are used only for this example. A 20 microliter (μL) sample is injected into a high-performance liquid chromatography machine (HPLC) (Agilent, Santa Clara, Calif.). The HPLC column (Thermo Scientific) was a HYPERSIL BDS C18 Column 250×4.6 mm with a particle size of 5 micrometers (μm). The HPLC system also used a guard column (Phenomenex, Inc.) and a mobile phase consisting of a base solvent of 12% (v/v) Dimethylformamide (Spectrum Chemicals, Gardena, Calif.), 8% Tetrahydrofuran (Spectrum Chemicals, Gardena, Calif.), 1.8 mM EDTA (Spectrum Chemicals, Gardena, Calif.), and 0.12 M Ammonium Oxalate (Spectrum Chemicals, Gardena, Calif.). The mobile phase was pH adjusted to 7.1-7.2. The HPLC flow rate was 1.5 mL per minute with a column temperature of 40° C., a detection wavelength of 280 nm, and a runtime of 30 minutes. The amount of minocycline that was in solution was determined based on an external calibration. This allowed calculation of the concentration of the minocycline hydrochloride.

Degradation of minocycline to its epimer was quantified by evaluating the change in the relative concentration of 4-epi-minocycline, which was calculated as the 4-epi-minocycline peak area divided by the sum of the 4-epi-minocycline peak area and the active minocycline peak area. As a separate quantification, stability was quantified by evaluating the change in the concentration of active minocycline, which was calculated by comparing the active minocycline peak area for the sample to the active minocycline peak area for a working standard. As a separate quantification, stability was further quantified by evaluating the change in the relative concentration of active minocycline, which was calculated as the active minocycline peak divided by the sum of the peak areas for all peaks observed in the HPLC chromatograph.

The working standard for minocycline was prepared by mixing 25 mg of USP minocycline hydrochloride RS into a 50 mL volumetric flask which was then filled with water to form 50 mL of solution. The working standard was protected from light, stored in a refrigerator if not used immediately, and used within 3 hours of preparation. The concentration of active minocycline in the working standard was calculated according to the equation $C=W*(100\%-KF)*(P\div V)$, wherein C (in units of mg/mL) was the concentration of the active minocycline, W (mg) was the weight of the minocycline hydrochloride, KF (%) was the proportion of water content added to create the solution, P was the potency of the minocycline, and V (mL) was the solution volume. The potency of the minocycline used for this Example was 0.917, or 91.7%.

Each of the compositions evaluated in the study described in this Example includes the materials described in Tables 25 and 26.

TABLE 25

COMPOSITIONS FOR ICH STABILITY EXPERIMENTS. ALL PERCENTAGES DESCRIBE THE AMOUNT BY WEIGHT (I.E., W/W)

| Component | Amount of composition (w/w) | | | | | |
|---|---|---|---|---|---|---|
| | SS-0001 | SS-0002 | SS-0003 | SS-0004 | SS-0005 | SS-0006 |
| Minocycline hydrochloride | 0.60% | 1.20% | 4.63% | 0.60% | 1.20% | 2.30% |
| Hydroxypropyl cellulose | 0.60% | 0.60% | 0.60% | 0.60% | 0.60% | 0.60% |
| Magnesium chloride (anhydrous) | 0.60% | 1.20% | 4.83% | 0.60% | 1.20% | 2.30% |
| Ethanol (anhydrous) | 72.78% | 71.74% | 64.44% | 77.00% | 75.80% | 68.60% |
| Propylene Glycol | 20.14% | 20.00% | 20.14% | 20.00% | 20.00% | 25.00% |
| 1,8-Cineole | 5.04% | 5.00% | 5.04% | 1.00% | 1.00% | 1.00% |
| Sodium metabisulfite | 0.20% | 0.20% | 0.20% | 0.20% | 0.20% | 0.20% |

TABLE 25-continued

COMPOSITIONS FOR ICH STABILITY EXPERIMENTS. ALL PERCENTAGES DESCRIBE THE AMOUNT BY WEIGHT (I.E., W/W)

| Component | Amount of composition (w/w) | | | | | |
|---|---|---|---|---|---|---|
| | SS-0001 | SS-0002 | SS-0003 | SS-0004 | SS-0005 | SS-0006 |
| Sodium hydroxide (delivered as part of 5% sodium hydroxide ethanol solution (w/w)) | 0.03% | 0.06% | 0.12% | — | — | — |

TABLE 26

ADDITIONAL COMPOSITIONS FOR ICH STABILITY EXPERIMENTS. ALL PERCENTAGES DESCRIBE THE AMOUNT BY WEIGHT (I.E., W/W)

| Component | Amount of composition (w/w) | | | | |
|---|---|---|---|---|---|
| | SS-0007 | SS-0008 | SS-0009 | SS-0010 | SS-0011 |
| Minocycline hydrochloride | 4.60% | 1.20% | 0.60% | 1.20% | 2.40% |
| Hydroxypropyl cellulose | 0.60% | 0.60% | 0.60% | 0.60% | 0.60% |
| Magnesium chloride (anhydrous) | 4.60% | 1.20% | — | — | — |
| Magnesium chloride (hexahydrate) | — | — | 1.30% | 2.60% | 5.10% |
| Ethanol (anhydrous) | 59.00% | 75.90% | 76.30% | 74.40% | 70.70% |
| Propylene Glycol | 30.00% | 20.00% | 20.00% | 20.00% | 20.00% |
| 1,8-Cineole | 1.00% | 1.00% | 1.00% | 1.00% | 1.00% |
| Sodium metabisulfite | 0.20% | 0.10% | 0.20% | 0.20% | 0.20% |

Each composition was prepared according to the following steps: The ethanol (anhydrous), propylene glycol, 1,8-cineole, and sodium metabisulfite were mixed until well dispersed. Magnesium chloride (anhydrous) and minocycline hydrochloride were added to the mixture and mixed until clear or for 15 minutes if mixture did not become clear. Hydroxypropyl cellulose (KLUCEL HF, Ashland Specialty Chemical, Wilmington Del.) was added slowly and mixed until clear. For compositions for which pH was increased, i.e. compositions SS-0001, SS-0002, and SS-0003, sodium hydroxide was added in the form of a 5% sodium hydroxide in ethanol solution.

Several of the compositions described in Tables 25 and 26 include sodium hydroxide to increase the pH of the composition. These pH adjusted compositions were designed to be better tolerated on the skin by being closer to a neutral pH. The ethanol listed in Tables 25 and 26 represents the total amount of ethanol (anhydrous) and ethanol from the sodium hydroxide ethanol solution. Other bases that are safe for application in topical formulations can be used in place of sodium hydroxide. The selection of such a base will be evident to those skilled in the art or can be evaluated without undue experimentation.

Tables 28 and 27 describe the measured concentration of 4-epi-minocycline as a proportion of the active minocycline peak and concentration of active minocycline within each composition. Measurements were taken at baseline and after aging in closed glass vials.

TABLE 27

CONCENTRATION OF ACTIVE MINOCYCLINE FOR STABILITY TESTING OF COMPOSITIONS OF EXAMPLE 20.

| Composition | Storage Condition | Concentration of active minocycline (w/w) | | | | | |
|---|---|---|---|---|---|---|---|
| | | Initial, T = 0 | T = 1 month | T = 3 months | T = 6 months | T = 9 months | T = 12 months |
| SS-0001 | 25° C./60% RH | 102.56% | 96.81% | 97.40% | 97.47% | N/A | N/A |
| | 30° C./65% RH | | 95.60% | 96.63% | N/A | N/A | N/A |
| | 40° C./75% RH | | 94.45% | 92.49% | N/A | N/A | N/A |
| SS-0002 | 25° C./60% RH | 106.48% | 97.63% | 99.24% | 99.91% | N/A | N/A |
| | 30° C./65% RH | | 98.33% | 98.79% | N/A | N/A | N/A |
| | 40° C./75% RH | | 97.15% | 95.37% | N/A | N/A | N/A |
| SS-0003 | 25° C./60% RH | 104.08% | 96.40% | 99.02% | 102.47% | N/A | N/A |
| | 30° C./65% RH | | 96.88% | N/A | N/A | N/A | N/A |
| | 40° C./75% RH | | N/A | 98.34% | N/A | N/A | N/A |
| SS-0004 | 25° C./60% RH | 96.10% | 96.14% | 99.12% | 98.92% | 98.25% | 100.31% |
| | 30° C./65% RH | | 96.84% | 98.23% | 95.36% | N/A | N/A |
| | 40° C./75% RH | | 96.05% | 94.65% | 88.62% | N/A | N/A |
| SS-0005 | 25° C./60% RH | 94.40% | 97.04% | 99.52% | 97.04% | 98.67% | 99.91% |
| | 30° C./65% RH | | 97.30% | 98.04% | 95.96% | N/A | N/A |
| | 40° C./75% RH | | 96.45% | 95.70% | 90.47% | N/A | N/A |
| SS-0006 | 25° C./60% RH | 96.90% | 93.52% | 96.65% | 93.52% | 94.07% | 96.49% |
| | 30° C./65% RH | | 94.85% | 94.96% | 91.35% | N/A | N/A |
| | 40° C./75% RH | | 92.81% | 90.82% | 83.81% | N/A | N/A |
| SS-0007 | 25° C./60% RH | 95.70% | 94.40% | 95.51% | 93.19% | 93.17% | 94.37% |
| | 30° C./65% RH | | 94.20% | 94.67% | 90.96% | N/A | N/A |
| | 40° C./75% RH | | 93.83% | 90.42% | 79.83% | N/A | N/A |
| SS-0008 | 25° C./60% RH | 98.40% | 97.19% | 99.12% | 95.95% | 96.77% | 95.79% |
| | 30° C./65% RH | | 96.28% | 97.61% | 94.34% | N/A | N/A |
| | 40° C./75% RH | | 95.55% | 93.21% | 85.77% | N/A | N/A |

TABLE 27-continued

CONCENTRATION OF ACTIVE MINOCYCLINE FOR STABILITY TESTING OF COMPOSITIONS OF EXAMPLE 20.

| | | Concentration of active minocycline (w/w) | | | | | |
|---|---|---|---|---|---|---|---|
| Composition | Storage Condition | Initial, T = 0 | T = 1 month | T = 3 months | T = 6 months | T = 9 months | T = 12 months |
| SS-0009 | 25° C./60% RH | 101.68% | 101.65% | 101.76% | 98.31% | N/A | N/A |
| | 30° C./65% RH | | 99.45% | 99.76% | N/A | N/A | N/A |
| | 40° C./75% RH | | 98.08% | 94.68% | 87.84% | N/A | N/A |
| SS-0010 | 25° C./60% RH | 100.73% | 101.09% | 99.74% | 98.85% | N/A | N/A |
| | 30° C./65% RH | | 99.07% | 98.66% | N/A | N/A | N/A |
| | 40° C./75% RH | | 97.23% | 93.64% | 87.01% | N/A | N/A |
| SS-0011 | 25° C./60% RH | 102.22% | 100.25% | 98.51% | 95.15% | N/A | N/A |
| | 30° C./65% RH | | 98.62% | 95.72% | N/A | N/A | N/A |
| | 40° C./75% RH | | 94.16% | 85.12% | 75.50% | N/A | N/A |

TABLE 28

CONCENTRATION OF 4-EPI-MINOCYCLINE FOR STABILITY TESTING OF COMPOSITIONS OF EXAMPLE 20.

| | | Concentration of active minocycline (w/w) | | | | | |
|---|---|---|---|---|---|---|---|
| Composition | Storage Condition | Initial, T = 0 | T = 1 month | T = 3 months | T = 6 months | T = 9 months | T = 12 months |
| SS-0001 | 25° C./60% RH | 0.64% | 1.09% | 1.66% | 2.72% | N/A | N/A |
| | 30° C./65% RH | | 1.31% | 1.93% | N/A | N/A | N/A |
| | 40° C./75% RH | | 2.53% | 5.85% | N/A | N/A | N/A |
| SS-0002 | 25° C./60% RH | 0.65% | 0.88% | 1.31% | 2.32% | N/A | N/A |
| | 30° C./65% RH | | 1.06% | 1.89% | N/A | N/A | N/A |
| | 40° C./75% RH | | 2.10% | 5.05% | N/A | N/A | N/A |
| SS-0003 | 25° C./60% RH | 0.67% | 0.79% | 1.05% | 1.58% | N/A | N/A |
| | 30° C./65% RH | | 0.91% | N/A | N/A | N/A | N/A |
| | 40° C./75% RH | | 1.57% | 2.51% | N/A | N/A | N/A |
| SS-0004 | 25° C./60% RH | 0.73% | 0.84% | 1.36% | 2.07% | 3.04% | 3.93% |
| | 30° C./65% RH | | 1.14% | 2.11% | 3.67% | N/A | N/A |
| | 40° C./75% RH | | 2.35% | 5.46% | 10.04% | N/A | N/A |
| SS-0005 | 25° C./60% RH | 0.73% | 0.81% | 1.34% | 1.93% | 2.77% | 4.26% |
| | 30° C./65% RH | | 0.99% | 1.93% | 3.61% | N/A | N/A |
| | 40° C./75% RH | | 1.85% | 4.98% | 9.69% | N/A | N/A |
| SS-0006 | 25° C./60% RH | 0.72% | 0.95% | 1.85% | 2.91% | 3.30% | 5.20% |
| | 30° C./65% RH | | 1.26% | 2.68% | 4.80% | N/A | N/A |
| | 40° C./75% RH | | 2.86% | 7.37% | 13.02% | N/A | N/A |
| SS-0007 | 25° C./60% RH | 0.79% | 1.18% | 2.29% | 3.80% | 5.14% | 5.40% |
| | 30° C./65% RH | | 1.61% | 3.58% | 5.72% | N/A | N/A |
| | 40° C./75% RH | | 4.13% | 8.98% | 15.95% | N/A | N/A |
| SS-0008 | 25° C./60% RH | 0.77% | 0.76% | 1.85% | 2.70% | 4.67% | 5.65% |
| | 30° C./65% RH | | 1.30% | 2.74% | 5.05% | N/A | N/A |
| | 40° C./75% RH | | 3.04% | 7.70% | 14.14% | N/A | N/A |
| SS-0009 | 25° C./60% RH | 0.78% | 1.13% | 1.66% | 2.90% | N/A | N/A |
| | 30° C./65% RH | | 1.43% | 2.62% | N/A | N/A | N/A |
| | 40° C./75% RH | | 2.80% | 7.24% | 14.76% | N/A | N/A |
| SS-0010 | 25° C./60% RH | 0.80% | 1.35% | 2.36% | 3.57% | N/A | N/A |
| | 30° C./65% RH | | 1.77% | 3.81% | N/A | N/A | N/A |
| | 40° C./75% RH | | 3.75% | 8.33% | 16.49% | N/A | N/A |
| SS-0011 | 25° C./60% RH | 0.64% | 2.17% | 4.85% | 8.34% | N/A | N/A |
| | 30° C./65% RH | | 3.29% | 7.34% | N/A | N/A | N/A |
| | 40° C./75% RH | | 7.66% | 18.26% | 27.23% | N/A | N/A |

Figure 14A:
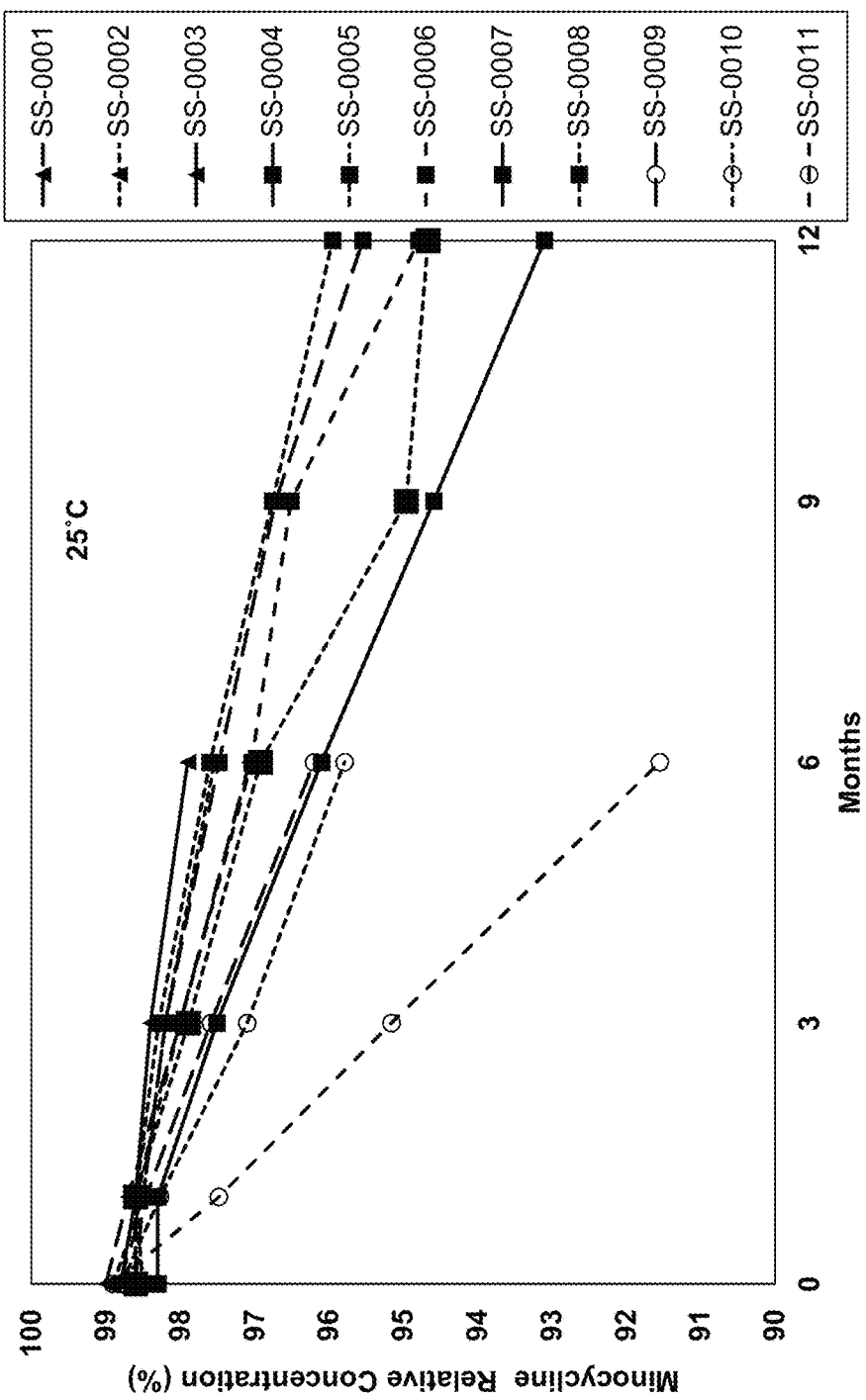
FIGS. 14A, 14B, and 14C are plots illustrating the relative concentration of minocycline in compositions described in Example 20 for aging conditions at 25° C., 30° C. and 40° C., respectively.
Figure 14B:
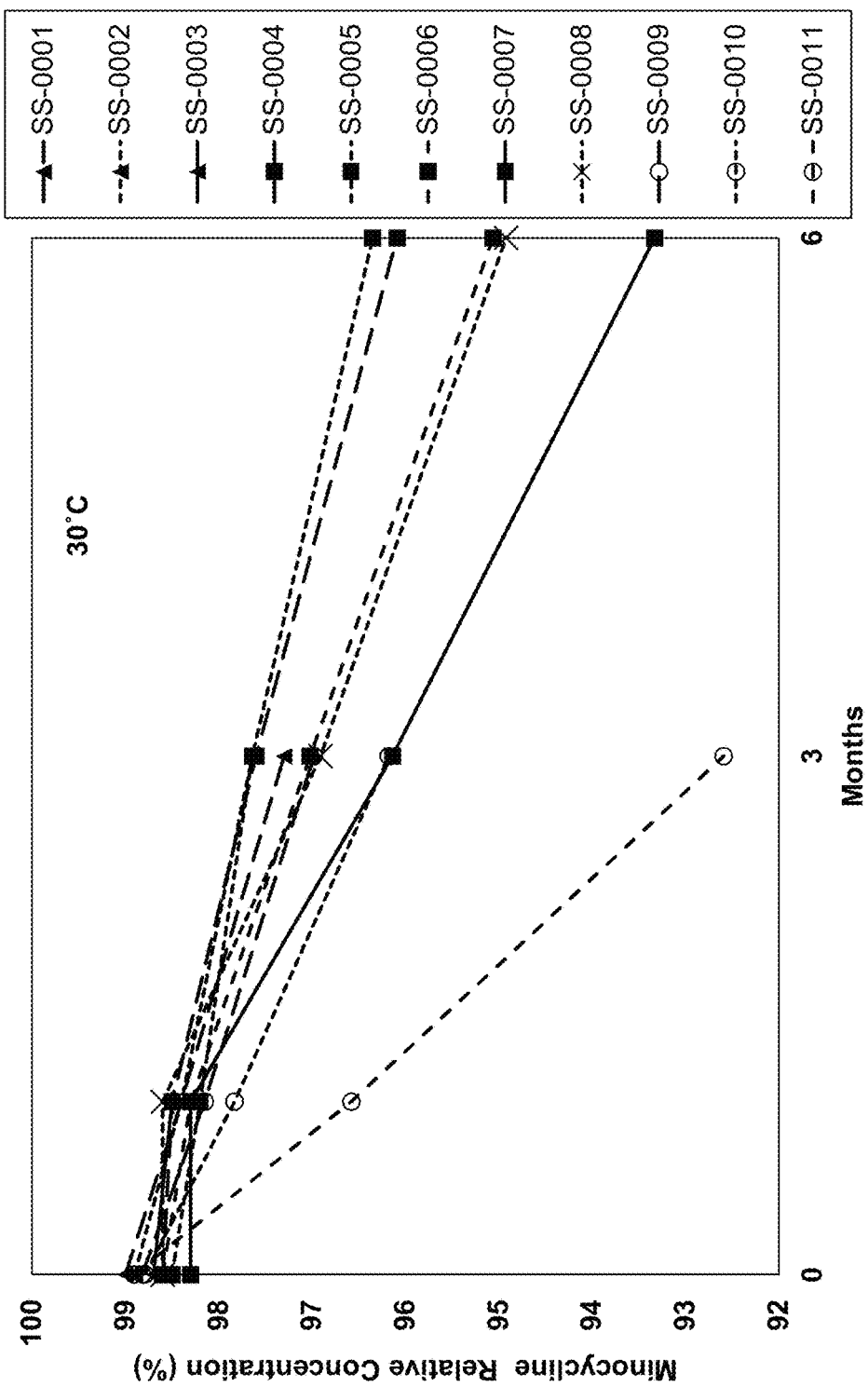
Figure 14C:
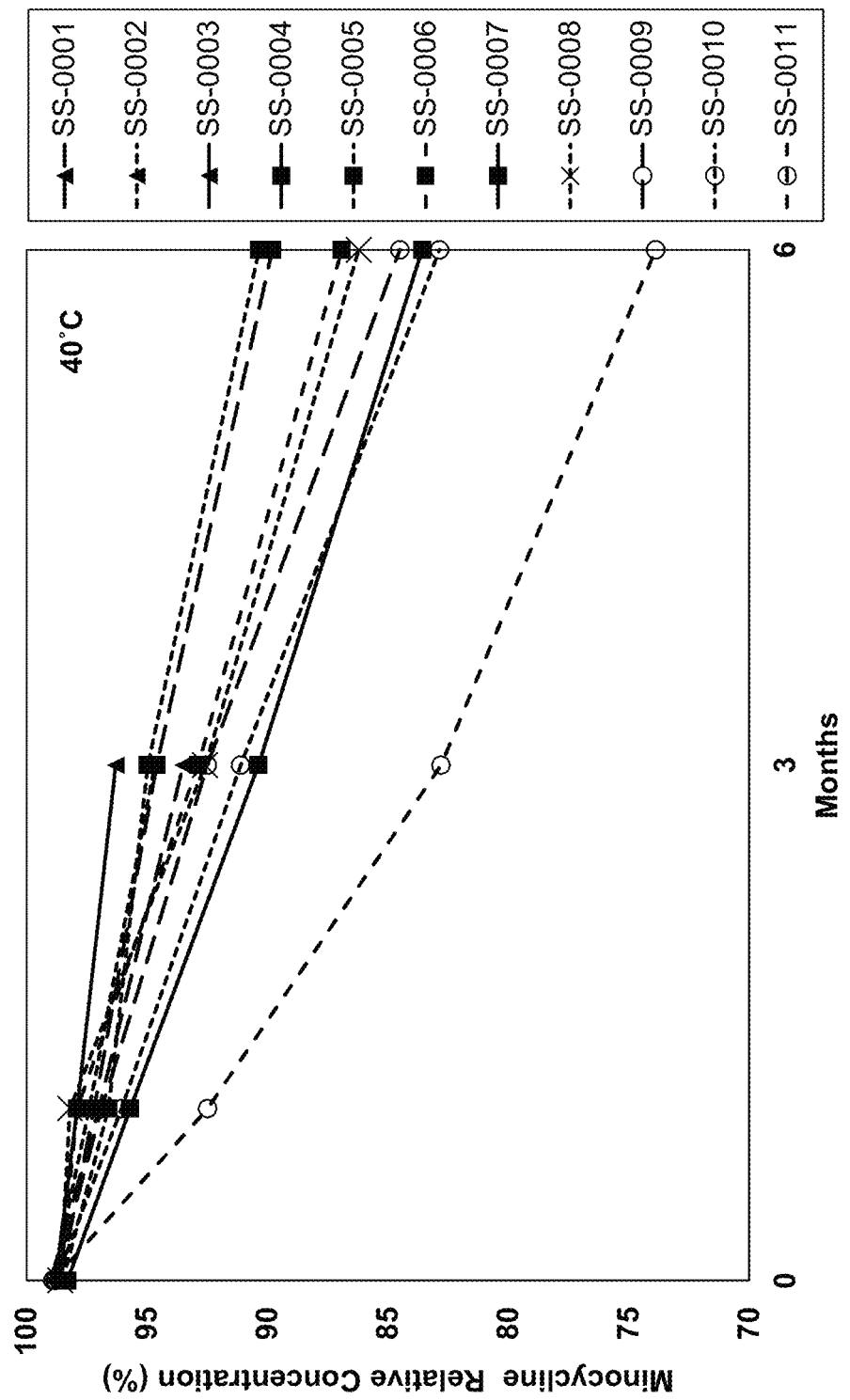

The relative concentrations for active minocycline for each of the compositions are presented in the graphs shown in FIGS. 14A, 14B, and 14C for aging at 25° C., 30° C., and 40° C., respectively. The slope was calculated for each of the least squares best fit lines in these graphs for each of the compositions to describe the degradation of the active minocycline within the composition and to allow comparisons among the compositions.

Several compositions in this study contained magnesium chloride anhydrous while other compositions contained magnesium chloride hexahydrate. The key difference between compositions SS-0004 to SS-0008 and SS-0009 to SS-0011 is that the magnesium chloride was added in the anhydrous form for the former and in the hexahydrate form for the later. This increased the amount of water content in each composition for the later and allowed a method for evaluating the effect of water on the stability of the composition.

Figure 15:
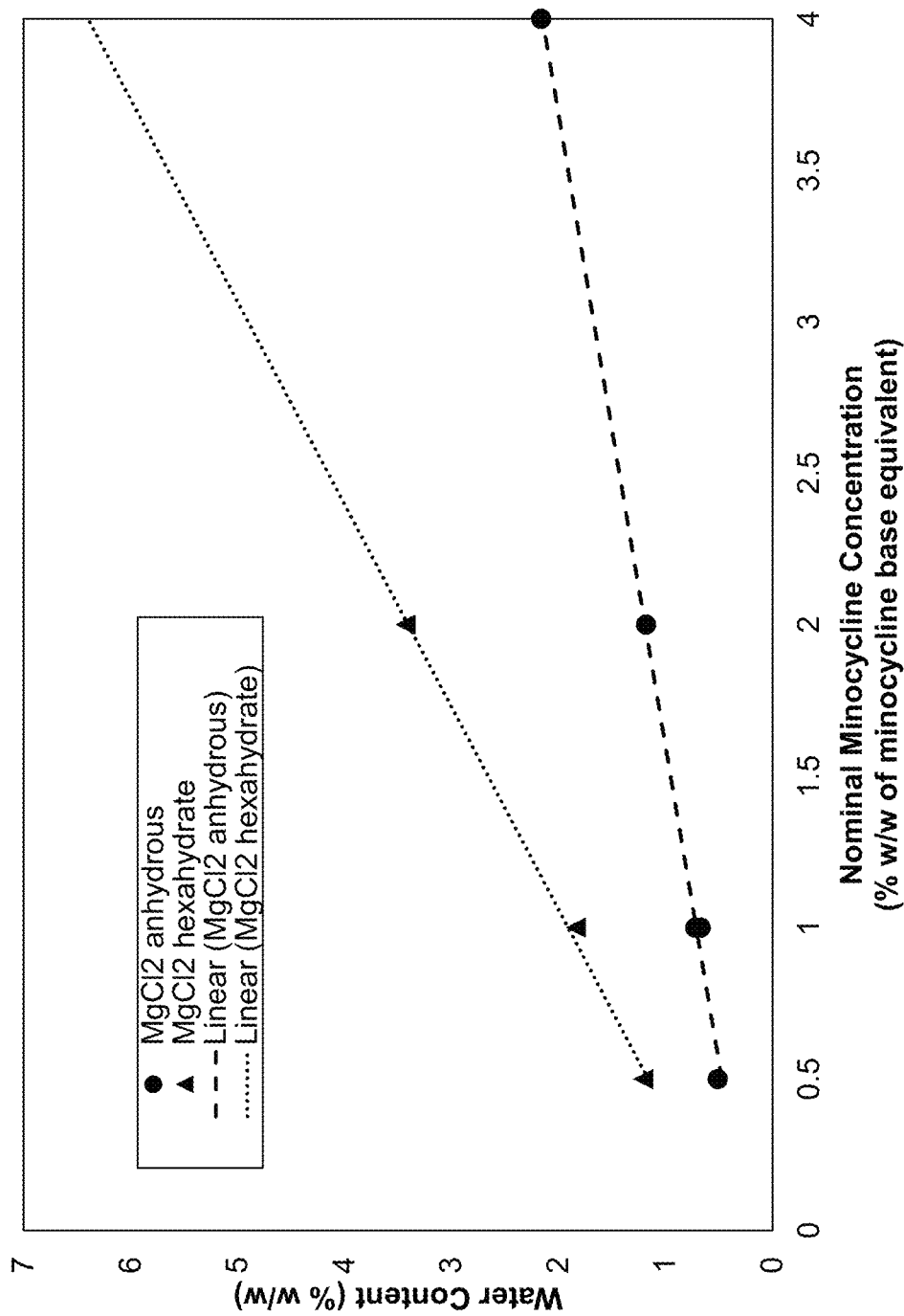
FIG. 15 is a plot illustrating the water content as a function of nominal minocycline concentration (base equivalent) for compositions SS-0004 to SS-0011 in Example 20.
Figure 16:
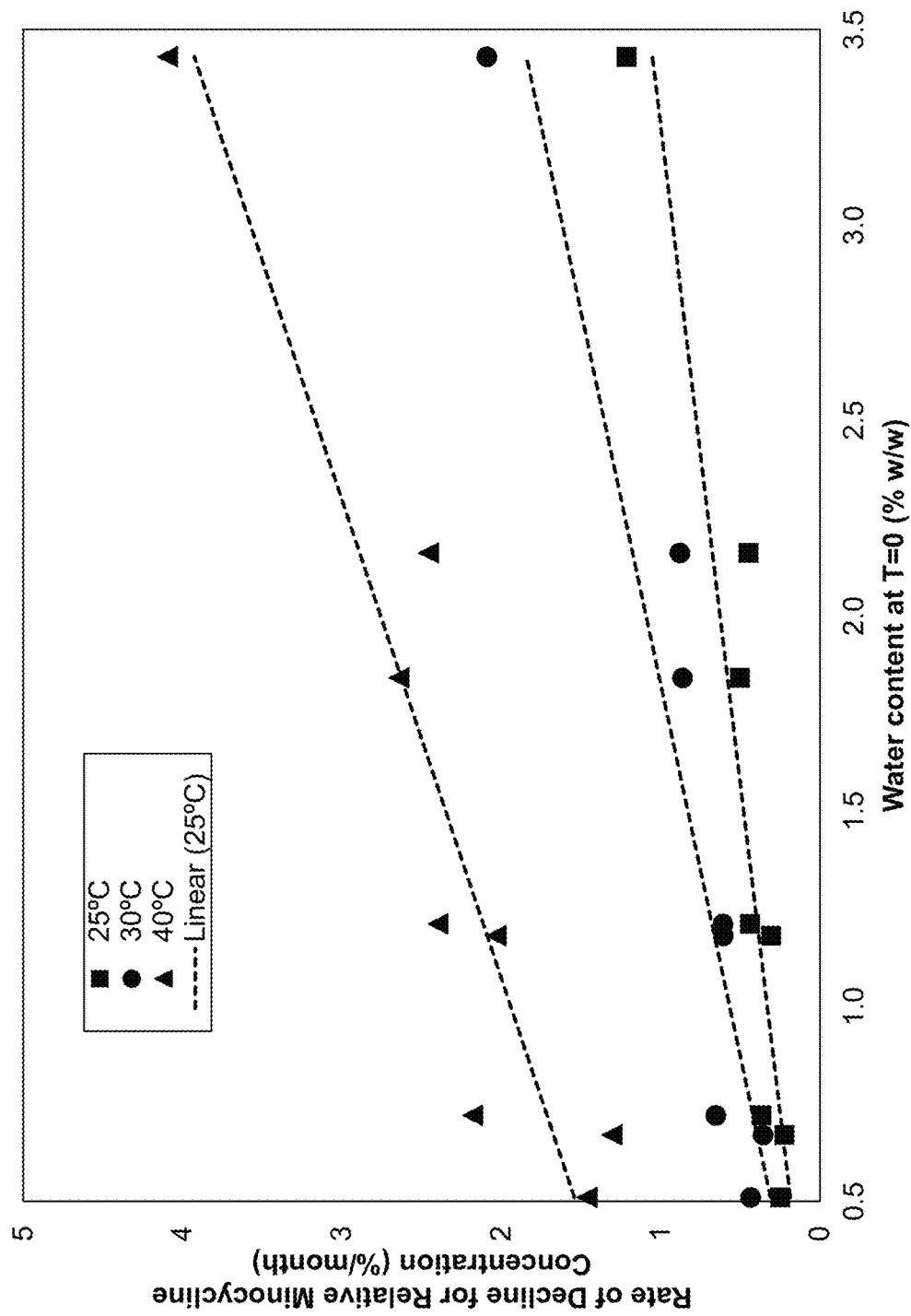
FIG. 16 is a plot illustrating the best fit rate of decline of the relative concentration of minocycline as a function of water content of the composition as measured by Karl Fischer titration after aging at 25° C. 30° C., and 40° C. as described in Example 20.

Since magnesium chloride was increased linearly with nominal active minocycline content, water content was increased for compositions with higher minocycline concentrations. FIG. 15 shows the amount of water in each of the compositions SS-0004 to SS-0011 as a function of nominal active minocycline content. Water content was measured by Karl Fischer titration. FIG. 16 shows the stability of these compositions as a function of water content and as a function of temperature. There is a correlation between increased water content and increased rate of degradation as described by the slope of the relative concentration of active minocycline in the concentration. To maintain a stable composition, in preferred compositions, it is desirable to have the water content for the composition to be less than 3.0%, preferably less than 2.0%, and more preferably less than 1.0%

The pH values for the compositions SS-0001 to SS-0011 varied in a range of about 3.8 to about 5.0. The effect of increasing the pH, such as through the addition of a base, can be seen by comparing compositions SS-0001 and SS-0002 to compositions SS-0004 and SS-0005. SS-0001 and SS-0002 included sodium hydroxide that increased the pH of the composition relative to that of the unadjusted compositions SS-0004 and SS-0005. Table 29 shows the calculated slopes for different test compositions assessed for different aging conditions. By comparing the degradation rates of minocycline for compositions SS-0001 and SS-0002 to those for composition SS-0004 and SS-0005, respectively, it can be determined that the stability of the composition is not changed by large amounts for small increases in pH. By this method, compositions with pH in the range of about 4.0 to about 6.0 may be created and may be desirable due to reduced irritation on the skin. More preferably, compositions have a pH range of about 4.5 to about 6.0, about 4.5 to about 5.5, or about 5.0 to about 6.0.

TABLE 29

SLOPE OF BEST FIT LINE FOR RELATIVE CONCENTRATION
FOR ACTIVE MINOCYCLINE IN UNITS OF % PER MONTH

|  | SS-0001 | SS-0002 | SS-0004 | SS-0005 |
|---|---|---|---|---|
| 25° C./60% RH | −0.32 | −0.21 | −0.22 | −0.31 |
| 30° C./65% RH | −0.56 | −0.41 | −0.36 | −0.61 |
| 40° C./75% RH | −1.82 | −1.40 | −1.31 | −2.03 |
| pH prior to aging | 4.95 | 4.70 | 4.70 | 4.30 |

Comparing composition SS-0003 to SS-0007 was not conducted as part of the evaluation of pH because the differing amounts of propylene glycol makes it more difficult to evaluate the cause of differences in stability, although the trends seen for those compositions are not inconsistent with those presented in this paragraph based on the other two pairs of composition.

Stability of active minocycline was not found to vary significantly for amounts of 1,8-cineole in the range of 1% to 5% within compositions. Examples of such compositions were presented in this Example.

Stability of active minocycline was found to vary based on the amount of propylene glycol in the composition. Replacing propylene glycol with alcohol made compositions generally made compositions more stable. Propylene glycol is beneficial, however, in that it increases the solubility of minocycline hydrochloride, reduces the evaporation rate of the composition when it is applied topically to human skin, reduces drying when the composition is applied topically to human skin, and promotes penetration of minocycline into the skin. Examples of compositions with varying amounts of propylene glycol were presented in this Example.

Example 21

Stability Study with Tetracycline Class Drugs

The effect of the selection of tetracycline class drug on drug potency stability and epimer formation was evaluated for illustrative compositions. Compositions were evaluated at baseline and after storage in the dark at 40° C. within sealed glass vials. For each of these studies, efforts were taken to minimize (to the extent practical in a typical lab environment) the amount of empty space in the vial above each composition to reduce the interaction between the composition and any water vapor in the air.

As for minocycline in many of the other Examples herein, drug potency stability for tetracycline was quantified by evaluating the change in the relative concentration of active tetracycline, which was calculated as the active tetracycline peak divided by the sum of the peak areas for all peaks observed in the HPLC chromatograph. For measurement of the amount of minocycline and tetracycline, the HPLC method that was used detected almost all of the degradation components and so the relative active drug measurement was deemed to be a more reliable and more representative method for detecting the amount of active drug in the composition than actual measurement of the drug peak relative to the peak for a standard. Repeated measurements have confirmed this assessment of the method. For doxycycline, the HPLC method did not detect a majority of the peaks for the degraded doxycycline components. So, for doxycycline, the amount of active doxycycline was calculated relative to the measurement of a doxycycline standard, rather than relative to the total peak area.

The HPLC method described in Example 21 was used for measurement of tetracycline and doxycycline, but with a flow rate of 0.8 mL/min instead of 1.0 mL/min.

The components of the compositions evaluated in the study described in this Example are listed in Tables 30 and 31.

TABLE 30

COMPOSITIONS FOR STABILITY EXPERIMENTS WITH TETRACYCLINE. ALL
PERCENTAGES DESCRIBE THE AMOUNT BY WEIGHT (I.E., W/W)

| | Amount of composition (w/w) | | | | | |
|---|---|---|---|---|---|---|
| Component | 1.0-Tet | 1.0-Tet-NSMBS | 1.0-Tet-NSMBS-NMg | 1.0-Tet-a | 1.0-Tet-NSMBS-a | 1.0-Tet-NSMBS-NMg-a |
| Tetracycline hydrochloride (Sigma-Aldrich Corp., St. Louis, MO) | 1.0% | 1.0% | 1.0% | 0.97% | 0.97% | 0.97% |
| Hydroxypropyl cellulose | 0.6% | 0.6% | 0.6% | 0.58% | 0.58% | 0.58% |
| Magnesium chloride (anhydrous) | 1.20% | 1.20% | — | 1.17% | 1.17% | — |
| Ethanol (anhydrous) | 76.00% | 76.20% | 77.40% | 76.58% | 76.78% | 77.94% |
| Propylene Glycol | 20.00% | 20.00% | 20.00% | 19.42% | 19.42% | 19.42% |

TABLE 30-continued

COMPOSITIONS FOR STABILITY EXPERIMENTS WITH TETRACYCLINE. ALL PERCENTAGES DESCRIBE THE AMOUNT BY WEIGHT (I.E., W/W)

| | Amount of composition (w/w) | | | | | |
|---|---|---|---|---|---|---|
| Component | 1.0-Tet | 1.0-Tet-NSMBS | 1.0-Tet-NSMBS-NMg | 1.0-Tet-a | 1.0-Tet-NSMBS-a | 1.0-Tet-NSMBS-NMg-a |
| 1,8-Cineole | 1.00% | 1.00% | 1.00% | 0.97% | 0.97% | 0.97% |
| Sodium metabisulfite | 0.20% | — | — | 0.19% | — | — |
| Sodium hydroxide (delivered as part of 5% sodium hydroxide ethanol solution (w/w)) | — | — | — | 0.11% | 0.11% | 0.11% |

TABLE 31

COMPOSITIONS FOR STABILITY EXPERIMENTS WITH DOXYCYCLINE. ALL PERCENTAGES DESCRIBE THE AMOUNT BY WEIGHT (I.E., W/W)

| | Amount of composition (w/w) | | | | | |
|---|---|---|---|---|---|---|
| Component | 1.0-Doxy | 1.0-Doxy-NSMBS | 1.0-Doxy-NSMBS-NMg | 1.0-Doxy-a | 1.0-Doxy-NSMBS-a | 1.0-Doxy-NSMBS-NMg-a |
| Doxycycline hyclate (Sigma-Aldrich Corp., St. Louis, MO) | 1.2% | 1.2% | 1.2% | 1.16% | 1.16% | 1.16% |
| Hydroxypropyl cellulose | 0.6% | 0.6% | 0.6% | 0.58% | 0.58% | 0.58% |
| Magnesium chloride (anhydrous) | 1.20% | 1.20% | — | 1.16% | 1.16% | — |
| Ethanol (anhydrous) | 75.80% | 76.00% | 77.20% | 76.45% | 76.64% | 77.81% |
| Propylene Glycol | 20.00% | 20.00% | 20.00% | 19.36% | 19.36% | 19.36% |
| 1,8-Cineole | 1.00% | 1.00% | 1.00% | 0.97% | 0.97% | 0.97% |
| Sodium metabisulfite | 0.20% | — | — | 0.19% | — | — |
| Sodium hydroxide (delivered as part of 5% sodium hydroxide ethanol solution (w/w)) | — | — | — | 0.12% | 0.12% | 0.12% |

Each composition was prepared according to the following steps: The ethanol (anhydrous), propylene glycol, 1,8-cineole, and sodium metabisulfite were mixed until well dispersed. Magnesium chloride (anhydrous) and either tetracycline hydrochloride or doxycycline hyclate were added to the mixture and mixed until clear or for 15 minutes if mixture did not become clear. Hydroxypropyl cellulose (KLUCEL HF, Ashland Specialty Chemical, Wilmington Del.) was added slowly and mixed until clear. For compositions for which pH was increased, i.e. compositions designated by "-a" at the end of the composition identifier, sodium hydroxide was added in the form of a 5% sodium hydroxide in ethanol solution.

Several of the compositions described in Tables 30 and 31 include sodium hydroxide to increase the pH of the composition. These pH adjusted compositions were designed to be better tolerated on the skin by being closer to a neutral pH. The ethanol listed in Tables 30 and 31 represents the total amount of ethanol (anhydrous) and ethanol from the sodium hydroxide ethanol solution. Other bases that are safe for application in topical formulations can be used in place of sodium hydroxide. The selection of such a base will be evident to those skilled in the art or can be evaluated without undue experimentation.

Table 32 describes the measured relative concentration of active tetracycline within each composition containing tetracycline. Measurements were taken at baseline and after aging at 40° C. in closed glass vials. The data in Table 32 demonstrate that the stability of tetracycline was degraded by the inclusion of magnesium chloride in the composition or by the inclusion of magnesium chloride and SMBS in the composition. Stability was lowered for both the pH buffered composition and the unbuffered composition. For most applications, these compositions are not sufficiently stable for commercial deployment without refrigeration. Such compositions are sufficiently stable for some applications with appropriate storage conditions, such as maintaining the composition at a temperature of 5° C.±3° C.

TABLE 32

RELATIVE CONCENTRATIONS OF ACTIVE TETRACYCLINE FOR AGING STUDY AT 40° C.

| Composition Number (see Table 30) | pH | Baseline relative active tetracycline concentration (%) | Relative active tetracycline concentration after 7 days at 40° C. (%) | Significant color change after 7 days at 40° C. in closed glass vials |
|---|---|---|---|---|
| 1.0-Tet | 3.3 | 82.51% | 1.95% | No |
| 1.0-Tet-NSMBS | 3.1 | 67.86% | 4.30% | No |
| 1.0-Tet-NSMBS-NMg | 3.2 | 98.10% | 88.22% | Yes (slight) |
| 1.0-Tet-a | 5.4 | 80.74% | 4.46% | No |

TABLE 32-continued

RELATIVE CONCENTRATIONS OF ACTIVE TETRACYCLINE
FOR AGING STUDY AT 40° C.

| Composition Number (see Table 30) | pH | Baseline relative active tetracycline concentration (%) | Relative active tetracycline concentration after 7 days at 40° C. (%) | Significant color change after 7 days at 40° C. in closed glass vials |
|---|---|---|---|---|
| 1.0-Tet-NSMBS-a | 4.5 | 66.15% | 1.78% | No |
| 1.0-Tet-NSMBS-NMg-a | 6.5 | 96.17% | 22.67% | Yes |

TABLE 33

CONCENTRATIONS OF ACTIVE DOXYCYCLINE
FOR AGING STUDY AT 40° C.

| Composition Number (see Table 31) | pH | Baseline active doxycycline concentration (%) | Active doxycycline concentration after 7 days at 40° C. (%) | Significant color change after 7 days at 40° C. in closed glass vials |
|---|---|---|---|---|
| 1.0-Doxy | 3.1 | 97.0% | 92.7% | No |
| 1.0-Doxy-NSMBS | 2.9 | 95.8% | 88.6% | No |
| 1.0-Doxy-NSMBS-NMg | 3.0 | 94.5% | 88.7% | Yes (slight) |
| 1.0-Doxy-a | 4.8 | 97.1% | 93.8% | No |
| 1.0-Doxy-NSMBS-a | 4.5 | 96.6% | 90.4% | No |
| 1.0-Doxy-NSMBS-NMg-a | 6.4 | 96.3% | 24.4% | Yes |

Table 33 describes the measured concentration of active doxycycline within each composition containing doxycycline. Measurements were taken at baseline and after aging at 40° C. in closed glass vials for 7 and 21 days. These data demonstrate that the stability of doxycycline was enhanced by the inclusion of magnesium chloride in the composition or by the inclusion of magnesium chloride and SMBS in the composition. If a pH buffered composition is desired, the data show that inclusion of magnesium chloride was more beneficial for the buffered composition than for the unbuffered composition. In some applications doxycycline may be stable enough in one or more of these compositions to be useful for treatment of dermatological conditions described herein, even without refrigeration.

Figures 13A, 13B:
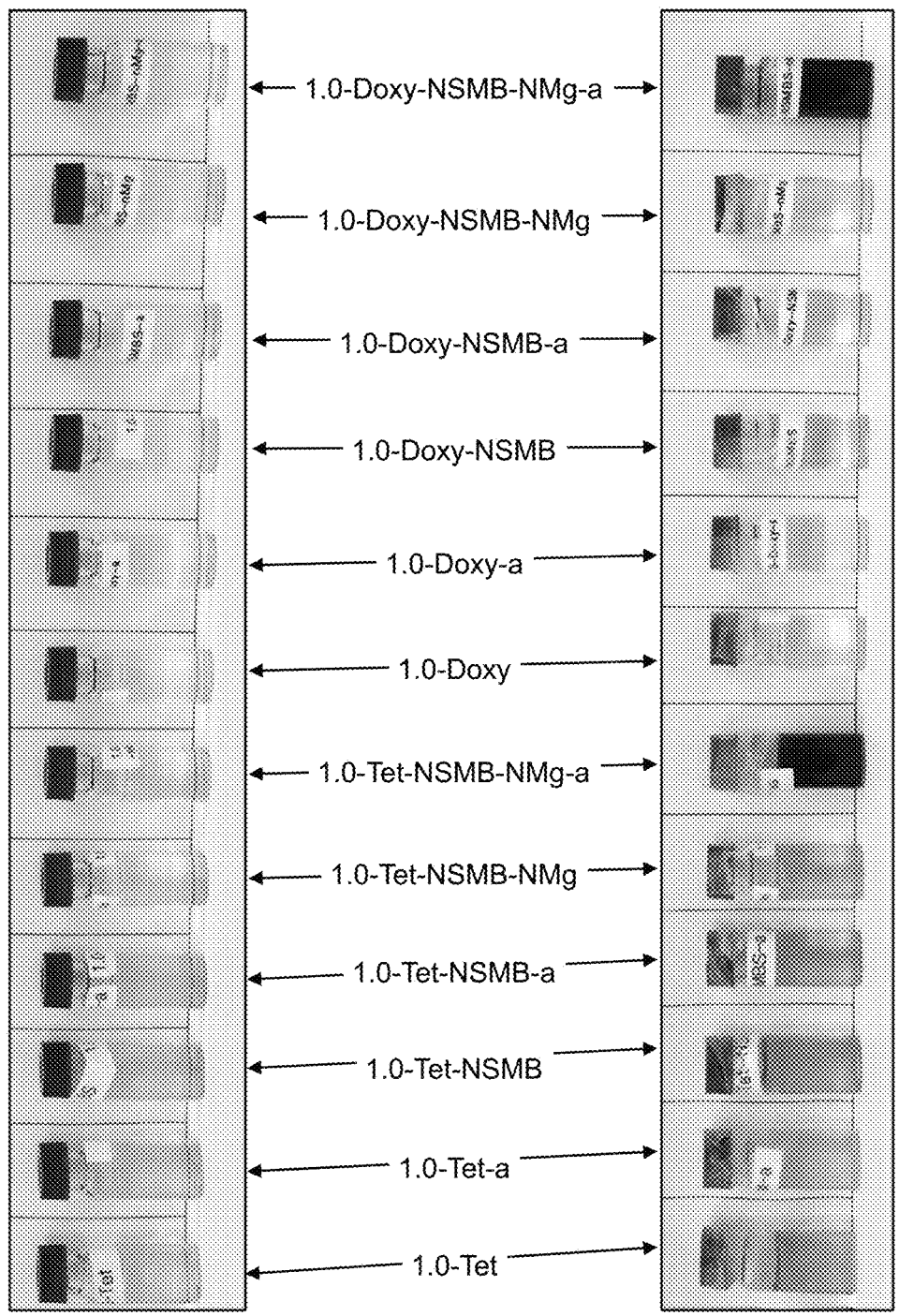
FIGS. 13A and 13B are photographs of compositions containing tetracycline and doxycycline prior to and after aging at 40° C. in closed glass vials for 7 days.

FIGS. 13A and 13B shows the color of each of the compositions in Tables 30 and 31 prior to (FIG. 13A) and after (FIG. 13B) aging at 40° C. in closed glass vials for 7 days. Color changes occurred during the 7-day aging period for several of the compositions as described in Tables 32 and 33.

Based on the data in this Example and the other Examples herein, minocycline and doxycycline are preferred forms of tetracycline class drugs for use in the compositions described herein because of their superior stability in comparison to tetracycline. Other tetracycline class drugs can be evaluated in the compositions described herein to evaluate the suitability of their stability for a particular application for a topical composition.

Example 22

Penetration into Ex Vivo Human Skin: A Comparison of Three Tetracycline Class Drugs Penetration experiments with ex vivo skin tissue were conducted to determine the penetration efficiencies of three active tetracycline class drugs into skin when comprised within compositions comprising a source of magnesium, a monohydric aliphatic alcohol, and a polyol and applied to the skin surface. The penetration into abdominal skin was assessed for three different human donors with three samples for each donor for each drug in the study for a total of nine measurements per composition. The tested tetracycline class drugs included tetracycline, minocycline, and doxycycline. The compositions assessed as part of this study are described in Table 34.

TABLE 34

COMPOSITIONS FOR SKIN PENETRATION EXPERIMENT

| | Amount of composition (w/w) | | |
|---|---|---|---|
| Component | Tetra-1 | Doxy-1 | Mino-1 |
| Tetracycline hydrochloride (Sigma-Aldrich Corp., St. Louis, MO) | 2.38% | — | — |
| Doxycycline hyclate (Sigma-Aldrich Corp., St. Louis, MO) | — | 4.00% | — |
| Minocycline hydrochloride (Euticals S.P.A, Origgio, Italy) | — | — | 4.60% |
| Hydroxypropyl cellulose | 0.68% | 0.67% | 0.6% |
| Magnesium chloride (anhydrous)(Magnesium Products, Tulsa, OK) | 4.74% | 4.66% | 4.60% |
| Ethanol (anhydrous) | 60.21% | 59.21% | 59.00% |
| Propylene Glycol | 30.44% | 29.94% | 30.0% |
| 1,8-Cineole | 1.35% | 1.33% | 1.00% |
| Sodium metabisulfite | 0.20% | 0.20% | 0.20% |

The compositions were applied to skin samples from three human donors at a dose of about 12 mg/cm$^2$. Tissue was maintained in a damp environment to limit drying of the tissue and incubated at 32° C. for 3 hours. At the end of the incubation period, excess composition was wiped from the surface using first a dry gauze pad, second a gauze pad soaked with 70% isopropyl alcohol, and finally with a dry gauze pad. Tape stripping was performed to remove the upper layers of the stratum corneum. A six (6) millimeter punch biopsy was taken from within the test area. The tetracycline class drug was extracted from each biopsy using acidified methanol. The supernatants were analyzed by high performance liquid chromatography.

The results of this study demonstrated that the efficiency of penetration for doxycycline, minocycline, and tetracycline was sufficient to exceed the minimum inhibitory concentration for each of these active drugs and thus would be useful for killing bacteria on or within the skin, such as *P. acnes*. Doxycycline and minocycline demonstrated higher efficiency of penetration than tetracycline. For this reason, doxycycline and/or minocycline are preferred over tetracycline for some applications.

It is claimed:
1. A topical composition comprising minocycline, a magnesium salt, and a sulfite compound in a non-aqueous solvent, wherein the minocycline is dissolved in the composition and the composition is non-aqueous.

2. The topical composition of claim 1, wherein the non-aqueous solvent comprises a monohydric aliphatic alcohol and a polyol.

3. The topical composition of claim 2, wherein the ratio between the monohydric aliphatic alcohol and the polyol is in the range of 1:1 to 99:1 by weight.

4. The topical composition of claim 3, comprising a greater percentage by weight of the monohydric aliphatic alcohol than the polyol.

5. The topical composition of claim 4, wherein the w/w ratio of monohydric aliphatic alcohol and polyol is in a range of about 2:1 to 10:1 by weight.

6. The topical composition of claim 1, wherein the molar ratio of the magnesium salt to the minocycline is in a range of about 2:1 to 100:1.

7. The topical composition of claim 1, wherein the magnesium salt is magnesium chloride, or is a minocycline salt having a counter ion that is softer than chloride.

8. The topical composition of claim 1, wherein the monohydric aliphatic alcohol is selected from the group consisting of ethanol, isopropanol, propyl alcohol, tert-butyl alcohol, or combinations thereof.

9. The topical composition of claim 8, wherein the monohydric aliphatic alcohol is ethanol.

10. The topical composition of claim 1, comprising from about 0.1% to about 4% by weight minocycline.

11. The topical composition of claim 1, which when stored at 40° C. in a closed glass vial for a period of 4 weeks, exhibits an increase in the relative concentration of 4-epi-minocycline of less than 1.0% per week.

12. The topical composition of claim 2, which when stored at 40° C. in a closed glass vial for a period of 4 weeks, exhibits an increase in the relative concentration of 4-epi-minocycline of less than 0.70% per week.

13. The topical composition of claim 1, which when stored at 25° C. and 60% relative humidity in a sealed container for 12 months, contains less than 7% minocycline degradation product, where the degradation product is 4-epi-minocycline.

14. The topical composition of claim 2, wherein the polyol is a C3-C8 diol or a triol.

15. The topical composition of claim 14, wherein the polyol is propylene glycol.

16. The topical composition of claim 1, wherein the sulfite compound is a sulfite, bisulfite, pyrosulfite, or metabisulfite.

17. The topical composition of claim 16, wherein the sulfite compound is an inorganic sulfite salt comprising an inorganic cation selected from sodium, potassium, calcium and magnesium.

18. The topical composition of claim 1 comprising from about 0.005% to about 3.0% by weight of the sulfite compound.

19. The topical composition of claim 18, wherein the sulfite is selected from the group consisting of sodium sulfite, sodium bisulfite, and sodium meta-bisulfite.

20. The topical composition of claim 1, comprising less than about 3 weight percent water.

21. The topical composition of claim 20, comprising less than about 2 weight percent water.

22. The topical composition of claim 1, further comprising an essential oil.

23. The topical composition of claim 22, comprising 0.01 to 5 weight percent of 1,8-cineole.

24. The topical composition of claim 1, comprising a thickening agent.

25. The topical composition of claim 24, wherein the thickening agent is hydroxypropyl cellulose.

26. The topical composition of claim 1, wherein the composition is not an emulsion and/or does not comprise nanoparticles or microparticles.

27. The topical composition of claim 1, having an effective pH of 3-6 when mixed with water in a ratio of 1:9 by weight.

28. The topical composition of claim 27, having an effective pH of about 3.8 to about 5.0 when mixed with water in a ratio of 1:9 by weight.

29. The topical composition of claim 1, wherein the non-aqueous solvent comprises a monohydric aliphatic alcohol.

30. The topical composition of claim 1, wherein the composition is non-irritating when applied to rats daily over a period of 28 days.

31. The topical composition of claim 1, wherein the composition exhibits no significant change in color after aging for 4 weeks at 40° C. in a sealed container.

32. The topical composition of claim 31, wherein no significant color change is a color change of less than 20 in distance in 3-dimensional RGB space where each value is measured on a 0-255 range and distance is calculated in 3-dimensional RGB space according to the following formula: $\text{distance}_{RGB}=((\Delta R)^2+(\Delta G)^2+(\Delta B)^2)^{0.5}$.

33. A topical composition comprising a tetracycline-class drug, a magnesium salt, a monohydric aliphatic alcohol and a polyol, wherein (i) the ratio between the monohydric aliphatic alcohol and the polyol is in a range of 1:1 to 99:1 by weight, and (ii) the tetracycline-class drug is dissolved in the topical composition,
wherein the topical composition is non-aqueous.

34. The topical composition of claim 33, wherein the polyol is propylene glycol.

35. The topical composition of claim 33, further comprising an antioxidant.

36. The topical composition of claim 33, wherein the tetracycline class drug is minocycline.

37. The topical composition of claim 33, wherein the composition is hydrophilic.

38. The topical composition of claim 33, wherein the penetration efficiency into ex vivo human facial skin is equal to or exceeds 5%.

39. A method for treating a dermatological inflammation or infection comprising applying the topical composition of claim 1 to an exterior epithelial surface of a mammalian body in need thereof at least once daily for a period of at least 1 week.

40. A method for treating a dermatological inflammation or infection comprising applying the topical composition of claim 1 to an exterior epithelial surface of a mammalian body in need thereof at least once daily for a period of at least 1 month.

41. A method for making a topical composition, the method comprising (i) combining minocycline, a magnesium salt, and a sulfite compound in a non-aqueous solvent to form a mixture, and (ii) agitating the mixture from (i) to form a solution in which the minocycline is dissolved, thereby obtaining a composition of claim 1.

42. A method for making a topical composition, the method comprising (i) combining a tetracycline-class drug, a magnesium salt, a volatile monohydric aliphatic alcohol, and a polyol to form a mixture, and (ii) agitating the mixture from (i) to form a solution in which the tetracycline-class drug is dissolved, thereby obtaining a composition of claim 33.

* * * * *